n(12) United States Patent
Henry et al.

(10) Patent No.: US 10,730,046 B2
(45) Date of Patent: Aug. 4, 2020

(54) FLUID HANDLING SYSTEMS FOR APPLICATION OF FLUID SHEAR STRESS TO A FLUID SAMPLE

(71) Applicant: UNIVERSITY OF IOWA RESEARCH FOUNDATION, Iowa City, IA (US)

(72) Inventors: Michael D. Henry, Iowa City, IA (US); Sarah C. Vigmostad, Iowa City, IA (US); Michael Cable, Iowa City, IA (US); Benjamin L. Krog, Iowa City, IA (US); Eric Leopold, Iowa City, IA (US); Rupesh Desai, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 402 days.

(21) Appl. No.: 15/522,704

(22) PCT Filed: Oct. 30, 2015

(86) PCT No.: PCT/US2015/058255
§ 371 (c)(1),
(2) Date: Apr. 27, 2017

(87) PCT Pub. No.: WO2016/070007
PCT Pub. Date: May 6, 2016

(65) Prior Publication Data
US 2017/0333896 A1   Nov. 23, 2017

Related U.S. Application Data

(60) Provisional application No. 62/073,142, filed on Oct. 31, 2014.

(51) Int. Cl.
*B01L 3/00* (2006.01)
*B01J 4/00* (2006.01)
(Continued)

(52) U.S. Cl.
CPC .......... *B01L 3/50273* (2013.01); *B01J 4/001* (2013.01); *B01J 19/0093* (2013.01); *B01L 3/56* (2013.01);
(Continued)

(58) Field of Classification Search
CPC combination set(s) only.
See application file for complete search history.

(56) References Cited

U.S. PATENT DOCUMENTS

2001/0052460 A1* 12/2001 Chien ............... B01L 3/502715
  204/450
2002/0006359 A1*  1/2002 Mathies ................ B01L 3/0293
  422/400

(Continued)

FOREIGN PATENT DOCUMENTS

| WO | 2012129360 A2 | 9/2012 |
| WO | 2013086509 A1 | 6/2013 |
| WO | 2014070776 A1 | 5/2014 |

OTHER PUBLICATIONS

Barnes, et al., "Resistance to fluid shear stress is a conserved biophysical property of malignant cells.", PLoS One 7 (12), 1-12 (2012).

(Continued)

*Primary Examiner* — Brian R Gordon
(74) *Attorney, Agent, or Firm* — Viksnins Harris Padys Malen LLP

(57) ABSTRACT

A fluid handling system for applying a plurality of pulses of fluid shear stress to a fluid sample may comprise a first sample chamber; a second sample chamber; a plurality of conduits mounted between and in fluid communication with the first sample chamber and the second sample chamber; and a force delivery system mounted to the first sample chamber and configured to apply a force sufficient to push the fluid sample from the first sample chamber through each (Continued)

of the conduits at a substantially constant flow rate to the second sample chamber. The plurality of conduits may be arranged in series and separated by additional sample chambers or arranged such that the conduits are substantially parallel to one another. The force delivery system may be a gas delivery system or a linear drive assembly.

18 Claims, 37 Drawing Sheets

(51) Int. Cl.
*B01J 19/00* (2006.01)
*C12M 1/42* (2006.01)

(52) U.S. Cl.
CPC ........ *C12M 35/04* (2013.01); *B01J 2219/009* (2013.01); *B01L 2200/06* (2013.01); *B01L 2200/0647* (2013.01); *B01L 2200/0689* (2013.01); *B01L 2300/087* (2013.01); *B01L 2300/0832* (2013.01); *B01L 2400/0478* (2013.01); *B01L 2400/0487* (2013.01)

(56) References Cited

U.S. PATENT DOCUMENTS

| | | | | |
|---|---|---|---|---|
| 2002/0036018 A1* | 3/2002 | McNeely | ............. | B01F 5/0403 137/806 |
| 2003/0041652 A1* | 3/2003 | Spaid | ................... | B01L 3/5027 73/54.05 |
| 2003/0221996 A1 | 12/2003 | Svoronos et al. | | |
| 2004/0142408 A1 | 7/2004 | Kirk et al. | | |
| 2004/0182788 A1* | 9/2004 | Dorian | ................... | B01D 15/02 210/649 |
| 2004/0213699 A1* | 10/2004 | Berndtsson | ............. | B01L 3/502 422/549 |
| 2007/0269355 A1* | 11/2007 | Malmqvist | ............ | B01F 5/0685 422/224 |
| 2008/0269076 A1* | 10/2008 | Ermakov | ............. | B01J 19/0046 506/32 |
| 2008/0314454 A1* | 12/2008 | Delattre | ............... | B01J 19/0093 137/14 |
| 2009/0298067 A1 | 12/2009 | Irimia et al. | | |
| 2010/0041128 A1 | 2/2010 | Banes et al. | | |
| 2013/0089869 A1 | 4/2013 | Blobe et al. | | |
| 2013/0236879 A1 | 9/2013 | Berry et al. | | |
| 2014/0087412 A1 | 3/2014 | Fouras et al. | | |
| 2014/0093891 A1* | 4/2014 | Kern | .................... | B01L 3/5025 435/7.72 |
| 2014/0274739 A1 | 9/2014 | Rinker et al. | | |
| 2017/0153217 A1* | 6/2017 | Johnston | ................ | G01N 33/18 |

OTHER PUBLICATIONS

Chen, et al., "Cardiac-like flow generator for long-term imaging of endothelial cell responses to circulatory pulsatile flow at microscale", Lab on a Chip 13(15), 2999-3007 (2013).
Lu, et al., "Microfluidic Shear Devices for Quantitative Analysis of Cell Adhesion", Anal Chem 76(18), 5257-5264 (2004).
Nagrath, et al., "Isolation of rare circulating tumour cells in cancer patients by microchip technology", Nature 450 (7173), 1235-1239 (2007).
Patent Cooperation Treaty, International Searching Authority, Search Report and Written Opinion for PCT/US2015/058255, 9 pages, dated Feb. 15, 2016.

* cited by examiner

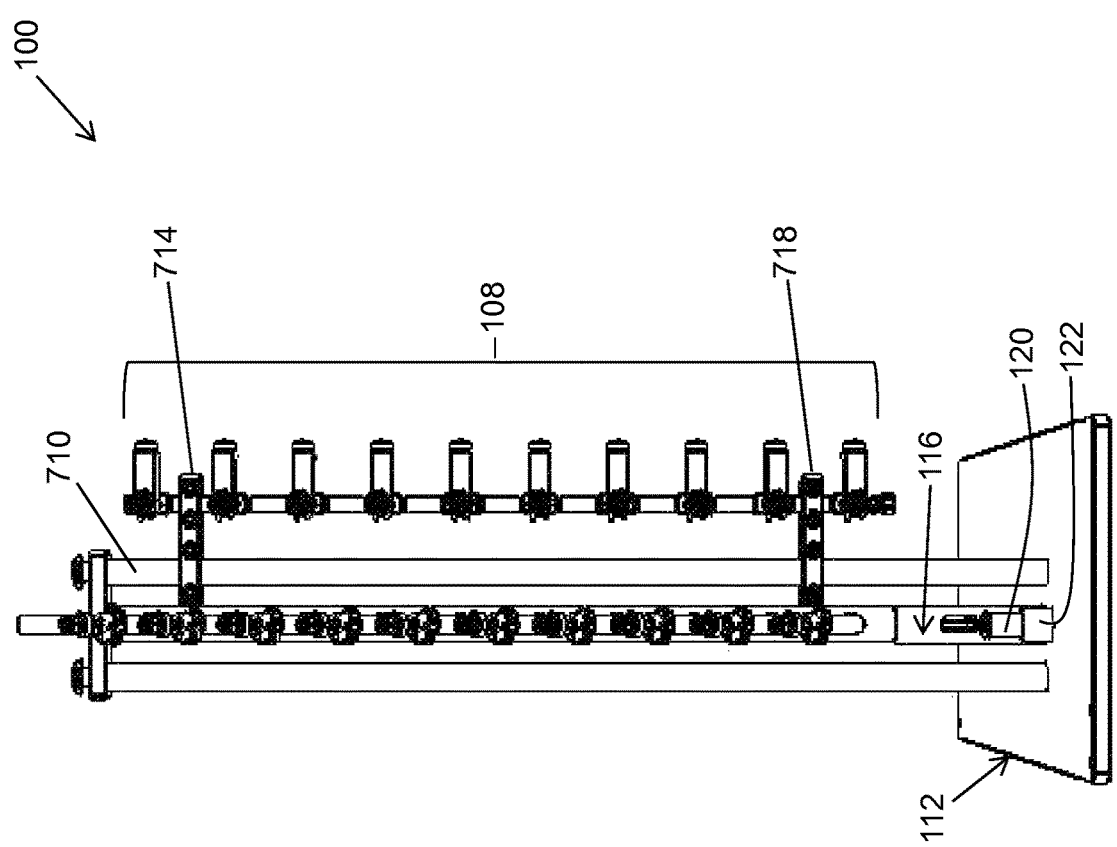

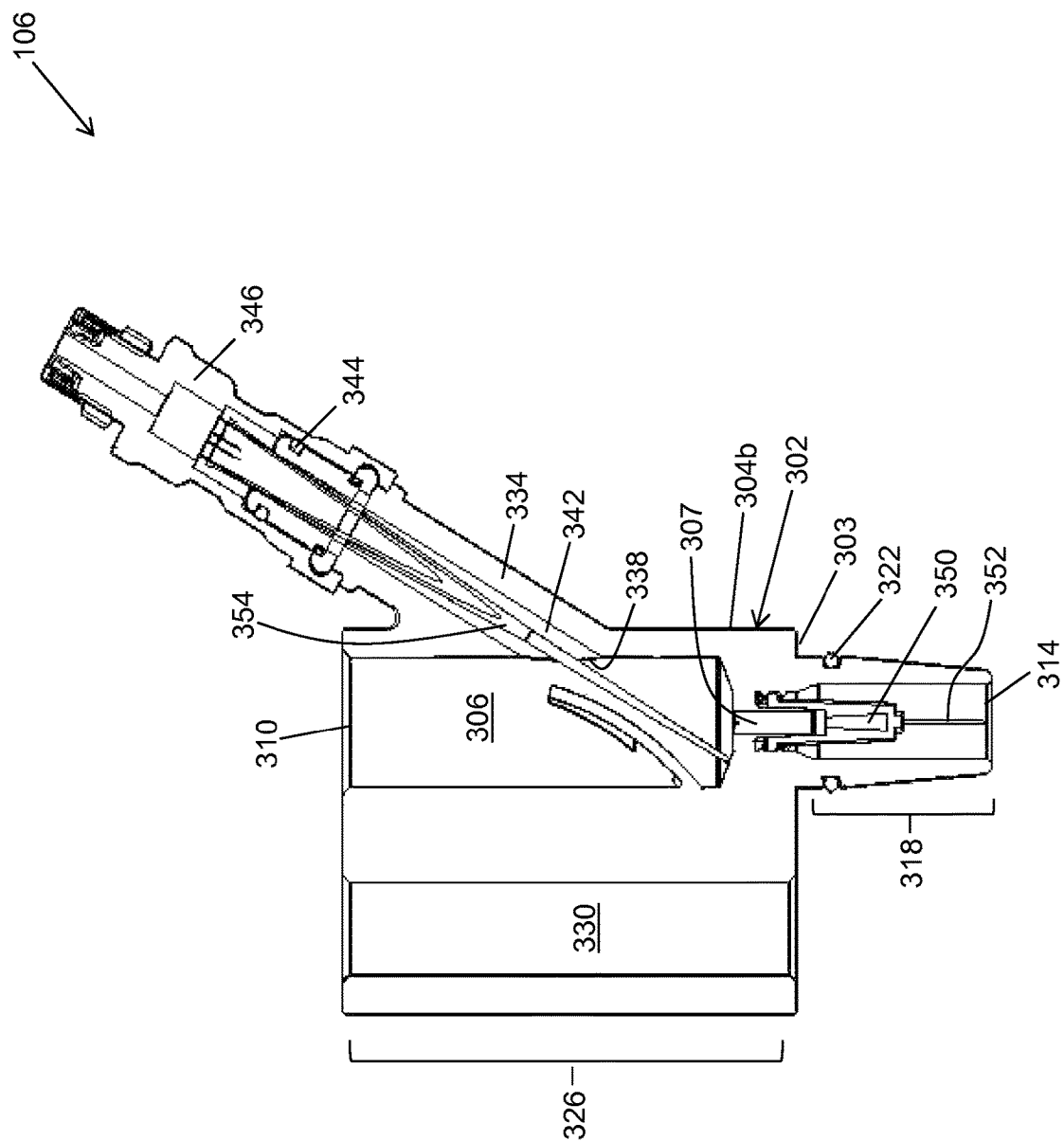

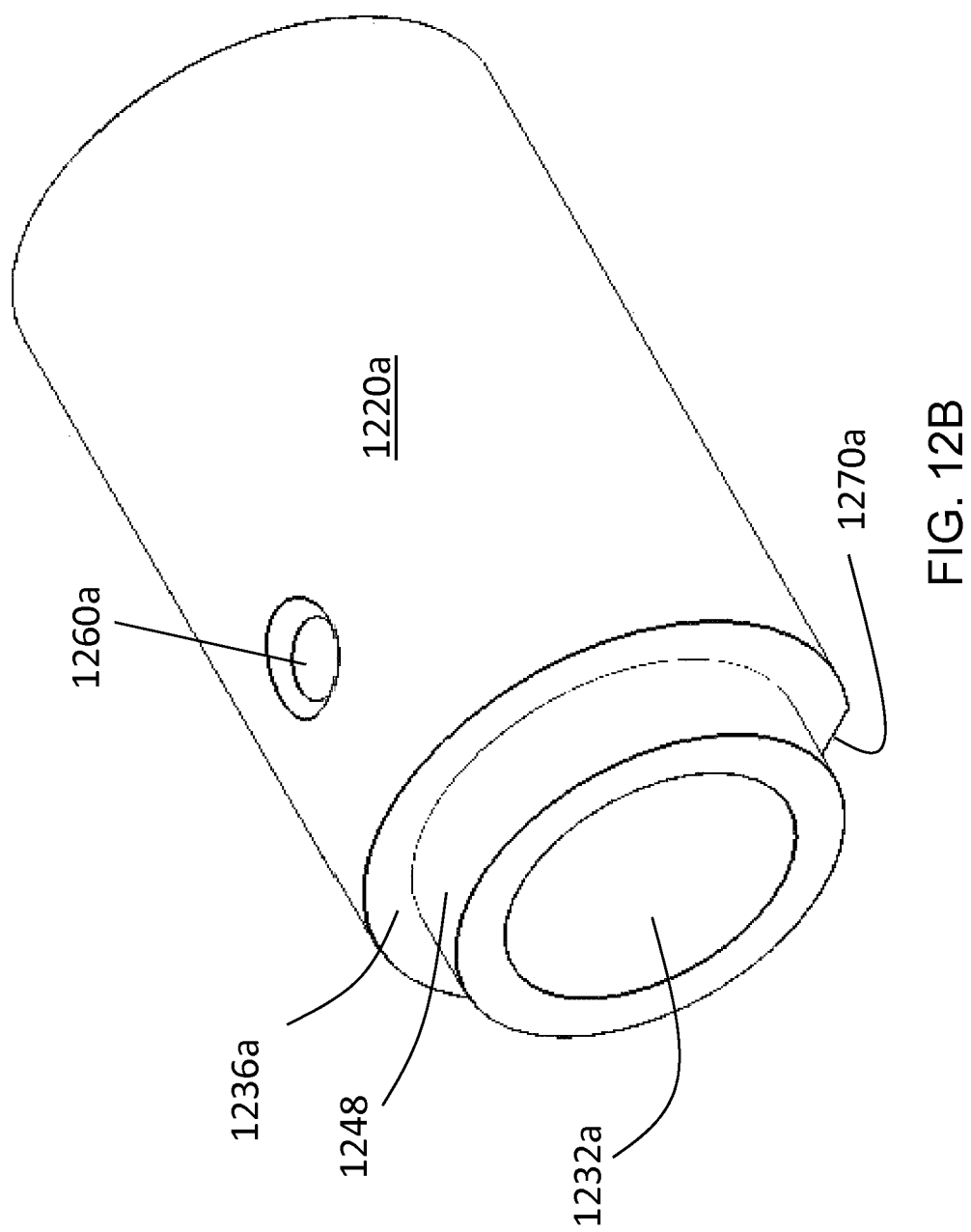

| passage (#) | t_start | t_end | delta_t | flow rate (µl/sec) | app. volume (µl) |
|---|---|---|---|---|---|
| 1 | 2.61 | 20.529 | 17.919 | 223.226743 | 4000 |
| 2 | 23.025 | 38.88 | 15.855 | 252.286345 | 4000 |
| 3 | 120.43 | 136.83 | 16.4 | 231.707317 | 3800 |
| 4 | 137.77 | 152.55 | 14.78 | 257.104195 | 3800 |
| 5 | 195.89 | 209.65 | 13.76 | 261.627907 | 3600 |
| 6 | 210.68 | 224.98 | 14.3 | 251.748252 | 3600 |
| 7 | 260.15 | 273.42 | 13.27 | 256.217031 | 3400 |
| 8 | 275.46 | 290.24 | 14.78 | 230.040595 | 3400 |
| 9 | 334.17 | 346.88 | 12.71 | 251.77026 | 3200 |
| 10 | 348.96 | 363.77 | 14.81 | 216.070223 | 3200 |
| avg | | | | 243.179887 | |

FIG. 18

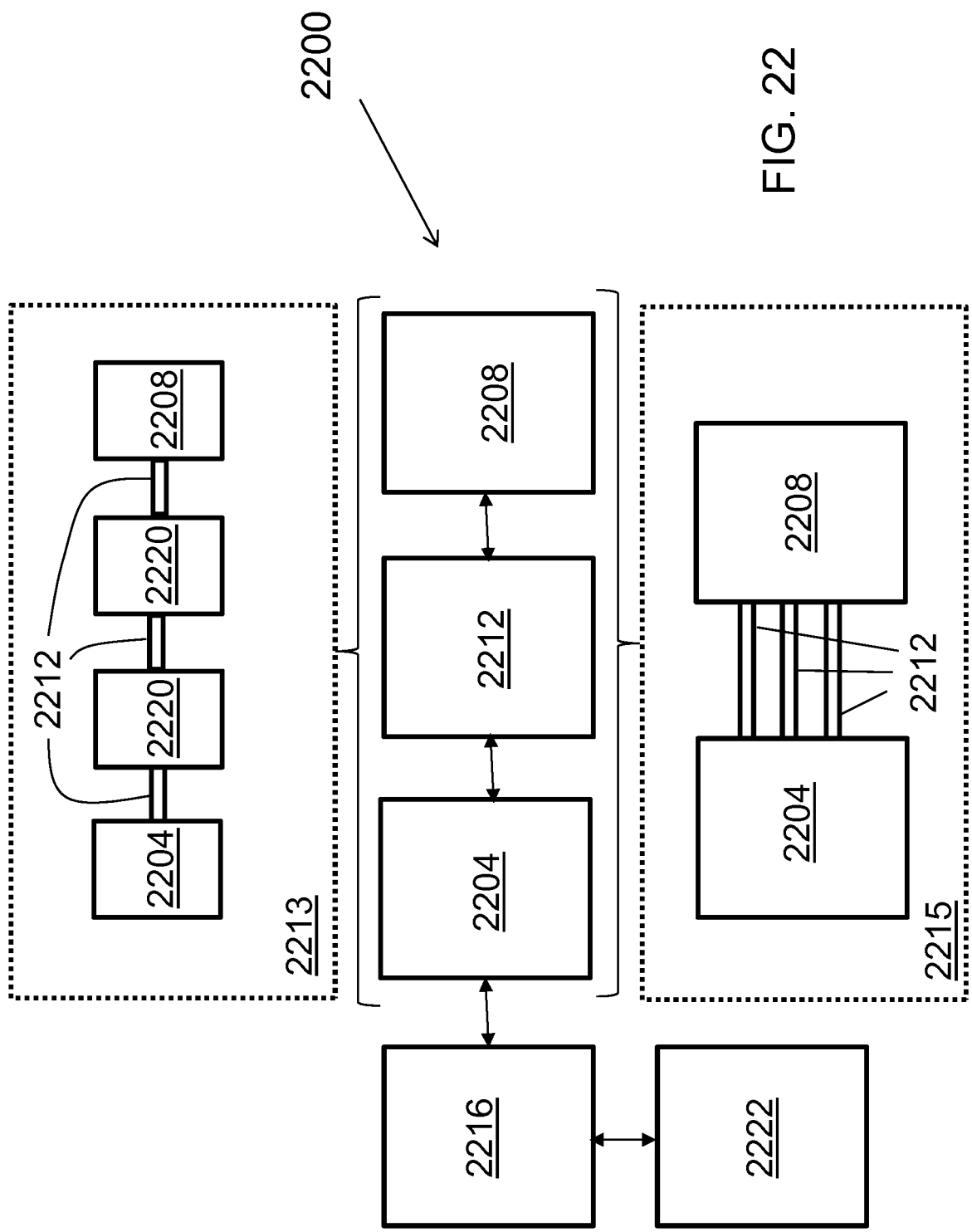

FLUID HANDLING SYSTEMS FOR APPLICATION OF FLUID SHEAR STRESS TO A FLUID SAMPLE

CROSS-REFERENCE TO RELATED APPLICATIONS

The present application claims priority to U.S. Provisional Patent Application No. 62/073,142 that was filed Oct. 31, 2014, the entire contents of which are hereby incorporated by reference.

BACKGROUND

It has been demonstrated that cancerous cells are more resistant to fluid shear stress than normal (non-cancerous) cells. (See, Barnes J. M., Nauseef, J. T., Henry, M. D. (2012) Resistance to Fluid Shear Stress Is a Conserved Biophysical Property of Malignant Cells. PLoS ONE 7(12): e50973. doi:10.1371/journal.pone.0050973.) In particular, the repeated exposure of fluid samples comprising both cancerous and normal cells to a fluid shear stress has been found to impart a selective resistance to the fluid shear stress to the cancerous cells and to selectively kill the non-cancerous cells, thereby providing a fluid sample enriched in the cancerous cells. (Id.) The concentration and isolation of fluid shear stress-resistant cancerous cells allows for further characterization of the cancerous cells, ultimately leading to improved clinical diagnostic tests for prognostic and therapeutic applications.

SUMMARY

Fluid handling systems for applying a plurality of pulses of fluid shear stress to a fluid sample are provided. Related methods for the fluid handling systems are also provided.

In a first aspect, a first embodiment of a fluid handling system for applying a plurality of pulses of fluid shear stress to a fluid sample is provided comprising a first sample chamber; a second sample chamber; a plurality of conduits mounted between and in fluid communication with the first sample chamber and the second sample chamber, each conduit having an inner diameter of less than about 1000 µm; and a force delivery system mounted to the first sample chamber and configured to apply a force sufficient to push the fluid sample at a substantially constant flow rate from the first sample chamber through each of the conduits to the second sample chamber. The dimensions of each conduit may be substantially the same. The fluid handling system may further comprise a control system operably coupled to the force delivery system to repeatedly apply the force, each application of force having a selected magnitude and a selected duration time.

In the first embodiment, the conduits may be arranged in series and are each separated by an additional sample chamber.

In some such embodiments, the force delivery system may be a gas delivery system configured to deliver gas to pressurize the sample chambers to a selected pressure, the gas delivery system comprising a plurality of gas valves, each gas valve in fluid communication with an associated sample chamber.

In some such embodiments, the fluid handling system may further comprise a syringe stack comprising a plurality of stackable syringe assemblies, each stackable syringe assembly in fluid communication with an adjacent stackable syringe assembly, each stackable syringe assembly comprising: a syringe body defining a sample chamber; a gas inlet port in fluid communication with the sample chamber; and a conduit through which the fluid sample may pass from the sample chamber into an adjacent sample chamber of the adjacent stackable syringe assembly; wherein the syringe stack comprises the first sample chamber, the second sample chamber, the plurality of conduits and the additional sample chambers, and wherein each gas valve is in fluid communication with an associated stackable syringe assembly via an associated gas inlet port.

Alternatively, in the first embodiment, the conduits may be arranged substantially parallel to one another.

In some such embodiments, the force delivery system may be a linear drive assembly configured to translate a first surface in a first direction towards the fluid sample in the first sample chamber at a selected speed over a selected distance and to translate a second surface in an opposing, second direction towards the fluid sample at the selected speed over the selected distance in the second sample chamber.

In some such embodiments, the fluid handling system may further comprise a moveable sample receptacle assembly comprising a first syringe body defining the first sample chamber, a second syringe body defining the second sample chamber and the plurality of substantially parallel conduits mounted between the first syringe body and the second syringe body; a first fixed piston mounted in a first bore of the first syringe body; and a second fixed piston mounted in a second bore of the second syringe body; wherein the linear drive assembly is configured to translate the moveable sample receptacle assembly back and forth along the longitudinal axis of the sample receptacle assembly.

In a second embodiment, a fluid handling system for applying a plurality of pulses of fluid shear stress to a fluid sample comprises a first sample chamber; a second sample chamber; a plurality of conduits mounted between and in fluid communication with the first sample chamber and the second sample chamber, wherein the conduits are arranged in series and are each separated by an additional sample chamber; and a gas delivery system mounted to the first sample chamber, the gas delivery system configured to deliver gas to pressurize the sample chambers to a selected pressure, the gas delivery system comprising a plurality of gas valves, each gas valve in fluid communication with an associated sample chamber. Each conduit may have an inner diameter of less than about 1000 µm. The dimensions of each conduit may be substantially the same.

In the second embodiment, the fluid handling system may further comprise: a syringe stack comprising a plurality of stackable syringe assemblies, each stackable syringe assembly in fluid communication with an adjacent stackable syringe assembly, each stackable syringe assembly comprising a syringe body defining a sample chamber; a gas inlet port in fluid communication with the sample chamber; and a conduit through which the fluid sample may pass from the sample chamber into an adjacent sample chamber of the adjacent stackable syringe assembly; wherein the syringe stack comprises the first sample chamber, the second sample chamber, the plurality of conduits and the additional sample chambers, and wherein each gas valve is in fluid communication with an associated stackable syringe assembly via an associated gas inlet port.

In some such embodiments, the syringe body may further comprise a bottom end portion configured such that the bottom end portion is insertable into a top opening of an adjacent syringe body of the adjacent stackable syringe assembly to form a pressure-tight seal.

In some such embodiments, the stackable syringe assembly may further comprise an arm defining a bore through which fluid may pass, the arm mounted to the syringe body and extending from the gas inlet port, the arm configured to mount to a gas line coupler and to a receptacle configured to collect a portion of the fluid sample. The receptacle may be a pipette tip insertably mounted in the bore.

In some such embodiments, the syringe body may comprise a partition assembly mounted in the sample chamber and configured to reduce foaming of the fluid sample as it passes into the sample chamber en route to the conduit. The partition assembly may comprise a central portion mounted to a side wall of the syringe body at a bottom end of the central portion, the central portion extending upwardly such that a top end of the central portion is positioned within a substantially central location within the sample chamber, and first and second lateral portions mounted to opposite sides of the top end of the central portion, wherein the central portion and first and second lateral portions define gaps through which the fluid sample may pass.

In some such embodiments, the gas delivery system may comprise a gas valve stack, the gas valve stack comprising a plurality of gas valve assemblies, the plurality of gas valve assemblies comprising the plurality of gas valves. The plurality of gas valve assemblies may comprise three-way solenoid valves.

In some such embodiments, the fluid handling system may further comprise a support assembly mounted to the syringe stack and configured to position the syringe stack vertically.

In the second embodiment, the fluid handling system may further comprise a control system operably coupled to the gas delivery system and configured to sequentially deliver gas to each sample chamber at the selected pressure for a selected duration time to sequentially pass the fluid sample through each conduit. The control system may be configured to perform operations comprising (a) pressurizing the first sample chamber with gas to the selected pressure; (b) maintaining the pressurization at the selected pressure until an indicator indicates the substantially complete delivery of the fluid sample through a first conduit in the plurality of conduits into an adjacent sample chamber; (c) venting the first sample chamber for a selected hold time; and (d) repeating steps (a)-(c) such that the fluid sample passes through each conduit in the plurality of conduits.

A method of using the fluid handling system according to the second embodiment may comprise (a) pressurizing the first sample chamber comprising the fluid sample with gas to the selected pressure; (b) maintaining the pressurization at the selected pressure until an indicator indicates the substantially complete delivery of the fluid sample through a first conduit in the plurality of conduits into an adjacent sample chamber; (c) venting the first sample chamber for a selected hold time; and (d) repeating steps (a)-(c) such that the fluid sample passes through each conduit in the plurality of conduits. The method may further comprise withdrawing a portion of the fluid sample from the adjacent sample chamber during the selected hold time.

In another aspect, a stackable syringe assembly for use in a fluid handling system is provided comprising a syringe body defining a sample chamber, the syringe body comprising a bottom end portion configured such that the bottom end portion is insertable into a top opening of an adjacent syringe body of an adjacent stackable syringe assembly to form a pressure-tight seal; a gas inlet port in fluid communication with the sample chamber; and a conduit through which the fluid sample may pass from the sample chamber into an adjacent sample chamber of the adjacent stackable syringe assembly.

In a third embodiment, a fluid handling system for applying a plurality of pulses of fluid shear stress to a fluid sample is provided comprising: a first sample chamber; a second sample chamber; a plurality of substantially parallel conduits mounted between and in fluid communication with the first sample chamber and the second sample chamber; and a linear drive assembly mounted to the first sample chamber and configured to translate a first surface in a first direction towards the fluid sample in the first sample chamber at a selected speed over a selected distance and to translate a second surface in an opposing, second direction towards the fluid sample in the second sample chamber at the selected speed over the selected distance.

In the second embodiment, the fluid handling system may further comprise: a moveable sample receptacle assembly comprising a first syringe body defining the first sample chamber, a second syringe body defining the second sample chamber and the plurality of substantially parallel conduits mounted between the first syringe body and the second syringe body; a first fixed piston mounted in a first bore of the first syringe body; and a second fixed piston mounted in a second bore of the second syringe body; wherein the linear drive assembly is configured to translate the moveable sample receptacle assembly back and forth along the longitudinal axis of the sample receptacle assembly. The conduits may each have an inner diameter of less than about 1000 µm. The dimensions of each conduit may be substantially the same.

In some such embodiments, the plurality of substantially parallel conduits may be embedded in a conduit holding block and arranged in an array.

In some such embodiments, the first fixed piston and the second fixed piston may each be provided by a syringe plunger.

In some such embodiments, the first fixed piston and the second fixed piston may each be adjustably mounted to the linear drive assembly via a first piston anchor assembly and a second piston anchor assembly, respectively.

In some such embodiments, the fluid handling system may further comprise a control system operably coupled to the linear drive assembly and configured to translate the sample receptacle assembly back and forth over the selected distance between an initial position and a selected position at the selected speed to repeatedly pass the fluid sample through the plurality of substantially parallel conduits. The control system may configured to perform operations comprising: (a) translating the sample receptacle assembly from the initial position to the selected position in the first direction along the longitudinal axis at the selected speed to transfer the fluid sample from the first sample chamber to the second sample chamber through the plurality of substantially parallel conduits; (b) holding the sample receptacle assembly at the selected position for a selected hold time; (c) translating the sample receptacle assembly from the selected position to the initial position in the opposing direction along the longitudinal axis at the selected speed to transfer the fluid sample from the second sample chamber to the first sample chamber through the plurality of substantially parallel conduits; (d) holding the sample receptacle assembly at the initial position for the selected hold time; and (e) repeating steps (a)-(d) such that the fluid sample passes through the plurality of substantially parallel conduits a selected number of times.

A method of using the fluid handling system according to the third embodiment may comprise (a) translating the sample receptacle assembly comprising the fluid sample in the first sample chamber from an initial position to a selected position in the first direction along the longitudinal axis at the selected speed to transfer the fluid sample from the first sample chamber to the second sample chamber through the plurality of substantially parallel conduits; (b) holding the sample receptacle assembly at the selected position for a selected hold time; (c) translating the sample receptacle assembly from the selected position to the initial position in the opposing direction along the longitudinal axis at the selected speed to transfer the fluid sample from the second sample chamber to the first sample chamber through the plurality of substantially parallel conduits; and (d) holding the sample receptacle assembly at the initial position for the selected hold time. The method may further comprise repeating steps (a)-(b) or steps (a)-(d) such that the fluid sample passes through the plurality of substantially parallel conduits a selected number of times. The method may further comprise withdrawing a portion of the fluid sample from one of the first or second sample chambers during one of the selected hold times.

Other principal features and advantages of the invention will become apparent to those skilled in the art upon review of the following drawings, the detailed description, and the appended claims.

BRIEF DESCRIPTION OF THE DRAWINGS

Exemplary embodiments of the invention will hereafter be described with reference to the accompanying drawings, wherein like numerals denote like elements.

FIG. 1C shows a side view of the fluid handling system.

FIG. 3B shows a front cross-sectional view of the stackable syringe assembly.

FIG. 12B shows a perspective view of a first syringe body of the sample receptacle assembly.

FIG. 18 shows display output that may be provided by or calculated from output signals provided by the control system of the fluid handling system during the exemplary set of operations of FIG. 17.

FIG. 22 shows a block diagram of a fluid handling system according to an exemplary embodiment.

DETAILED DESCRIPTION

Figure 1A:
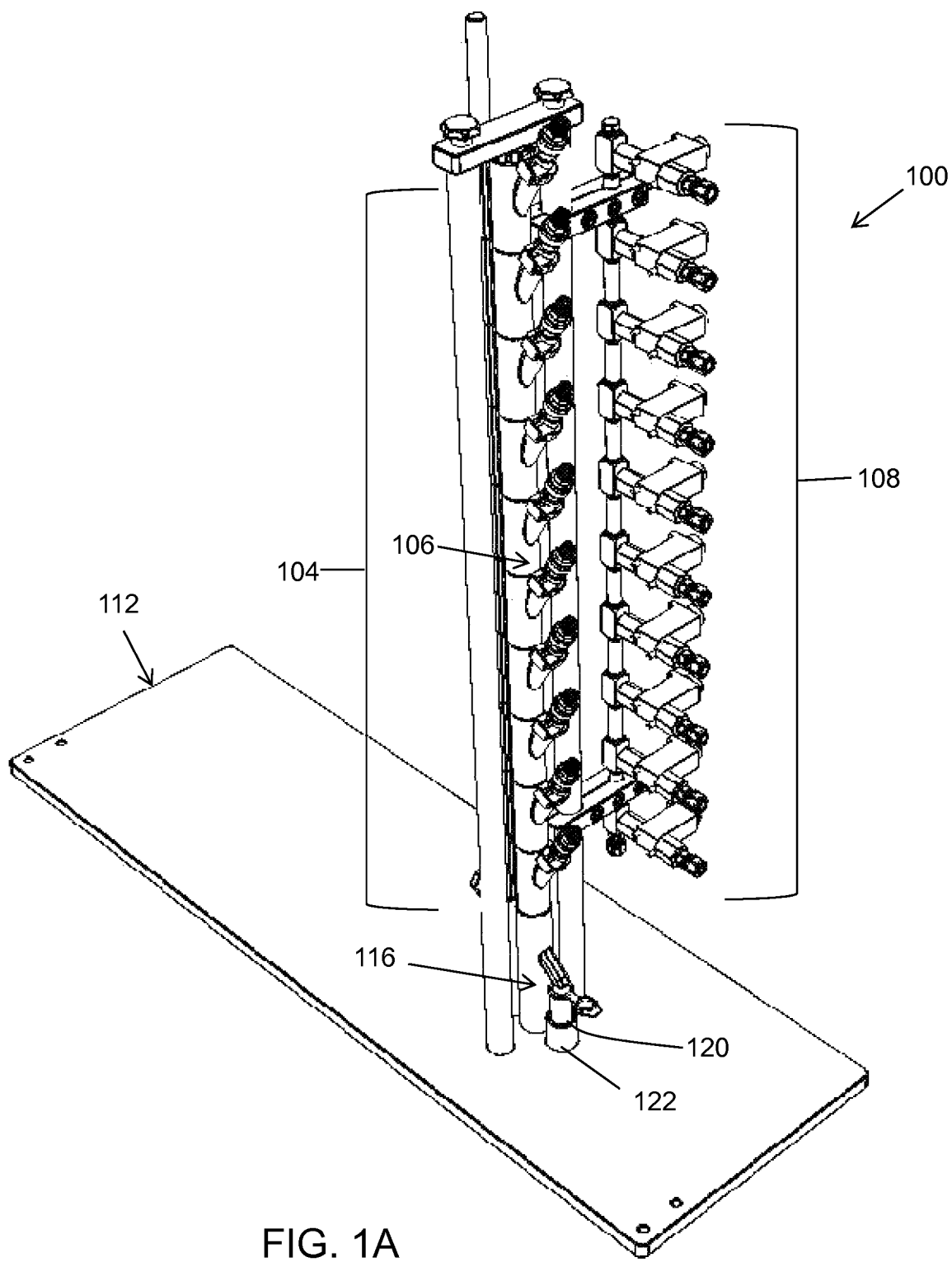
FIG. 1A shows a perspective view a fluid handling system based on gas pressure according to an exemplary embodiment.

As used herein, the term "mount" includes join, unite, connect, couple, associate, insert, hang, hold, affix, attach, fasten, bind, paste, secure, bolt, screw, rivet, solder, weld, glue, form over, form in, layer, mold, rest on, rest against, abut, and other like terms. The phrases "mounted on", "mounted to", and equivalent phrases indicate any interior or exterior portion of the element referenced. These phrases also encompass direct mounting (in which the referenced elements are in direct contact) and indirect mounting (in which the referenced elements are not in direct contact, but are connected through an intermediate element). Elements referenced or shown as mounted to each other herein may further be integrally formed together, for example, using a molding or thermoforming process as understood by a person of skill in the art. As a result, elements described herein as being mounted to each other need not be discrete structural elements. The elements may be mounted permanently, removably, or releasably unless specified otherwise.

Use of directional terms, such as top, bottom, right, left, front, back, etc. are merely intended to facilitate reference to various surfaces that form components of the devices referenced herein and are not intended to be limiting in any manner.

Fluid handling systems for applying a plurality of pulses of fluid shear stress to a fluid sample are provided. By "pulse," it is meant that the fluid sample is exposed to a selected magnitude of fluid shear stress for a selected duration of time. As described in U.S. Pat. Pub. No. 20140038231, which is hereby incorporated by reference in its entirety, fluid sample being passed through a conduit experiences a range of magnitudes of fluid shear stress from zero to a maximum value, with the magnitude depending upon its position relative to the longitudinal axis of the conduit. The "selected magnitude of fluid shear stress" may refer to the shear stress calculated at the wall of the conduit through which the fluid sample is passed, calculated using Poiseuille's equation, $\tau=4Q\eta/\pi r^3$, wherein $\tau$ is shear stress; Q is flow rate; $\eta$ is the viscosity of the medium; and r is the radius of the conduit. A pulse program may be characterized by the number of pulses, the magnitude of fluid shear stress for each pulse, the duration of time for each pulse and the hold time between pulses. The fluid handling systems may be used to apply a variety of different pulse programs, including those disclosed in U.S. Pat. Pub. No. 20140038231.

Similarly, the fluid samples may include the preparations disclosed in U.S. Pat. Pub. No. 20140038231. Thus, the fluid samples may include cancerous cells, e.g., an in vitro preparation of cancerous cells or a blood sample from a patient. The repeated exposure of such fluid samples to fluid shear stress via the disclosed fluid handling systems imparts an increased resistance to fluid shear stress to the cancerous cells and provides a population of fluid shear stress-resistant cancerous cells in the fluid samples. Since normal cells (non-cancerous cells) do not experience an increase in their resistance to fluid shear stress or experience a lower increase than the cancerous cells, the normal cells may be selectively killed by the application of fluid shear stress provided by the disclosed fluid handling systems. Thus, the fluid handling systems may be used to carry out the methods disclosed in U.S. Pat. Pub. No. 20140038231, including methods for purifying/concentrating fluid samples comprising cancerous cells. Such methods are useful as part of clinical diagnostic tests for prognostic applications to assess the likely health outcome for a patient having, or at risk of developing, cancer or metastases and therapeutic applications to assess the effect of a treatment program for such a patient.

The fluid handling systems are also applicable to the field of cytologic pathology in which cancer cells may be admixed with a variety of non-cancer cells. This includes, but is not limited to, fine needle aspirates and fluid specimens including urine, pleural effusion, peritoneal fluid, and cerebrospinal fluid. The fluid handling systems may be used to enrich the relative abundance of cancer to non-cancer cells in the sample preparation, prior to a variety of subsequent analytic procedures. This facilitates standard cytologic workup as well as molecular analyses including genetic analysis and immunohistochemical staining.

As shown schematically in FIG. 22, a fluid handling system 2200 for applying a plurality of pulses of fluid shear stress to a fluid sample may include a first sample chamber 2204, a second sample chamber 2208, a plurality of conduits 2212 in between and in fluid communication with the first sample chamber 2204 and the second sample chamber 2208, and a force delivery assembly 2216 configured to apply a force sufficient to push the fluid sample, e.g., at a substantially constant flow rate, from the first sample chamber 2204 through each of the conduits in the plurality of conduits 2212 to the second sample chamber 2208. In some embodiments of the fluid handling system 2200 (shown by the dotted box 2213), the conduits in the plurality of conduits 2212 may be arranged in series and may be separated by additional sample chambers 2220. In some embodiments of the fluid handling system 2200 (shown by the dotted box 2213), the conduits in the plurality of conduits 2212 may be arranged substantially parallel to one another.

As discussed above, passage of the fluid sample through the conduits results in exposure of the fluid sample to a range of magnitudes of fluid shear stress from zero to a maximum value, in which the magnitude of the fluid shear stress depends upon the flow rate achieved by the application of the force (as well as parameters of the conduit and the fluid sample itself). Thus, the magnitude of the force may be selected to provide a selected flow rate and thus, a selected magnitude of fluid shear stress. The selected magnitude of fluid shear stress may vary over a wide range, including high and/or supra-physiologic levels. In some embodiments, the selected magnitude of fluid shear stress is in the range of from about 300 to about 6500 dyn/cm$^2$. In some embodiments, the selected magnitude of fluid shear stress is at least 500 dyn/cm$^2$, at least 1000 dyn/cm$^2$, at least 3500 dyn/cm$^2$, or at least 6000 dyn/cm$^2$. Other selected magnitudes of fluid shear stress may be used, including those disclosed in U.S. Pat. Pub. No. 20140038231.

As shown in FIG. 22, the fluid handling system 2200 may further include a control system 2222 operably coupled to the force delivery assembly 2216 to control and to automate the application of the force. For example, the control system 2222 may be used to repeatedly apply a force of a selected magnitude for a selected duration time.

In some embodiments of the fluid handling system 2200, the force delivery assembly 2216 may be a gas delivery system, e.g., the force to push the fluid sample through the conduits 2212 is generated by exposing the fluid sample to a pressurized gas. In some embodiments of the fluid handling system 2200, the force delivery assembly 2216 may be a linear drive assembly, e.g., the force to push the fluid sample through the conduits 2212 is generated by the mechanical translation of a surface against the fluid sample contained in the sample chambers 2204, 2208. These embodiments are described in separate sections immediately below. Other types of force delivery assemblies may be used, including those based on the use of centripetal force, gravitational force and shear force.

Fluid Handling System Based on Gas Pressure

Figure 1B:
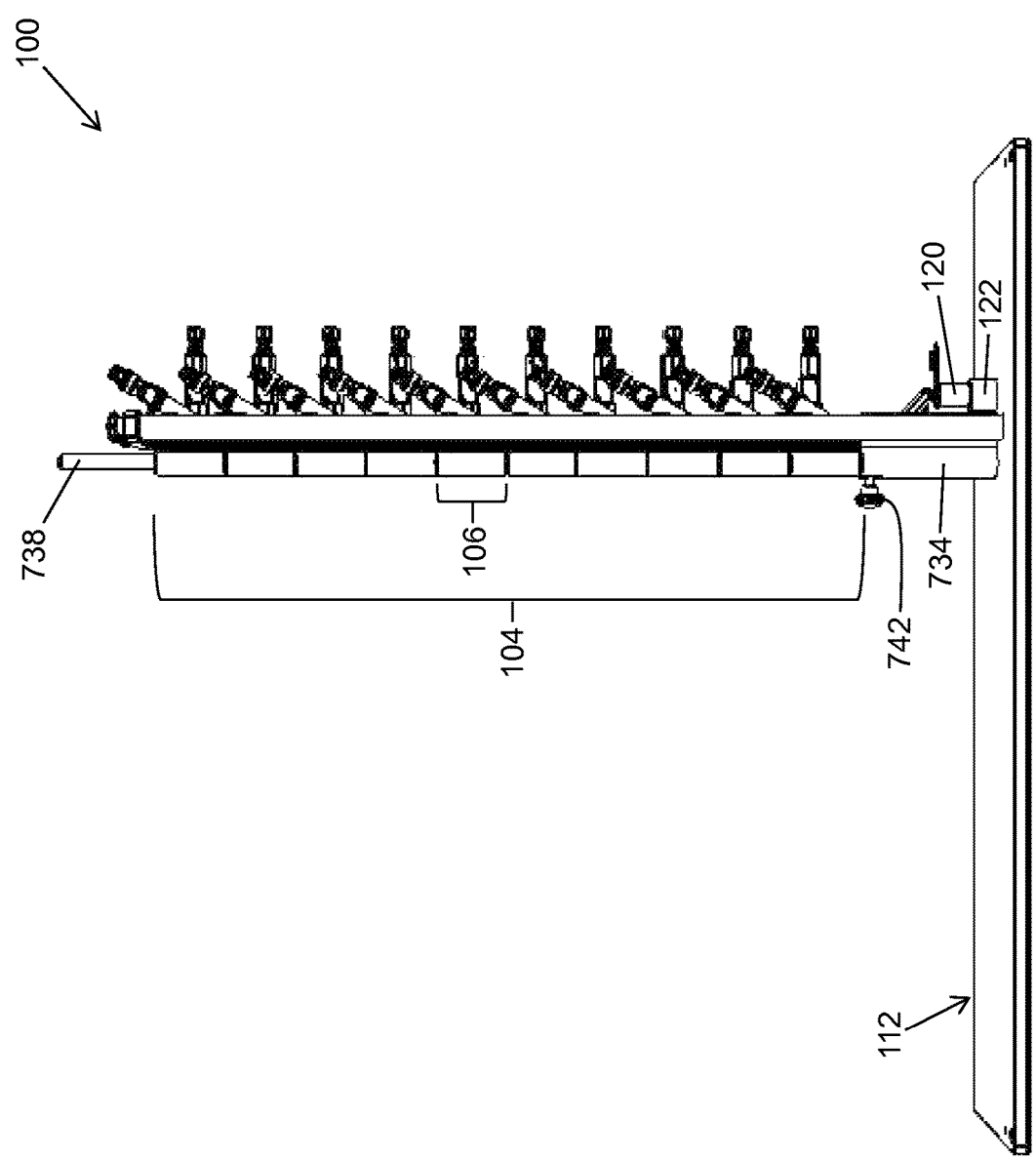
FIG. 1B shows a front view of the fluid handling system.

With reference to FIG. 1, a fluid handling system 100 for applying a plurality of pulses of fluid shear stress to a fluid sample using gas pressure is shown in accordance with an exemplary embodiment. FIG. 1A shows a perspective view of the fluid handling system 100. FIG. 1B shows a front view of the fluid handling system 100. FIG. 1C shows a side view of the fluid handling system 100. The fluid handling system 100 may include a syringe stack 104 which may include a plurality of stackable syringe assemblies (one of which is labeled 106), a gas delivery system which may include a gas valve stack 108, and a support assembly 112. The fluid handling system 100 may include fewer or additional components as compared to those shown in FIG. 1.

Figure 2:
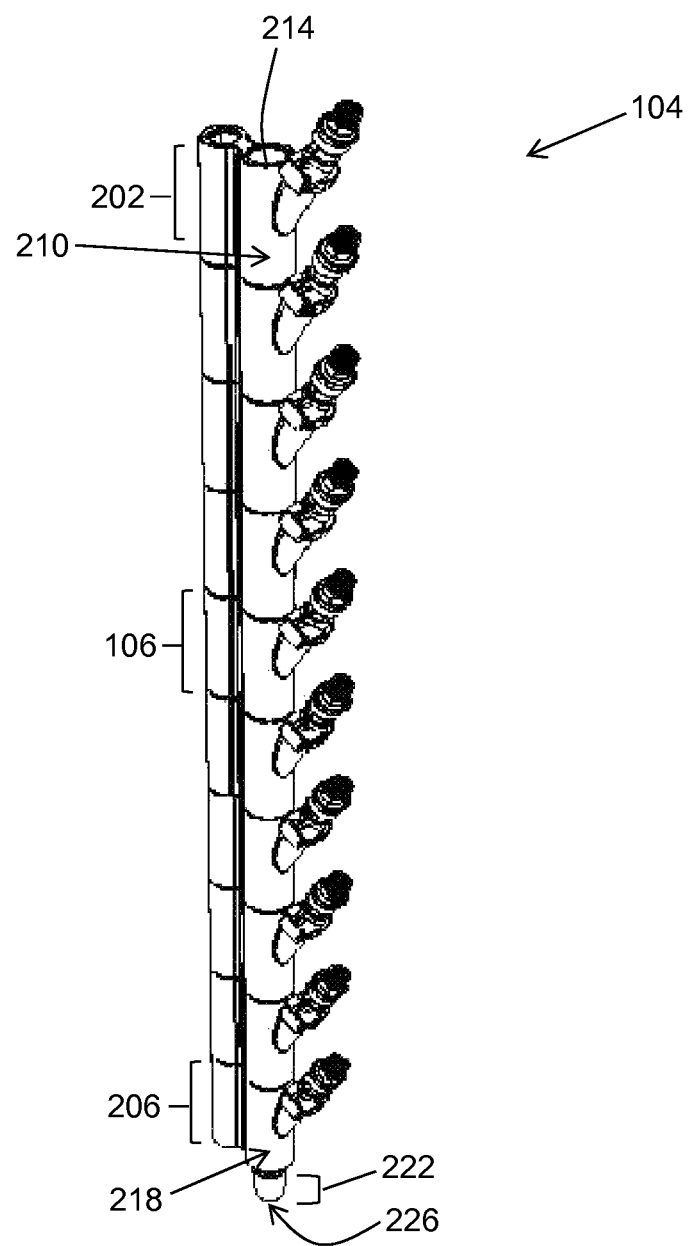
FIG. 2 shows a perspective view of a syringe stack of the fluid handling system of FIG. 1.

FIG. 2 shows a perspective view of the syringe stack 104 of the fluid handling system 100. The syringe stack 104 may include a plurality of stackable syringe assemblies (three of which are labeled 202, 106 and 206). Each stackable syringe assembly is mounted to, and is in fluid communication with, one or more neighboring stackable syringe assembly(ies) to form the syringe stack 104. Different numbers of stackable syringe assemblies may be used, depending upon the number of pulses fluid shear stress to be applied to the fluid sample. Various configurations for a stackable syringe assembly may be used which are capable of retaining the fluid sample within a sample chamber and of allowing the transfer of the fluid sample from the sample chamber through a conduit into an adjacent sample chamber of an adjacent stackable syringe assembly.

In the exemplary embodiment, an uppermost stackable syringe assembly 202 may include a syringe body 210. A bottom wall (not shown) of the syringe body 210 and side walls extending from the bottom wall define a uppermost sample chamber (not shown) which is accessible via a top opening 214 at a top end of the syringe body 210. Each stackable syringe assembly may be similarly configured. A bottommost stackable syringe assembly 206 may also include a syringe body 218. A bottom end portion 222 extends from a bottom wall (not shown) of the syringe body 218. A bottommost sample chamber (not shown) of the bottommost stackable syringe assembly 206 is also accessible via a bottom opening 226 in the bottom end portion 218. Each stackable syringe assembly may be similarly configured.

Each stackable syringe assembly in the syringe stack 104 may include a bottom end portion configured as shown in FIG. 2 such that the bottom end portion may be inserted into a top opening of another stackable syringe assembly and may form a pressure-tight seal, i.e., a seal which is capable of maintaining a pressure in a sample chamber in a stackable syringe assembly of greater than atmospheric pressure (e.g., a pressure of at least 300 psig). An o-ring 322 (with reference to FIG. 3A) may be positioned around the perimeter of each bottom end portion of each stackable syringe assembly to facilitate formation of the pressure-tight seal.

The syringe stack 104 may be sealed via a cap configured to insert into the top opening 214 of the uppermost stackable syringe assembly 202 and to form another pressure-tight seal. The cap may include an o-ring on an end thereof to facilitate formation of the pressure-tight seal.

Figure 3A:
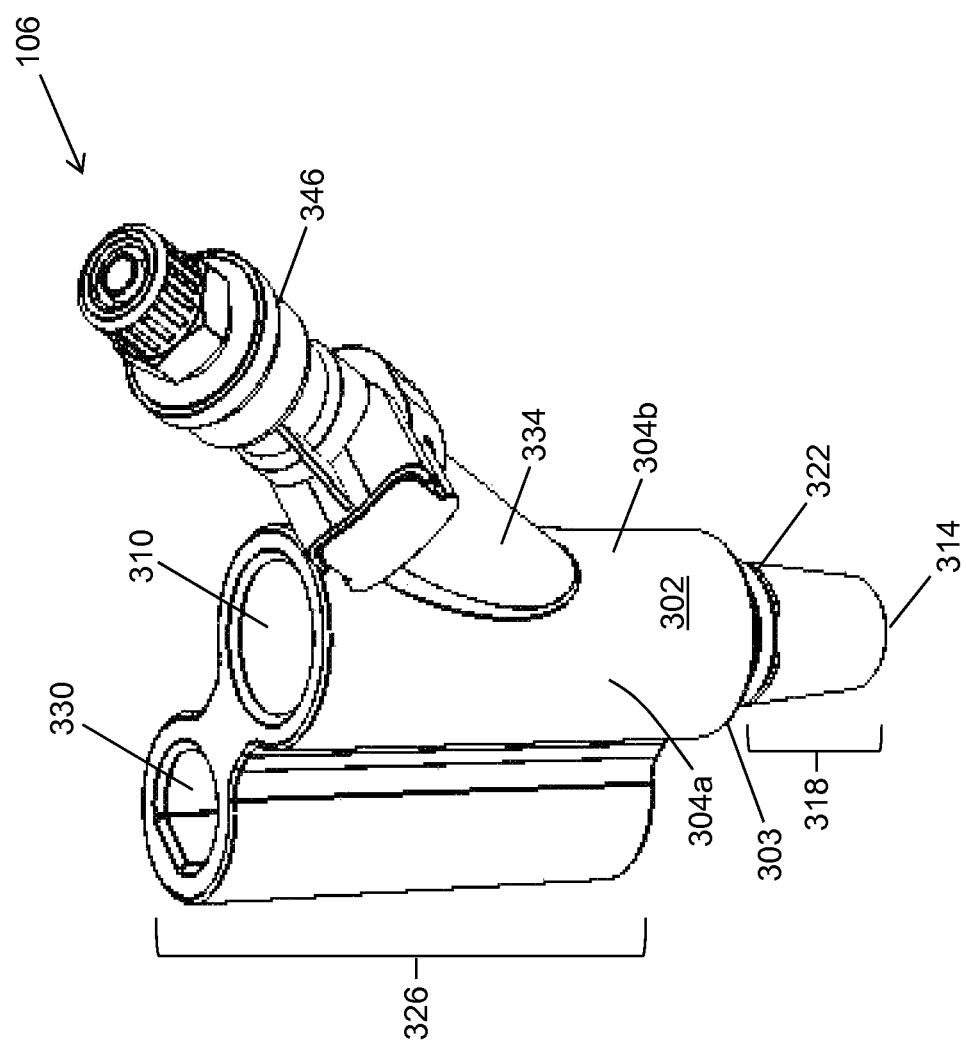
FIG. 3A shows a perspective view of a stackable syringe assembly of the syringe stack of FIG. 2.
Figure 3C:
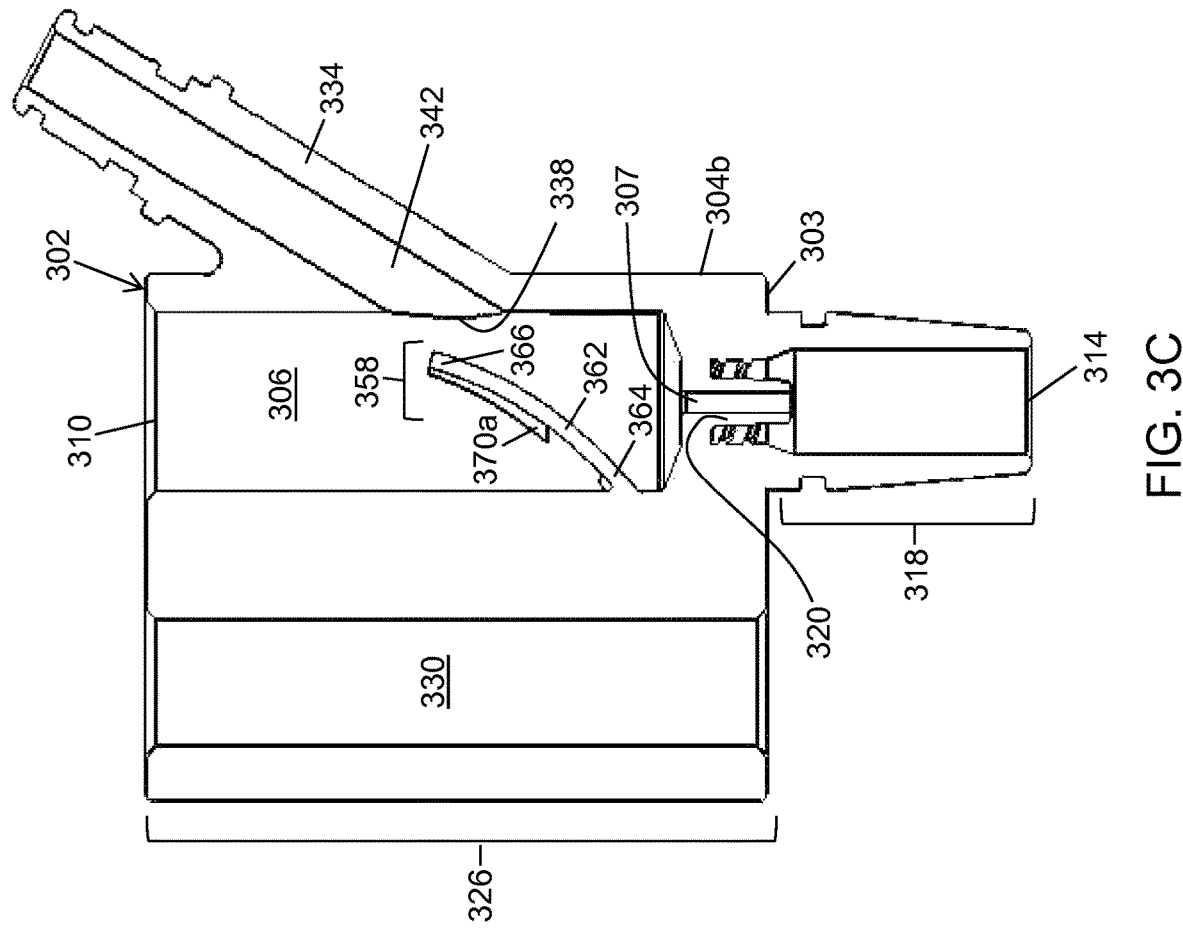
FIG. 3C shows a front cross-sectional view of a syringe body of the stackable syringe assembly of FIG. 3B.
Figure 3D:
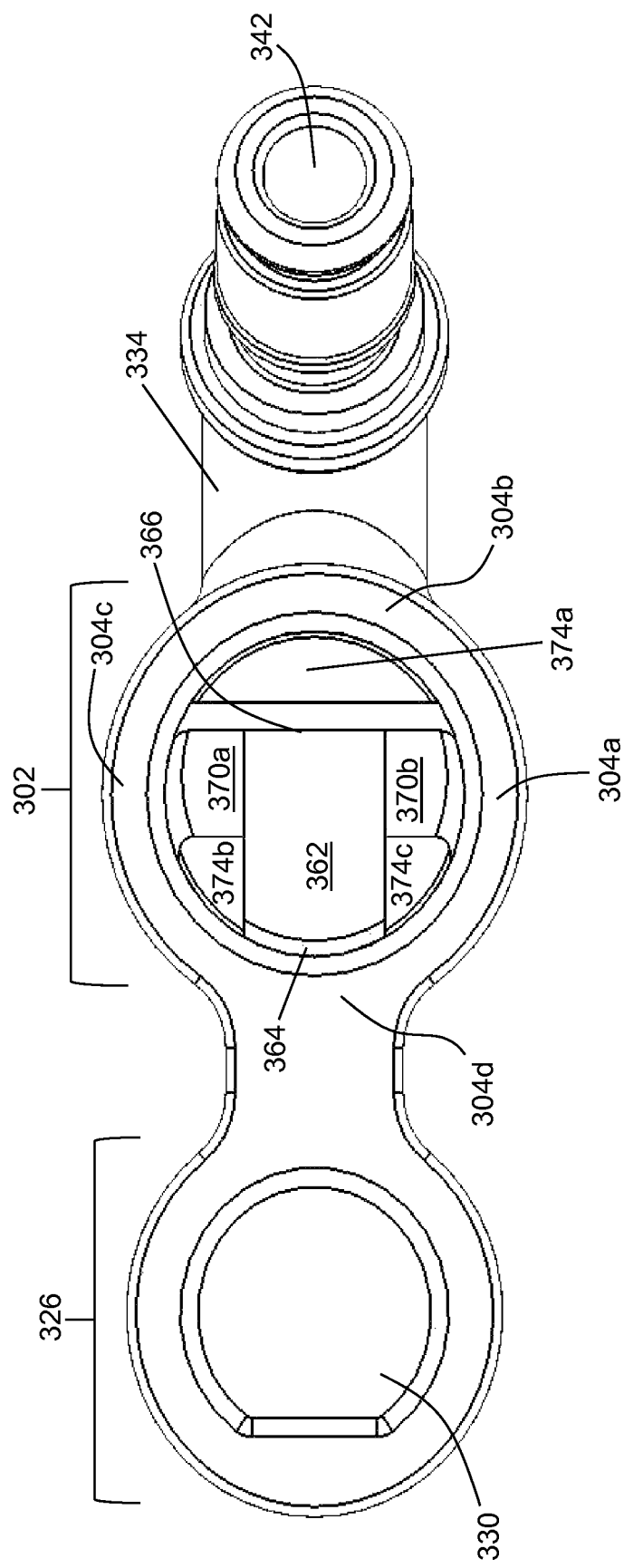
FIG. 3D shows a top down view of the syringe body.

FIG. 3 shows the stackable syringe assembly 106 (which is representative of each of the stackable syringe assemblies in the syringe stack 104) in more detail. FIG. 3A shows a perspective view of the stackable syringe assembly 106. FIG. 3B shows a front cross-sectional view of the stackable syringe assembly 106. FIG. 3C shows a front cross-sectional view of a syringe body 302 of the stackable syringe assembly 106. FIG. 3D shows a top down view of the syringe body 302 of the stackable syringe assembly 106.

The stackable syringe assembly 106 may include the syringe body 302. A bottom wall 303 of the syringe body 302 and side walls 304a-d extending from the bottom wall 303 define a sample chamber 306. A bottom end portion 318 extends from the bottom wall 303. The sample chamber 306 is accessible via a top opening 310 at a top end and via a bottom opening 314 in the bottom end portion 318. A bore 307 defined in the bottom wall 303 connects the sample chamber 306 to the hollow interior of the bottom end portion 318 and the bottom opening 314. As described above with respect to the bottommost stackable syringe assembly 206 (with reference to FIG. 2), the o-ring 322 may be positioned around the perimeter of the bottom end portion 318.

The stackable syringe assembly 106 may include a mounting member 326 mounted to the syringe body 302. The mounting member 326 may be configured to mount to an element of the support assembly 112 (e.g., a syringe stack support rod 738, with reference to FIGS. 1B and 7). Various configurations of the mounting member 326 may be used. In this exemplary embodiment, the mounting member 326 is a tube oriented substantially parallel to the longitudinal axis of the syringe body 302. The walls of the tube define a bore 330 through which the syringe stack support rod 738 may be inserted.

The stackable syringe assembly 106 may include an arm 334 extending from a gas inlet port 338 defined the side wall 304b of the syringe body 302. The walls of the arm 334 may define a bore 342 leading to the gas inlet port 338 at one end of the bore 342 and to a gas line coupler 346 at an opposing end of the bore 342. In this exemplary embodiment, the arm 334 is oriented substantially at a 45° angle with respect to the longitudinal axis of the syringe body 302, although other orientations may be used, e.g., 90° (see arm 2008 in FIG. 20). Another o-ring 344 may be positioned around the perimeter of the arm 334 to form another pressure-tight seal.

The dimensions of the syringe body 302 may depend upon the desired volume of the fluid sample to be held in the sample chamber 306. For example, the dimensions of the syringe body 302 may be that which is sufficient to hold about 10 mL, about 5 mL, etc. of the fluid sample.

The stackable syringe assembly 106 may include the gas line coupler 346 mounted to a top end of the arm 334. The gas line coupler 346 may be configured to connect a gas line mounted to the gas line coupler 346 at one end and an associated gas valve assembly 502 (with reference to FIGS. 5 and 6) at an opposing end such that a gas may be delivered to the sample chamber 306 of the syringe body 302. Commercially available gas line couplers may be used for the gas line coupler 346.

As shown in FIG. 3B, a pipette tip 354 may be temporarily inserted into the bore 342 of the arm 334. The pipette tip 354 may be used to withdraw a portion of the fluid sample from the sample chamber 306, as further described below. After the fluid sample is withdrawn, the pipette tip 354 may be removed.

The stackable syringe assembly 106 may include a conduit 352 in fluid communication with the sample chamber 306. As shown in the exemplary embodiment, the conduit 352 may be provided via a needle 350 which may be mounted on a threaded projection 320 which surrounds the bore 307 and extends into the hollow interior of the bottom end portion 318. The conduit 352 may be mounted and positioned such that it receives the fluid sample passing from the sample chamber 306 via the bore 307. Commercially available needles, e.g., hypodermic needles, may be used for the needle 350. The dimensions of the conduit 352 may be selected to provide a selected magnitude and selected duration time for the pulses of fluid shear stress to be applied (for a given pressure of gas applied to the fluid sample). The conduit may be micron-sized, e.g., the inner diameter of the conduit may be less than about 1000 µm, less than about 500 µm, less than about 200 µm, less than about 150 µm, etc. The conduits may have an inner diameter of about 150 µm and a length of about 1.27 cm. The conduits of the stackable syringe assemblies may be substantially uniform such that the dimensions of each conduit are substantially the same as the dimensions of another conduit in the plurality of stackable syringe assemblies. A variety of materials may be used for the conduits, e.g., stainless steel.

For clarity, FIGS. 3C-D are provided which show only the syringe body 302 and the mounting member 326 of the stackable syringe assembly 106 of FIGS. 3A and 3B. These figures show that the top end of the arm 334 may be configured (e.g., with appropriate notches and ridges) to mount to the gas line coupler 346.

These figures also show that the syringe body 302 may include a partition assembly 358 mounted to the side walls 304 a, c, d of the syringe body 302 which extends into the sample chamber 306. The partition assembly 358 may be configured to reduce foaming of the fluid sample as it passes into the sample chamber 306 en route to the conduit 352. Various configurations of the partition assembly 358 may be used. In the exemplary embodiment, the partition assembly 358 may include a central portion 362 mounted to the side wall 304d of the syringe body 302 at a bottom end 364 of the central portion 362. The central portion 362 may extend upwardly such that a top end 366 of the central portion 362 is positioned at a substantially central location within the sample chamber 306. The partition assembly 358 may include first and second lateral portions 370a, b mounted to opposite sides of the top end 366 of the central portion 362. The central portion 362 and first and second lateral portions 370a, b define multiple gaps 374a-c through which the fluid sample may pass into the bore 307 and subsequently, into the conduit 352, with a reduced amount of foaming.

Figure 20A:
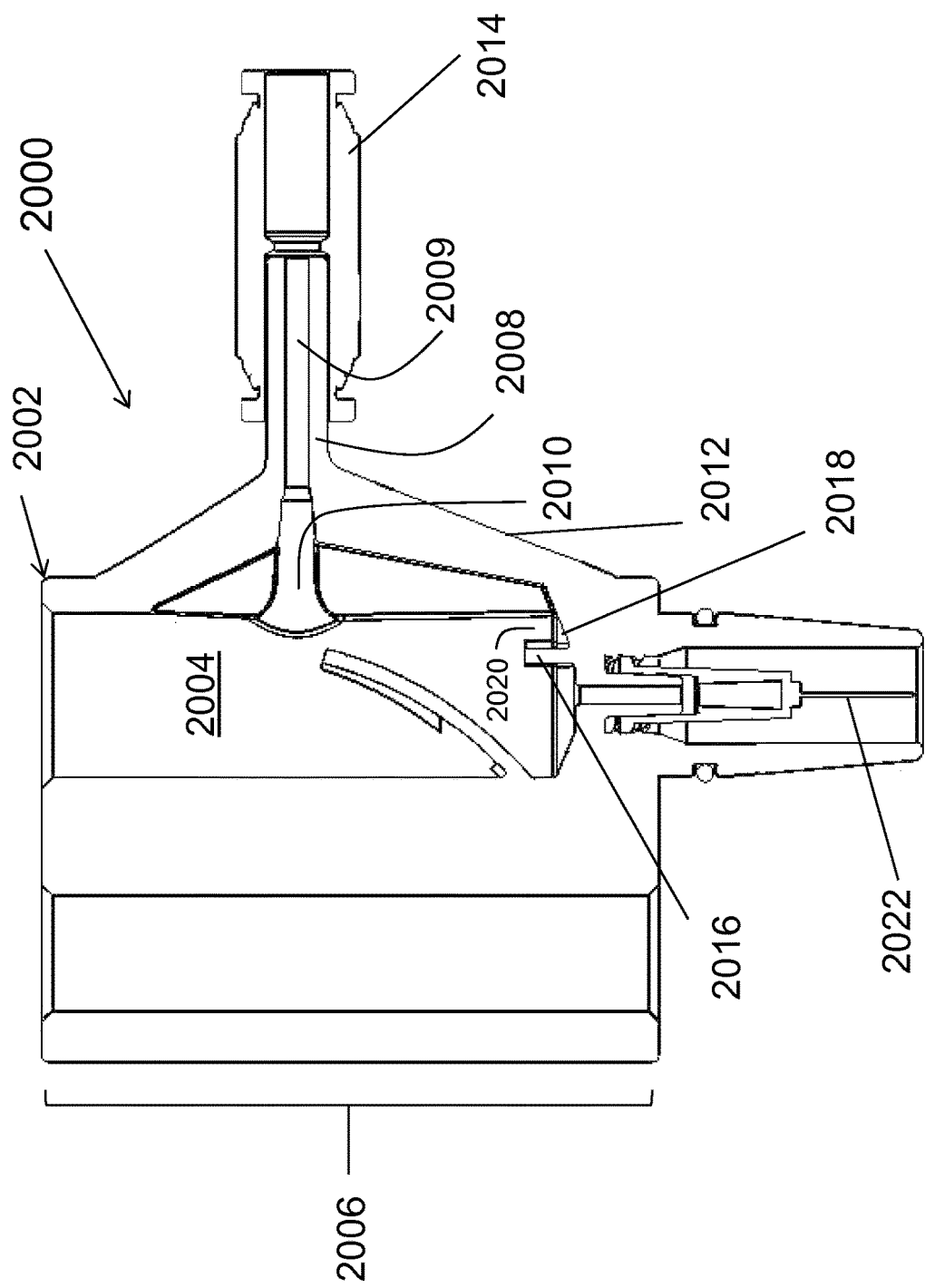
FIG. 20A a front cross-sectional view of a stackable syringe assembly of a syringe stack of a fluid handling system based on gas pressure according to an exemplary embodiment. FIB. 20B shows a back cross-sectional view of the stackable syringe assembly.

With reference to FIG. 20A, a front cross-sectional view of another exemplary stackable syringe assembly 2000 is shown, which includes a syringe body 2002 which defines a sample chamber 2004 and a mounting member 2006. Comparing the stackable syringe assembly 2000 of FIG. 20A to the stackable syringe assembly 106 of FIG. 3B, the structures and components of the two assemblies are similar. As described above, the stackable syringe assembly 2000 may include an arm 2008 which defines a bore 2009 extending from a gas inlet port 2010 defined in a side wall 2012 of the syringe body 2002. However, in this embodiment, the arm 2008 is oriented substantially at a 90° angle with respect to the longitudinal axis of the syringe body 2002. As described above, a gas line coupler 2014 may be mounted to the arm 2008. In this embodiment, the top end of the arm 2008 may also be configured to allow a vial (e.g., an Eppendorf vial) to be mounted to the top end of the arm 2008 when a syringe stack 1000 comprising the stackable syringe assembly 2000 is positioned horizontally (with reference to FIG. 10, further described below). Also in this embodiment, the syringe body 2002 may include a partition projection 2016 extending upwardly from a bottom surface 2018 of the sample chamber 2004. The partition projection 2016 defines a pocket 2020 configured to capture a portion of the fluid sample passing through the sample chamber 2004 en route to a conduit 2022 when the syringe stack is positioned vertically. The dimensions of the pocket 2020 defined by the partition projection 2016 may vary depending upon the desired amount of fluid sample (e.g., 125 µL) to be captured.

Figure 20B:
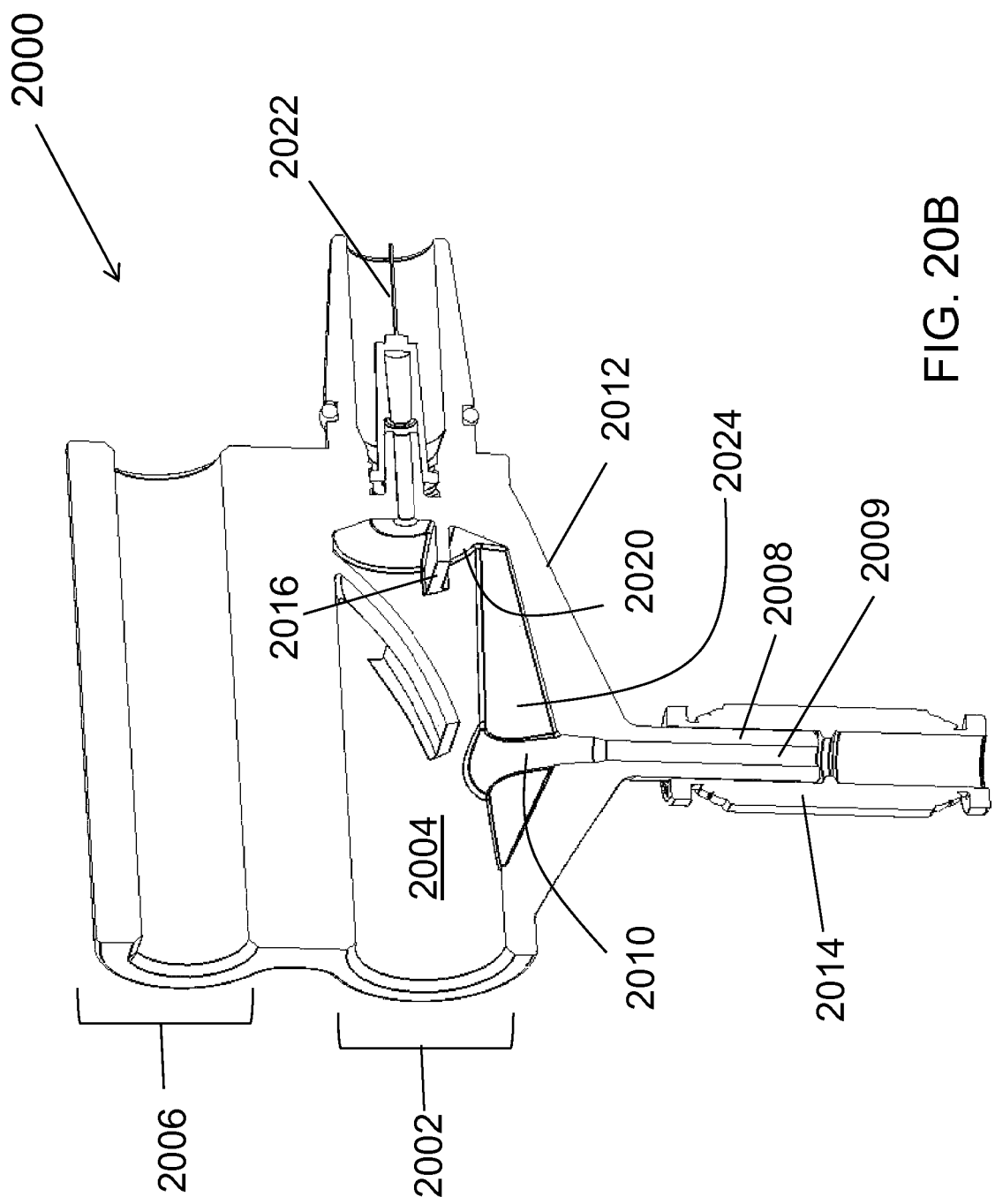

With reference to FIG. 20B, a back cross-sectional view of the stackable syringe assembly 2000 is shown, positioned horizontally. As shown in the figure, the side wall 2012 is configured to define a trough having a sloped surface 2024 to facilitate flow of the captured portion of the fluid sample out of the pocket 2020 as it exits through the bore 2009 of the arm 2008 via the gas inlet port 2010. Thus, in the horizontal position, the gas inlet port 2010 functions as an outlet port.

Figure 4A:
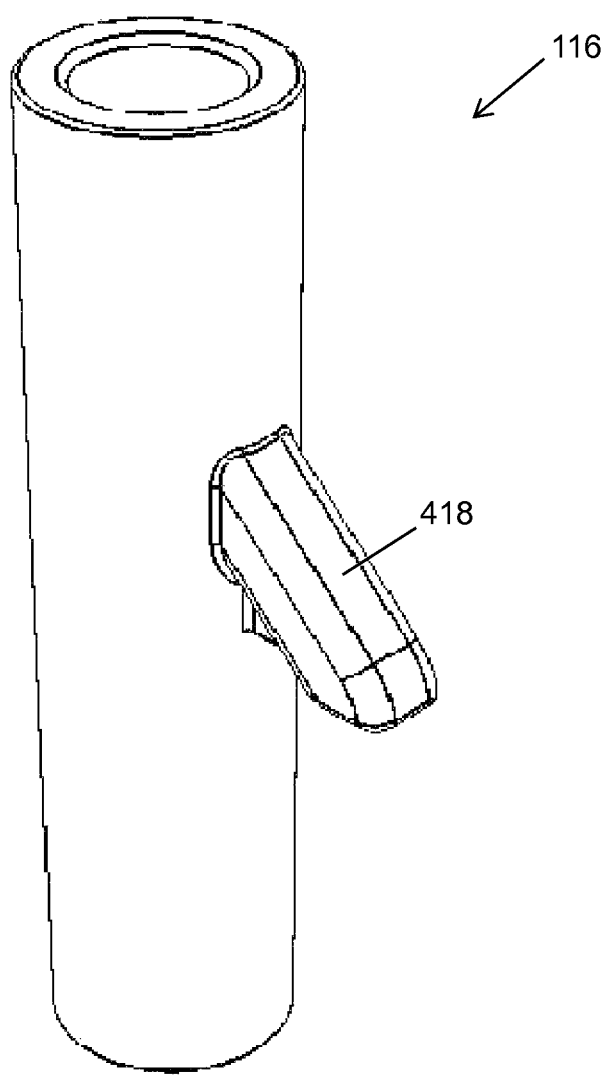
FIG. 4A shows a perspective view of a dispenser of the fluid handling system of FIG. 1.
Figure 4B:
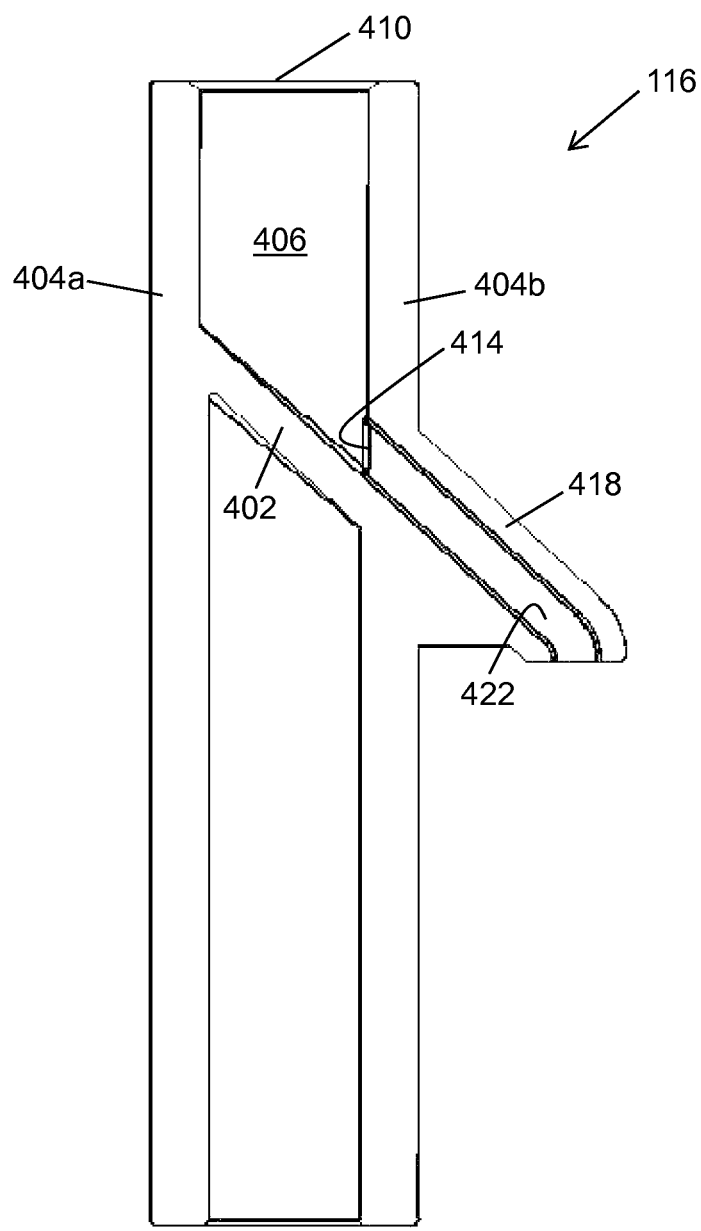
FIG. 4B shows a front cross-sectional view of the dispenser.

With reference to FIGS. 1A, C and 2, the bottommost stackable syringe assembly 206 may be mounted to a dispenser 116 through which the fluid sample may exit out of the syringe stack 104 into a vial 120 (e.g., an Eppendorf vial) inserted into a holder 122. FIG. 4A shows a perspective view of the dispenser 116. FIG. 4B shows a front cross-sectional view of the dispenser 116. The dispenser 116 may include a partition wall 402, which together with the side walls (two of which are labeled 404 a, b) of the dispenser 116 define a dispensing chamber 406 which is accessible via a top opening 410 at a top end of the dispenser 116. The dispensing chamber 406 is also accessible via an outlet port 414 defined in the side wall 404b of the dispenser 116. The dispenser 116 may include a spout 418 extending from the outlet port 414. The walls of the spout 418 may define a bore 422 through which the fluid sample may exit into the vial 120 positioned near an end of the spout 418. The partition wall 402 and the bore 422 may be sloped downwardly to facilitate flow of the fluid sample as it exits the outlet port 414.

Figure 5:
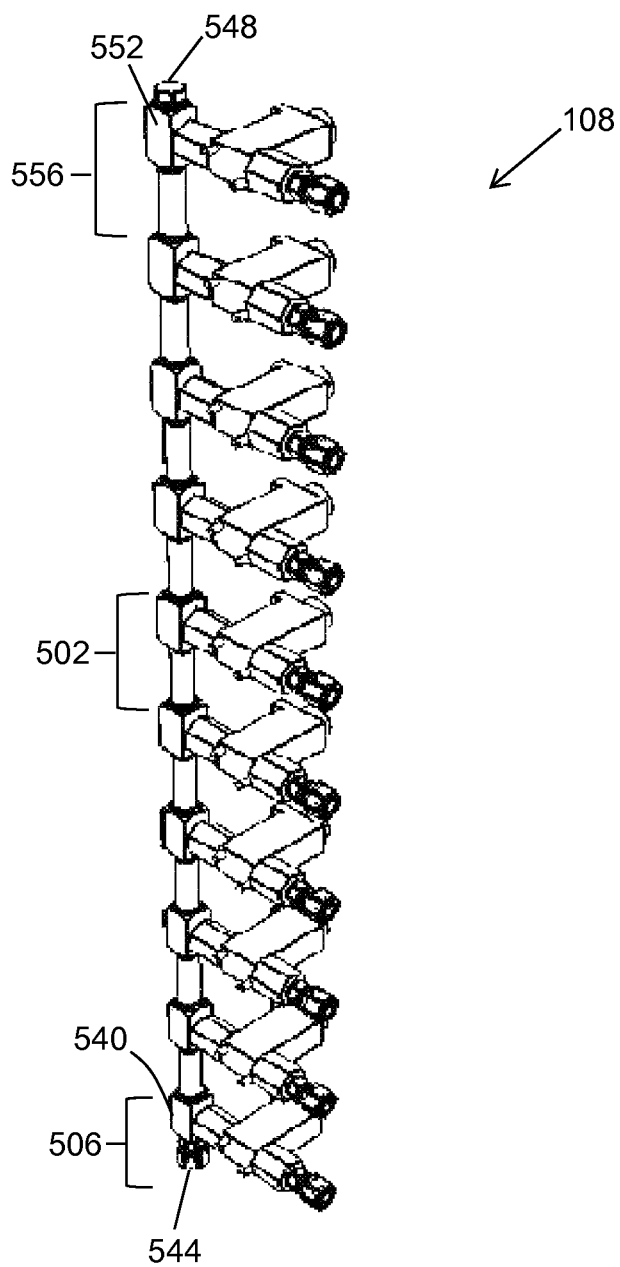
FIG. 5 shows a perspective view of a gas valve stack of a gas delivery system of the fluid handling system of FIG. 1.

As described above, the fluid handling system 100 may include the gas delivery system in fluid communication with the syringe stack 104. The gas delivery system may include the gas valve stack 108 which is configured to deliver gas to each sample chamber of each stackable syringe assembly. Various configurations of the gas valve stack 108 may be used. A perspective view of the exemplary gas valve stack 108 is shown in FIG. 5. The gas valve stack 108 may include a plurality of gas valve assemblies (three of which are labeled 502, 506, 556).

Figure 6:
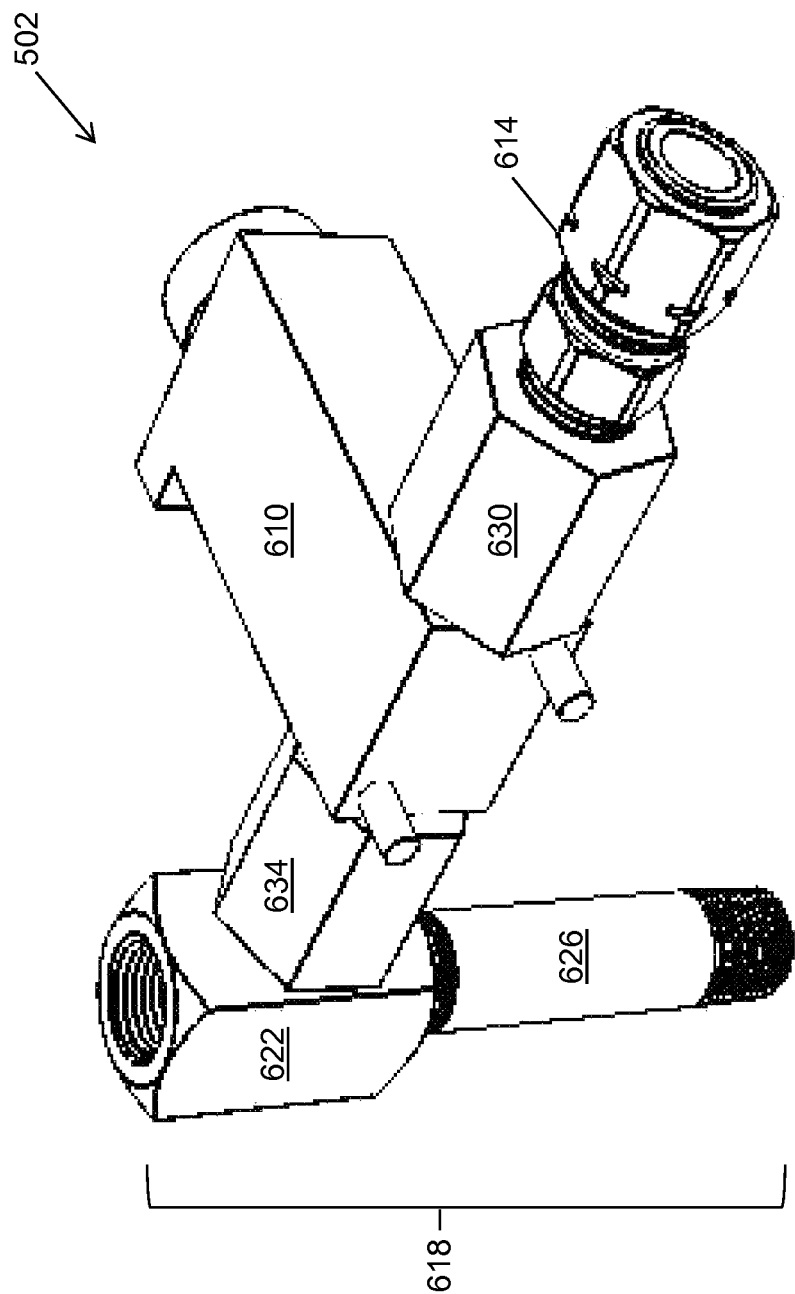
FIG. 6 shows a perspective view of a gas valve assembly of the gas valve stack of FIG. 5.

Various configurations of the gas valve assemblies may be used. A perspective view of the exemplary gas valve assembly 502 is shown in FIG. 6. The exemplary gas valve assembly 502 (which is representative of each of the gas valve assemblies except for the bottommost gas valve assembly 506) may include a gas valve 610, a gas line coupler 614 mounted to the gas valve 610 and a gas source coupler assembly 618. A variety of commercially available gas valves, e.g., solenoid valves, may be used for the gas valve 610. A variety of commercially available gas line couplers may be used for the gas line coupler 614. The gas line coupler 614 is configured to mount to the gas line which is mounted to the gas line coupler 346 of the associated stackable syringe assembly 106 (with reference to FIG. 3). The gas source coupler assembly 618 is configured to deliver gas from a gas source through the gas valve 610, en route to the associated stackable syringe assembly 106. Various configurations of the gas source coupler assembly 618 may be used. In the exemplary embodiment, the gas source coupler assembly 618 includes a block 622 mounted to a tube 626. Bores defined in the block 622 and the tube 626 allow flow of the gas from the gas source. A first adapter 630 may be used to mount the gas valve 610 to the gas line coupler 614. A second adapter 634 may be used to mount the gas valve 610 to the gas source coupler assembly 618.

With reference back to FIG. 5, the bottommost gas valve assembly 506 may be configured similarly to the gas valve assembly 502, except that a gas source coupler assembly for the bottommost gas valve assembly 506 may include a block 540 and another gas line coupler 544 which is configured to mount to a gas line that is in fluid communication with the gas source. A variety of gas sources may be used, e.g., air or an inert gas such as N₂. Gas from the gas source flows into the gas valve stack 108 through the gas line coupler 544 and into each gas valve assembly.

The gas valves of the gas valve assemblies may be three-way gas valves such that when the gas valve is open, the gas will continue to flow to a sample chamber of an associated stackable syringe assembly in the syringe stack 104 while the sample chamber is isolated from atmosphere. When the gas valve is closed, gas no longer flows to the sample chamber in the associated stackable syringe assembly in the syringe stack 104 and the sample chamber is vented to atmosphere. The gas valve stack 108 may be sealed via a cap 548 configured to insert into a top opening of a block 552 of an uppermost gas valve assembly 556 and to form another pressure-tight seal.

Figure 7A:
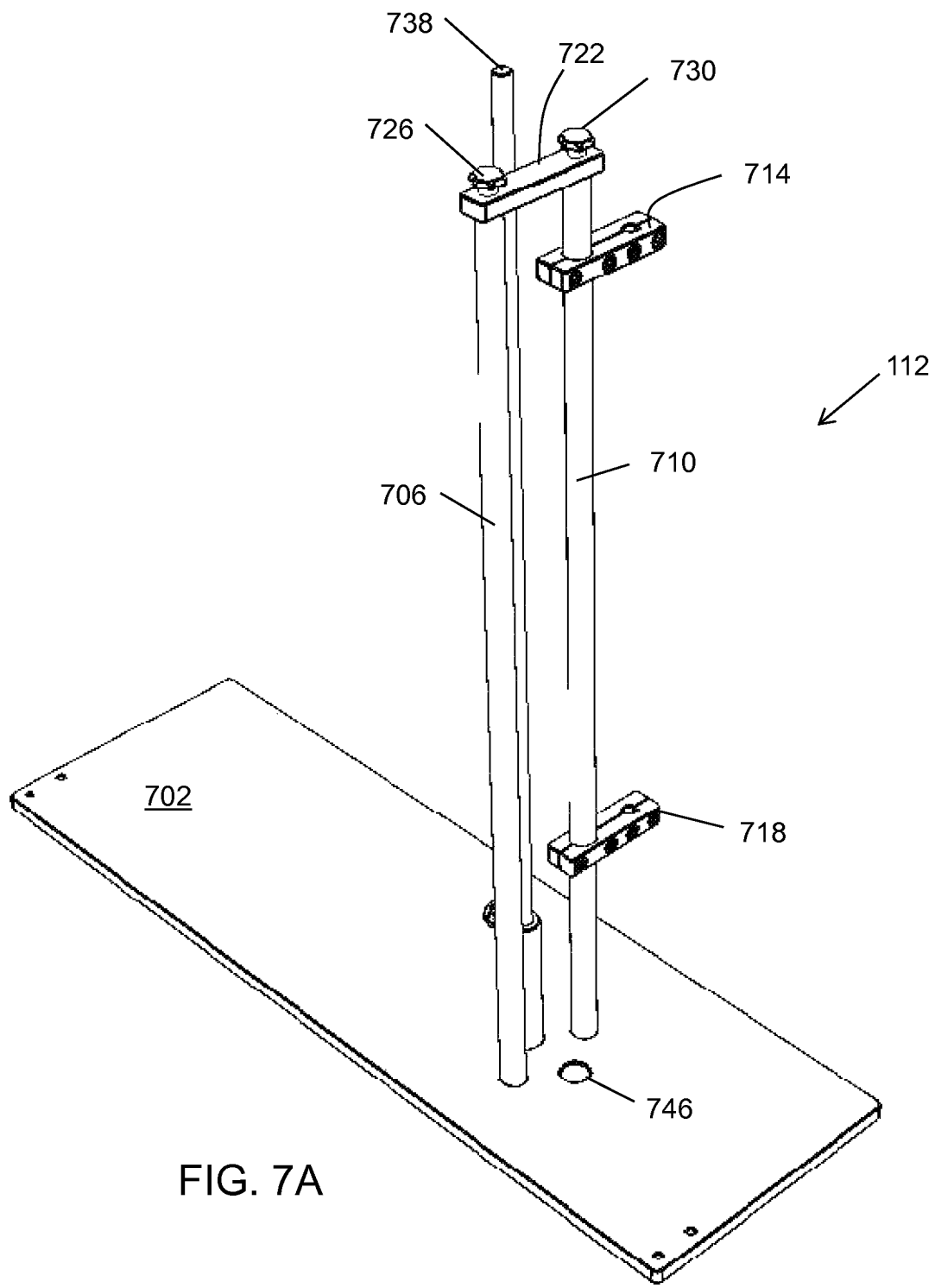
FIG. 7A shows a perspective view of a support assembly of the fluid handling system of FIG. 1, the support assembly configured to support and position components of the fluid handling system in a vertical orientation.
Figure 7B:
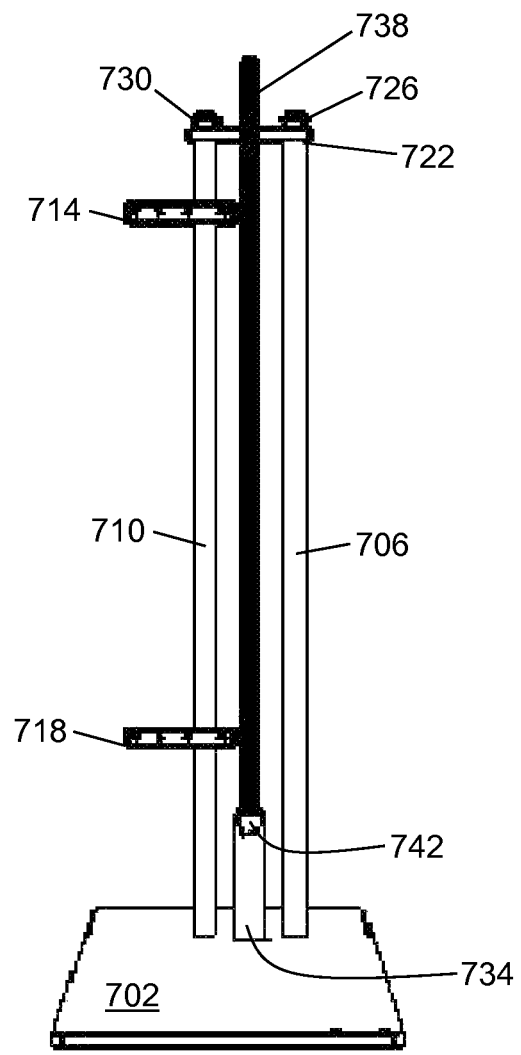
FIG. 7B shows a side view of the support assembly.
Figure 10:
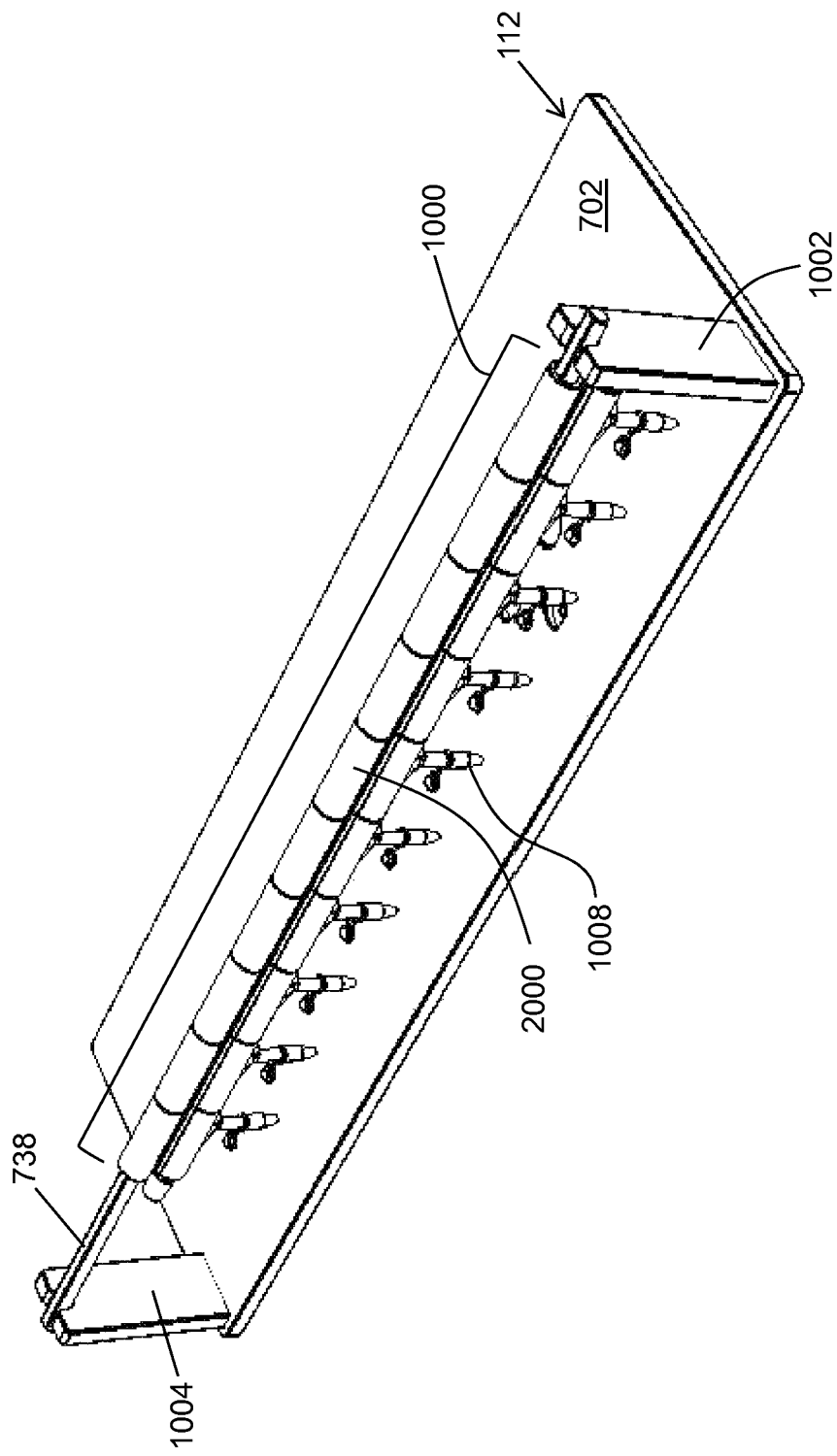
FIG. 10 shows a perspective view of a syringe stack supported and positioned by a support assembly of a fluid handling system in a horizontal orientation according to an exemplary embodiment.

As described above, the fluid handling system 100 may include the support assembly 112 mounted to various components of the fluid handling system 100 and configured to support and to position various components of the fluid handling system 100 in certain orientations, e.g., vertically (with reference to FIG. 1) and horizontally (with reference to FIG. 10, discussed further below). FIG. 7A shows a perspective view of the support assembly 112. FIG. 7B shows a side view of the support assembly 112. Various configurations of the support assembly 112 may be used. In the exemplary embodiment, the support assembly 112 may include a base plate 702. The support assembly 112 may include a first support post 706 mounted at an end to the base plate 702 and a second support post 710 mounted at an end to the base plate 702 and positioned substantially parallel to the first support post 706. The second support post 710 may mount to the gas valve stack 108, e.g., via a first clamp 714 mounted on an end to the second support post 710 and mounted on an opposing end to a tube of a gas source coupler assembly of a gas valve assembly (as shown in FIG. 1C). The second support post 710 may also mount to the gas valve stack 108 via a second clamp 718 mounted on an end to the second support post 710 and mounted on an opposing end to another tube of another gas source coupler assembly of another gas valve assembly (as shown in FIG. 1C). Opposing ends of the first support post 706 and the second support post 710 may each be mounted to a cross bar 722, e.g., via a first fastener 726 and a second fastener 730.

The support assembly 112 may include a collar 734 mounted to the base plate 702 and positioned between the first support post 706 and the second support post 710, but offset from a line connecting the first support post 706 and the second support post 710. The collar may mount to (e.g., via a fastener 742) the syringe stack support rod 738 which is inserted into a bore defined in the collar 734. As described above, the syringe stack support rod 738 may also be inserted into the bores of the tubular mounting members of the stackable syringe assemblies (as shown in FIG. 1B).

The support assembly 112 may include the holder 122 (with reference to FIGS. 1A-C) mounted at an end to the base plate (e.g., via a cavity 746 defined in the base plate 702). The holder 122 may mount to the vial 120 (as shown in FIGS. 1A-C).

The components of the fluid handling system 100 may be formed from a variety of materials having sufficient strength and rigidity for the described application. With respect to the syringe bodies of the stackable syringe assemblies, materials suitable for stereolithographic fabrication or injection molding may be used, e.g., various plastics.

Figure 8:
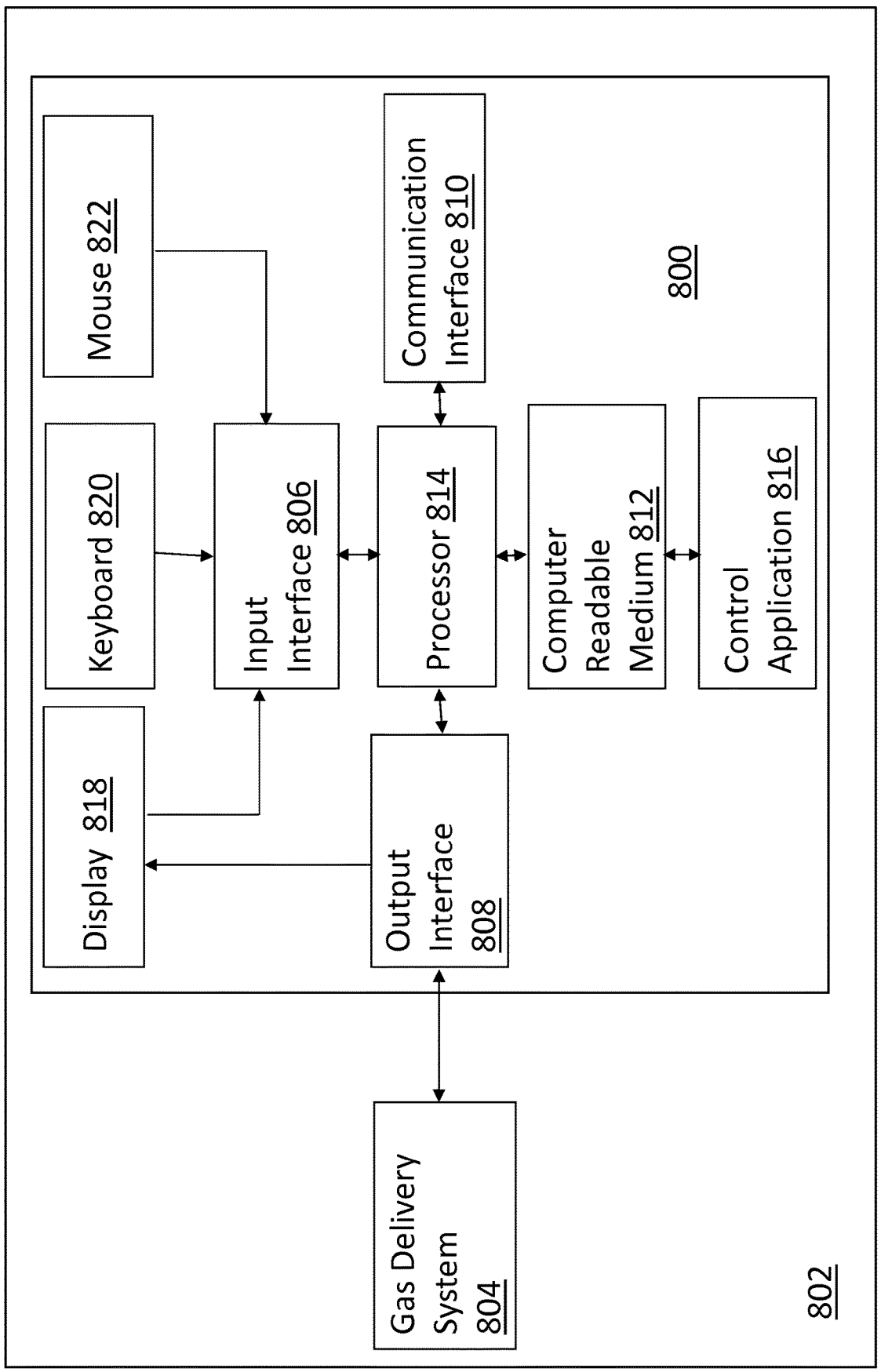
FIG. 8 depicts a control system of a fluid handling system based on gas pressure according to an exemplary embodiment.

With reference to FIG. 8, an exemplary embodiment of a control system 800 of a fluid handling system 802 is shown.

The control system 800 controls the operation of various components of the fluid handling system 802 and may be used to automate the application of the plurality of pulses of fluid shear stress to the fluid sample. For example, the control system 800 may be operably coupled to a gas delivery system 804 of the fluid handling system 802. With reference to the fluid handling system 100 shown in FIG. 1, the control system 800 may be used to control the delivery of gas to each of the sample chambers of each of the stackable syringe assemblies in the syringe stack 104. For example, the control system 800 may be used to sequentially deliver gas to each of the sample chambers at a selected pressure for a selected duration time. One or more of the components of the control system 800 may be mounted on a printed circuit board mounted on another component of the fluid handling system.

The control system 800 may include an input interface 806, an output interface 808, a communication interface 810, a computer-readable medium 812, a processor 814, and a control application 816. The control system 800 may include fewer or additional components as compared to those shown in FIG. 8.

Input interface 806 provides an interface for receiving information from the user (e.g., a selected hold time between pulses of fluid shear stress) for processing by control system 800. Although not shown, input interface 806 may further provide an interface for receiving information from gas delivery system 804 (e.g., a flowmeter output signal) for processing by control system 800. Input interface 806 may interface with various input technologies including, but not limited to, a display 818, a keyboard 820, a mouse 822, a touch screen, a track ball, a keypad, etc. to allow the user to enter information into control system 800 or to make selections presented in a user interface displayed on display 818. Display 818 may be a thin film transistor display, a light emitting diode display, a liquid crystal display, or any of a variety of different displays known to those skilled in the art. control system 800 may have one or more input interfaces that use the same or a different input interface technology.

Figure 17:
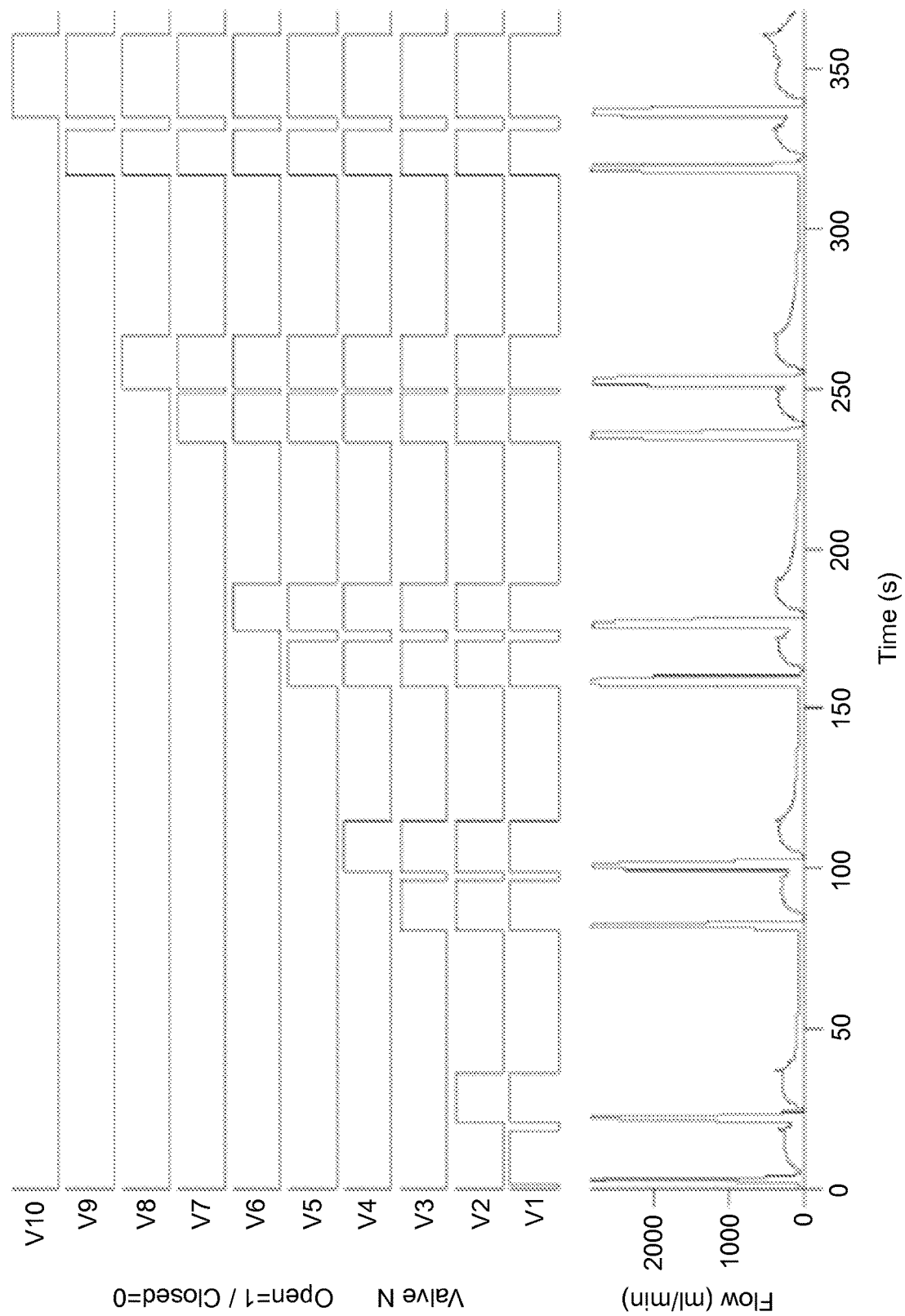
FIG. 17 shows the state of each gas valve in each gas valve assembly during an exemplary set of operations and the corresponding flow rate of gas being delivered by the gas delivery system for the fluid handling system of FIG. 1 according to an exemplary embodiment.

Output interface 808 provides an interface for outputting information for review by a user of fluid handling system 802. Such information may include the open/close status of each of the gas valves of each of the gas valve assemblies as a function of time as shown in FIG. 17; the selected hold time; a flow rate of gas through a gas line of the gas delivery system as a function of time as shown in FIG. 17 (i.e., a gas flow profile); a corresponding flow time and/or a corresponding flow rate of the fluid sample through each of the conduits of each of the stackable syringe assemblies; etc. Monitoring gas flow profiles during the operation of the fluid handling system 802 as shown in FIG. 17 provides a diagnostic on the fluid sample transfer conditions which may inform the user of abnormal conditions, e.g., an undesired flow rate or conduit plugging. Similarly, such monitoring provides a measure of consistency and reproducibility since the gas flow profiles can be compared for different fluid samples. Output interface 808 may further provide an interface for outputting information to gas delivery system 804 (e.g., a valve signal to open/close a particular gas valve of a particular gas valve assembly)). Control system 800 may have one or more output interfaces that use the same or a different interface technology.

Communication interface 810 provides an interface for receiving and transmitting data between devices using various protocols, transmission technologies, and media as known to those skilled in the art. Communication interface 810 may support communication using various transmission media that may be wired or wireless. Exemplary wireless communication devices include antennas that receive and transmit electromagnetic radiation at various frequencies. Control system 800 may have one or more communication interfaces that use the same or a different communication interface technology. Data and messages may be transferred between any input or output device and controller 800 using communication interface 810. Thus, communication interface 810 provides an alternative (or additional) interface to either or both of input interface 806 and output interface 808.

Control system 800 may be linked to one or more interfaced devices. For example, control system 800 may interface with another fluid handling system, an external computing device, an external system for analyzing certain characteristics of collected processed fluid samples. If connected, control system 800 and the one or more interfaced devices may be connected directly or through a network. The network may be any type of wired and/or wireless public or private network including a cellular network, a local area network, a wide area network such as the Internet, etc. Control system 800 may send and receive information to/from one or more of the interfaced devices. For example, control system 800 may send results obtained for the fluid sample for storage on one or more of the interfaced devices. As another example, control system 800 may receive software updates from one or more of the interfaced devices and/or receive commands from one or more of the interfaced devices. The commands may control operation of one or more components of fluid handling system 802 including control system 800. The one or more interfaced devices may include a computing device of any form factor such as a personal digital assistant, a desktop computer, a laptop computer, an integrated messaging device, a cellular telephone, a smart phone, a pager, etc. without limitation.

Computer-readable medium 812 is an electronic holding place or storage for information so that the information can be accessed by processor 814 as known to those skilled in the art. Computer-readable medium 812 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Control system 800 may have one or more computer-readable media that use the same or a different memory media technology. Control system 800 also may have one or more drives that support the loading of a memory media such as a CD or DVD.

Processor 814 executes instructions as known to those skilled in the art. The instructions may be carried out by a special purpose computer, logic circuits, or hardware circuits. Thus, processor 814 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 814 executes an instruction, meaning that it performs/controls the operations called for by that instruction. Processor 814 operably couples with input interface 806, with computer-readable medium 812, with communication interface 810, and with output interface 808 to receive, to send, and to process information. Processor 814 may retrieve a set of instructions from a permanent memory device and copy the instructions in an executable form to a temporary memory device that is generally some form of RAM. Control system 800 may include a plurality of processors that use the same or a different processing technology.

Control application 816 performs operations associated with controlling the operation of fluid handling system 802 and/or performs operations associated with processing output signals or input signals received by various components of fluid handling system 802. Some or all of the operations described herein may be controlled by instructions embodied in control application 816. The operations may be implemented using hardware, firmware, software, or any combination of these methods. With reference to the example embodiment of FIG. 8, control application 816 may be implemented in software (comprised of computer-readable and/or computer-executable instructions) stored in computer-readable medium 812 and accessible by processor 814 for execution of the instructions that embody the operations of control application 816. Control application 816 may be written using one or more programming languages, assembly languages, scripting languages, etc.

Figure 9:
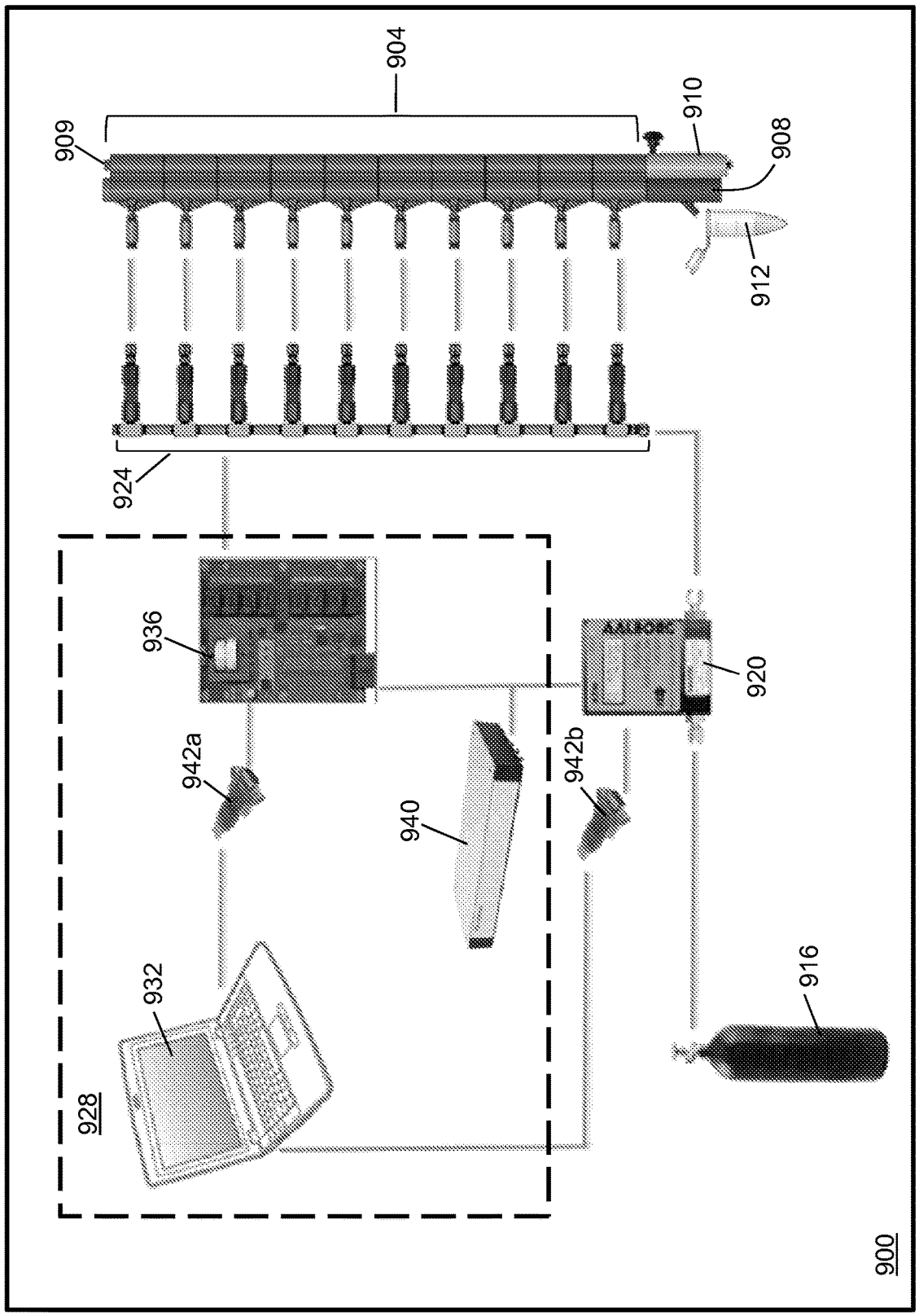
FIG. 9 depicts a fluid handling system based on gas pressure according to an exemplary embodiment.

With reference to FIG. 9, another exemplary embodiment of a fluid handling system 900 for applying a plurality of pulses of fluid shear stress to a fluid sample is shown. The fluid handling system 900 may include a syringe stack 904 mounted to a dispenser 908 through which the fluid sample may exit out of the syringe stack 904 into a vial 912. The syringe stack 904 may be mounted to a syringe stack support rod 909 mounted to a collar 910 of a support assembly of the fluid handling system 900. The fluid handling system 900 may include a gas delivery system in fluid communication with the syringe stack 904. The gas delivery system may include a gas source 916 in fluid communication with a flowmeter 920 in fluid communication with a gas valve stack 924. The gas valve stack 924 may include a plurality of gas valve assemblies, each gas valve assembly in fluid communication with an associated stackable syringe assembly of the syringe stack 904. The fluid handling system 900 may include a control system 928 operably coupled to the gas delivery system of the fluid handling system 900. Various configurations of the control system 928 may be used. In the exemplary embodiment, the control system 928 may include a computer 932, a relay board 936 and a power supply 940. Components of the control system 928 may be operably coupled via adapters 942 a, b. The fluid handling system 900 may include fewer or additional components as compared to those shown in FIG. 9.

The following exemplary operations may be carried out when using any of the disclosed fluid handling systems based on gas pressure to apply a plurality of pulses of fluid shear stress to a fluid sample. At least some of these operations may be performed by the control system 800 (including the control application 816) or the control system 928. To begin, the fluid sample may be loaded into an uppermost stackable syringe assembly of a syringe stack via a top opening in the uppermost stackable syringe assembly. The top opening may then be sealed via a cap. The fluid sample will be contained in an uppermost sample chamber of the uppermost stackable syringe assembly.

In a first operation, pressurize the uppermost sample chamber of the uppermost stackable syringe assembly to a selected pressure while each sample chamber of each other stackable syringe assembly in the syringe stack are each vented to atmosphere. This may be accomplished by opening a gas valve of a gas valve assembly associated with the uppermost stackable syringe assembly and closing each gas valve of each other gas valve assembly. The pressurization provides a force which pushes the fluid sample from the uppermost sample chamber through a conduit of the uppermost stackable syringe assembly into a second sample chamber of a second stackable syringe assembly (i.e., the stackable syringe assembly immediately below the uppermost stackable syringe assembly), thereby exposing the fluid sample to a first pulse of fluid shear stress. The selected pressure may be that which provides a selected flow rate of the fluid sample through the conduit (for a conduit of a particular inner diameter). The selected flow rate provides a selected duration time for the first pulse of fluid shear stress (for a conduit of a particular length). Similarly, the selected flow rate provides a selected magnitude of fluid shear stress for the first pulse of fluid shear stress (flow rate and fluid shear stress are related via Poiseuille's equation as described above). An exemplary selected pressure may be about 300 psig to provide a selected flow rate of about 250 µL/sec. Other selected pressures may be that sufficient to provide a selected flow rate in the range of about 25 µL/sec to about 250 µL/sec. A gas regulator (or another similar device) in fluid communication with a gas source may be used to provide for variable control of the pressure and thus, variable flow rates.

In a second operation, maintain pressurization until a first indicator (e.g., a first flowmeter output signal) indicates a jump in gas flow corresponding to the complete delivery of the fluid sample through the conduit of the uppermost stackable syringe assembly. The fluid sample will now be in the second sample chamber of the second stackable syringe assembly.

In a third operation, vent the uppermost sample chamber of the uppermost stackable syringe assembly for a selected hold time, e.g., a few minutes. The hold time may be eliminated such that the hold time is effectively zero. This may be accomplished by closing the gas valve of the gas valve assembly associated with the uppermost stackable syringe assembly.

In a fourth operation, pressurize the uppermost sample chamber of the uppermost stackable syringe assembly and the second sample chamber of the second stackable syringe assembly to the selected pressure while each sample chamber of each other stackable syringe assembly in the syringe stack are each vented to atmosphere. The pressurization provides a force which pushes the fluid sample from the second sample chamber through a conduit of the second stackable syringe assembly into a third sample chamber of a third stackable syringe assembly (i.e., the stackable syringe assembly immediately below the second stackable syringe assembly), thereby exposing the fluid sample to a second pulse of fluid shear stress.

In a fifth operation, maintain pressurization until a second indicator (e.g., a second flowmeter output signal) indicates a jump in gas flow corresponding to the complete delivery of the fluid sample through the conduit of the second stackable syringe assembly. The fluid sample will now be in the third sample chamber of the third stackable syringe assembly.

In a sixth operation, vent sample chambers of the uppermost and the second stackable syringe assemblies for the selected hold time (or a different selected hold time).

In subsequent operations, repeat the pressurizing, maintaining pressurization and venting operations until the fluid sample has passed through each stackable syringe assembly.

In a final operation, vent each sample chamber of each stackable syringe assembly to atmosphere.

After the application of one or more pulses of fluid shear stress, the fluid sample may be referred to as "a processed fluid sample" which may be collected and analyzed via a variety of techniques, e.g., techniques for determining the concentration of viable cells in the processed fluid sample, including those described in U.S. Pat. Pub. No. 20140038231. As shown in FIGS. 1A-C, the processed fluid sample may be collected via the dispenser 116 and vial 120. Such processed fluid sample has been exposed to a number of pulses of fluid shear stress equivalent to the number of stackable syringe assemblies in the syringe stack 104.

However, processed fluid sample which has been exposed to a smaller number of pulses of fluid shear stress may also be collected and similarly analyzed. As described above with reference to the stackable syringe assembly 106 shown in FIG. 3B, a pipette tip 354 may be inserted into the bore 342 of the arm 334 in order to withdraw a portion of the fluid sample in the sample chamber 306, e.g., during a hold time between operations described above. The fluid sample may be withdrawn while the syringe stack 104 is in the vertical orientation (with reference to FIG. 1). Such withdrawn portions include processed fluid sample which has been exposed to a smaller number of pulses of fluid shear stress, i.e., a number equivalent to the number of stackable syringe assemblies above the stackable syringe assembly from which the fluid sample is withdrawn.

Alternatively, as described above with reference to the stackable syringe assembly 2000 shown in FIG. 20, passage of the fluid sample through the sample chamber 2004 results in a portion of the fluid sample being captured by the pocket 2020. Such captured portions include processed fluid sample which has been exposed to a smaller number of pulses of fluid shear stress as compared to processed fluid sample collected in a dispenser mounted to a syringe stack comprising the stackable syringe assembly 2000. The captured portions of fluid sample in each stackable syringe assembly may be collected by first opening or removing each gas line coupler of each stackable syringe assembly and mounting a vial (e.g., an Eppendorf vial) to each arm of each stackable syringe assembly. Next, as shown in FIG. 10, the syringe stack 1000 mounted to the syringe stack support rod 738 may be removed from the collar 734 (with reference to FIG. 7B) and positioned horizontally. The support assembly 112 (with reference to FIG. 7) may include components configured to support and position the syringe stack 1000 in the horizontal orientation. For example, a first cradle 1002 and a second cradle 1004 may be mounted to the base plate 702. The first and second cradles each include a notch in which the ends of the syringe stack support rod 738 may rest. Vials (one of which is labeled 1008) mounted to each arm of each stackable syringe assembly collect the captured portions of processed fluid sample.

Fluid Handling System Based on Mechanical Pressure

Figure 11A:
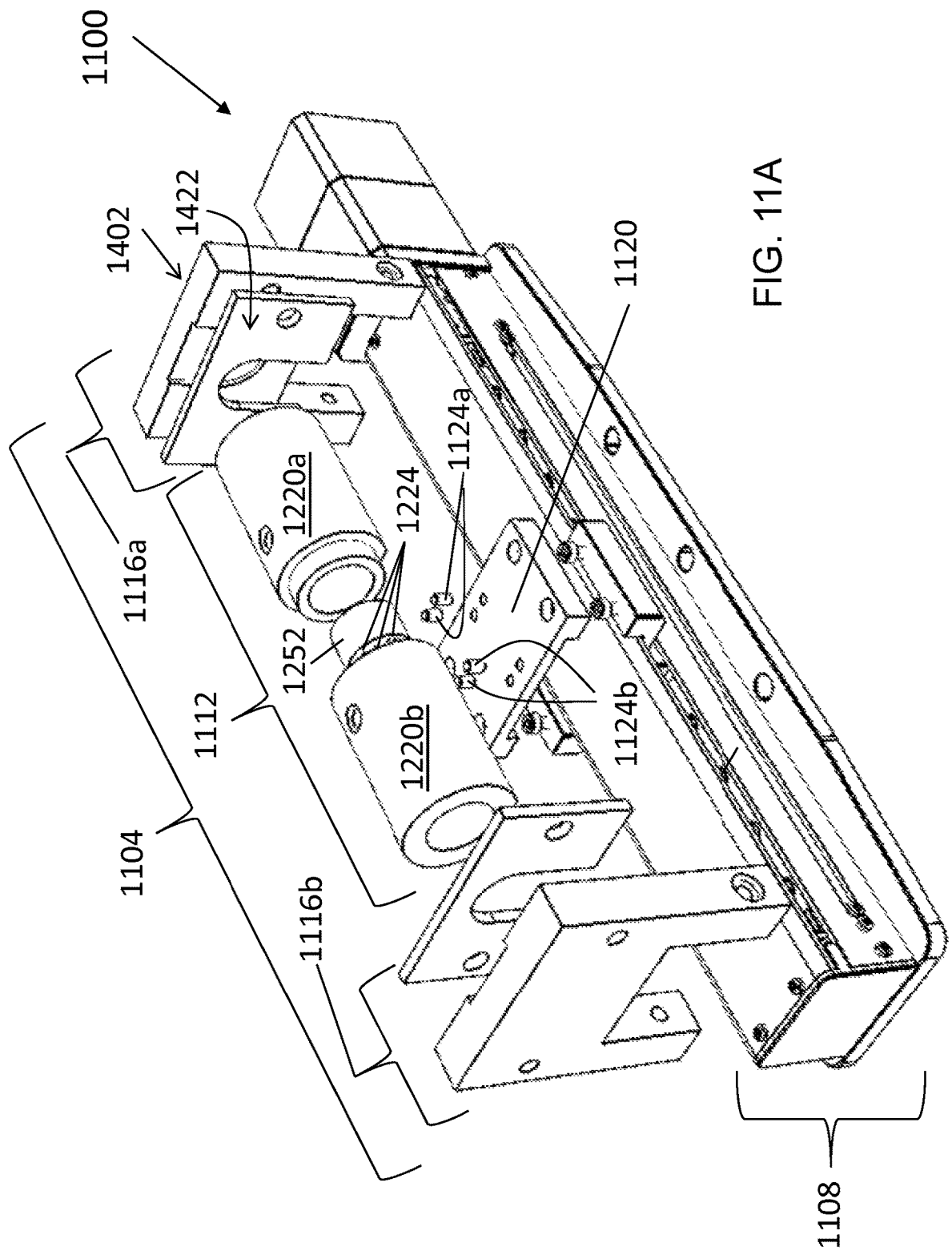
FIG. 11A shows a perspective, exploded view of a fluid handling system based on mechanical pressure according to an exemplary embodiment.
Figure 11B:
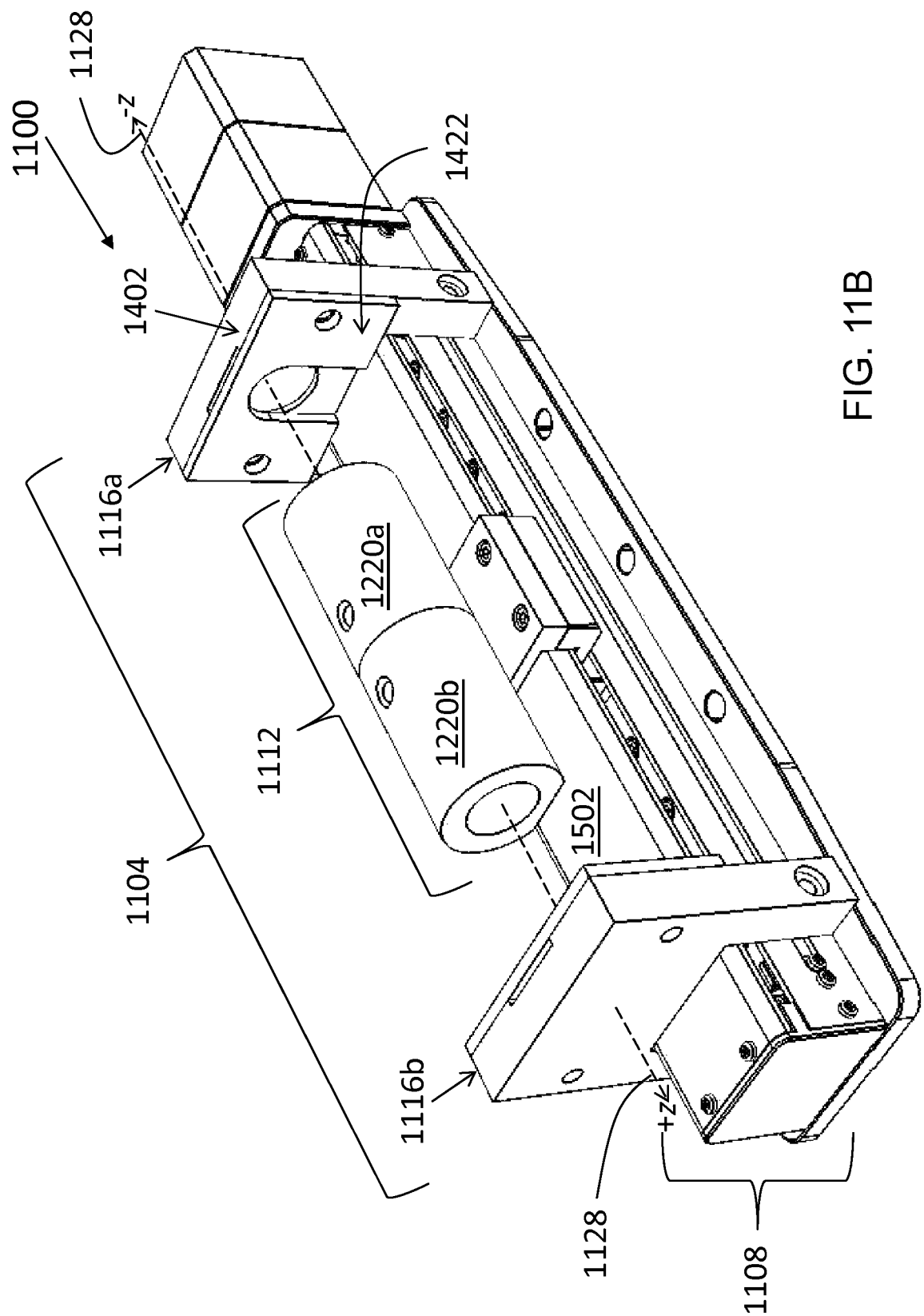
FIG. 11B shows a perspective, assembled view of the fluid handling system.

With reference to FIG. 11, a fluid handling system 1100 for applying a plurality of pulses of fluid shear stress to a fluid sample using mechanical pressure is shown in accordance with an exemplary embodiment. FIG. 11A shows a perspective, exploded view of the fluid handling system 1100. FIG. 11B shows a perspective, assembled view of the fluid handling system 1100. The fluid handling system 1100 may include a syringe assembly 1104 and a linear drive assembly 1108. The syringe assembly 1104 may include a sample receptacle assembly 1112, a first fixed piston (not shown) mounted to the sample receptacle assembly 1112 using a first piston anchor assembly 1116a and a second fixed piston (not shown) mounted to the sample receptacle assembly 1112 using a second piston anchor assembly 1116b. The fluid handling system 1100 may include fewer or additional components as compared to those shown in FIG. 11.

Figure 12A:
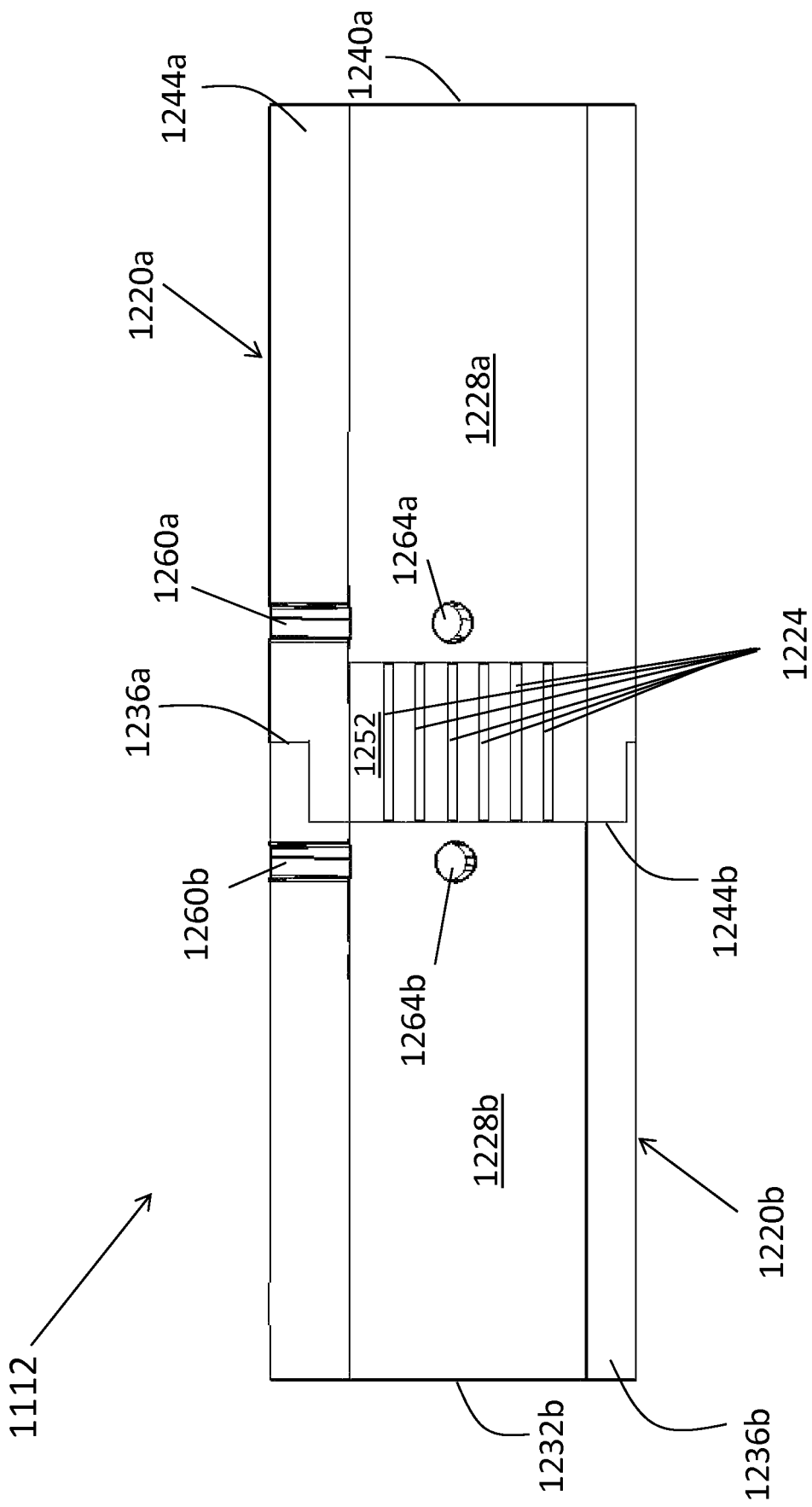
FIG. 12A shows a front, cross-sectional view of a sample receptacle assembly of the fluid handling system of FIG. 11.
Figure 12C:
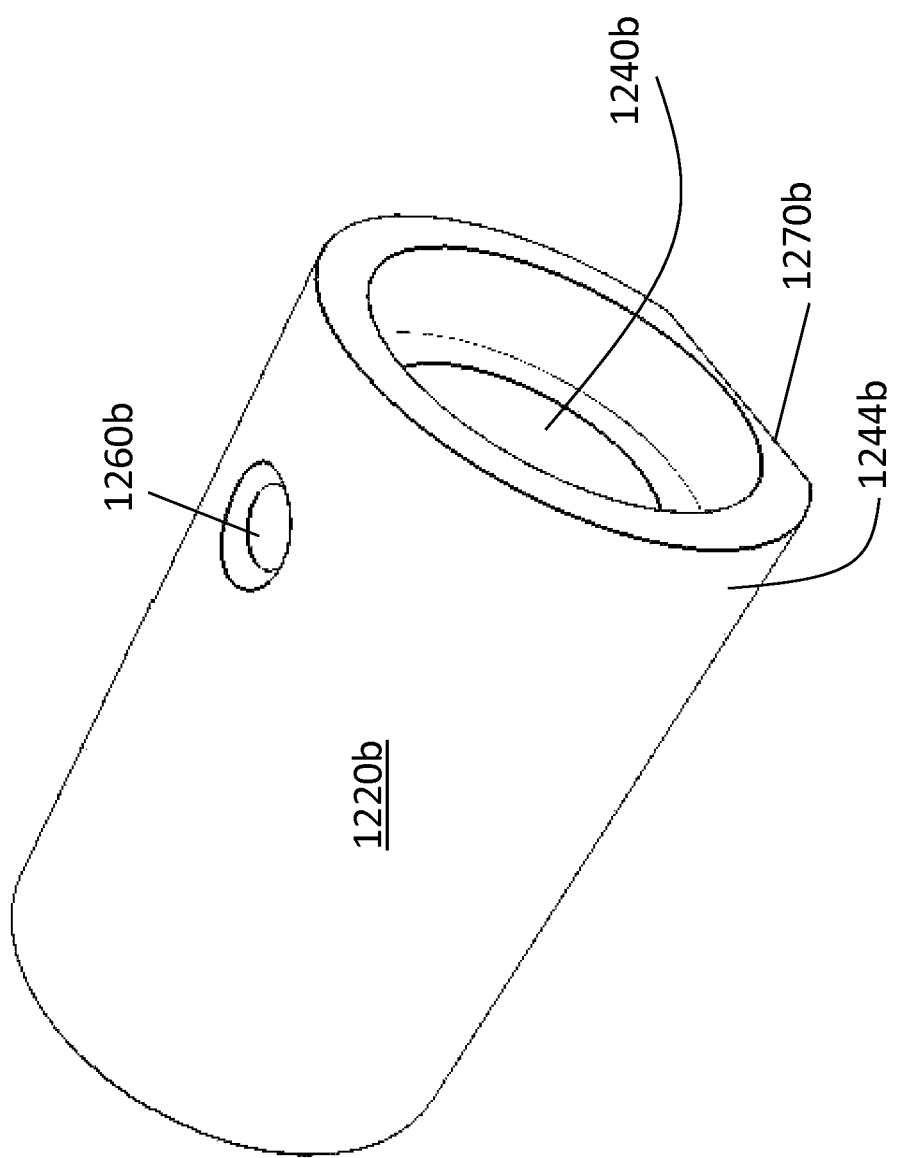
FIG. 12C shows a perspective view of a second syringe body of the sample receptacle assembly.
Figure 12D:
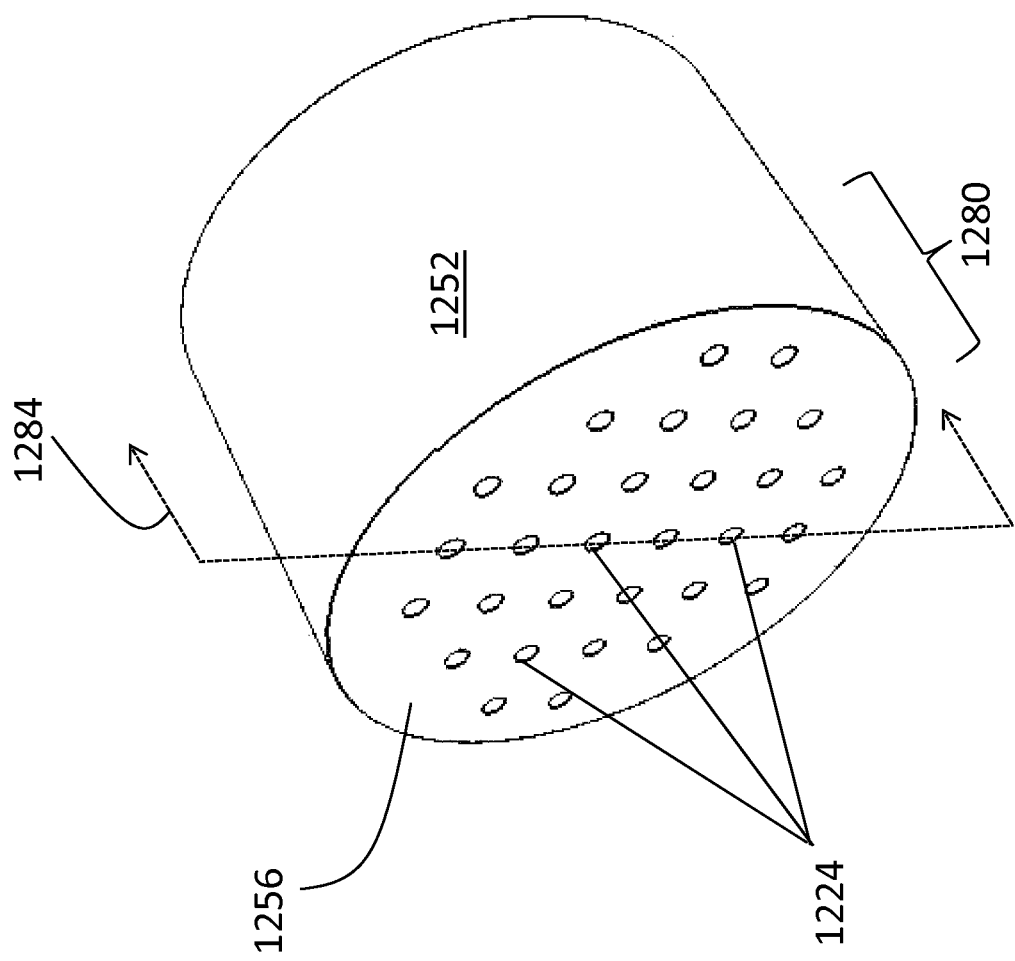
FIG. 12D shows a perspective view of a conduit holding block in which a plurality of substantially parallel conduits is embedded.
Figure 12E:
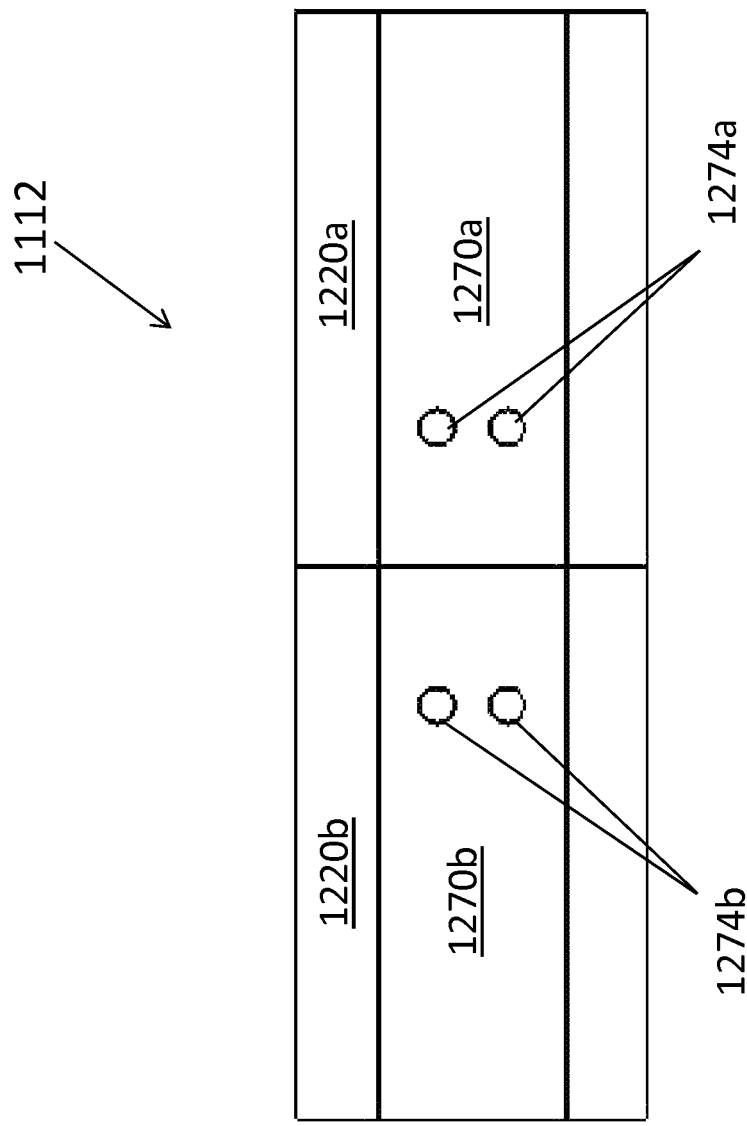
FIG. 12E shows a bottom view of the sample receptacle assembly.

Various configurations of the sample receptacle assembly 1112 may be used which are capable of holding a selected volume of fluid sample (e.g., 5 mL, 10 mL, etc.). FIG. 12A-E show an exemplary sample receptacle assembly 1112 in more detail. FIG. 12A shows a front, cross-sectional view of the sample receptacle assembly 1112. The sample receptacle assembly 1112 may include a first syringe body 1220a mounted to a second syringe body 1220b and a plurality of substantially parallel conduits mounted between the first syringe body 1220a and the second syringe body 1220b. FIG. 12B shows a perspective view of the first syringe body 1220a. FIG. 12C shows a perspective view of the second syringe body 1220b. FIG. 12D shows a perspective view of a conduit holding block 1252 defining a plurality of substantially parallel channels 1224 configured to receive the plurality of substantially parallel conduits. FIG. 12E shows a bottom view of the sample receptacle assembly 1112.

The walls of the first syringe body 1220a may define a first bore 1228a which is accessible via a first opening 1232a at a first end 1236a and a second opening 1240a at a second, opposing end 1244a. Similarly, the walls of the second syringe body 1220b define a second bore 1228b which is accessible via a third opening 1232b at a third end 1236b and a fourth opening 1240b at a fourth, opposing end 1244b. The first syringe body 1220a may be mounted to the second syringe body 1220b by shaping the first end 1236a of the first syringe body 1220a and the fourth end 1244b of the second syringe body 1220b such that the first end 1236a of the first syringe body 1220a may be inserted into the second syringe body 1220b at the fourth opening 1240b, i.e., press fitted into the second syringe body 1220b. For example, the outside diameter of the first syringe body 1220a may be reduced at the first end 1236a to form an inner tubular projection 1248 extending from the first end 1236a of the first syringe body 1220a. The inside diameter of the second syringe body 1220b may be increased by a substantially similar amount at the fourth end 1244b to form a recess into which the inner tubular projection 1248 may be inserted. The first bore 1228a and the second bore 1228b may have substantially similar diameters, thereby defining a substantially continuous bore in the sample receptacle assembly 1112. A variety of materials may be used for the first syringe body 1220a and the second syringe body 1220b, e.g., stainless steel or a plastic, e.g., Radel® by Solvay Specialty Polymers.

The plurality of substantially parallel conduits may be embedded in the conduit holding block 1252 having a first face 1256 and second face (not shown) via the plurality of substantially parallel channels 1224 formed therein. The plurality of substantially parallel conduits may be arranged in an array within the conduit holding block 1252. The dimensions of each conduit and the total number of conduits (e.g., 0.028 inches outer diameter, 0.006 inches inner diameter, 1.27 inches length) may be selected to provide a selected magnitude and selected duration time for the pulses of fluid shear stress to be applied (for a given mechanical pressure applied to the fluid sample). The conduits may be micron-sized, e.g., the inner diameter of the conduit may be less than about 1000 um, less than about 500 µm, less than about 200 µm, less than about 150 µm, etc. The conduits may have a wall thickness (e.g., 0.011 inches) sufficient to facilitate insertion into the channels 1224 of the conduit holding block 1252 while maintaining a substantially straight lumen. The conduits may be substantially uniform such that the dimensions of each conduit are substantially the same as the dimensions of another conduit in the plurality of conduits.

A variety of materials may be used for the conduits, e.g., stainless steel, plastic or glass. Commercially available conduits having such dimensions and made from such a material may be used (e.g., Hypo tubes by Micro Group). The number of conduits (e.g., 10, 20, 30, etc.) may be selected to provide a sufficient capacity for the selected volume of fluid sample to be passed through the conduits. Use of a relatively large number of conduits may be useful to ensure the continued operation of the fluid handling system 1100 even if one or a few conduits is blocked or otherwise fails. The surfaces of the conduits exposed to the fluid sample may be made substantially smooth (e.g., polishing, deburring, etc.) to facilitate the flow of the fluid sample through the conduits. A variety of materials may be used for the conduit holding block 1252, e.g., plastics including Delrin® available from DuPont. The conduits may be press fit into the channels 1224 of the conduit holding block 1252 and, optionally, adhered with an adhesive suitable for the materials used (e.g., Loctite® available from Henkel). The conduit holding block 1252 may be mounted to the first and second syringe bodies 1220a,b by inserting the conduit holding block 1252 into the first bore 1228a of the first syringe body 1220a at the first opening 1232a and inserting the inner tubular projection 1248 at the first end 1236a of the first syringe body 1220a into the second syringe body 1220b at the fourth opening 1240b. The dimensions of the conduit holding block 1252, e.g., the outer diameter, may be selected to provide a sufficiently close fit within the first bore 1228a of the first syringe body 1220a to provide a seal against the passage of the fluid sample around the outer surface of the conduit holding block 1252.

Figure 21:
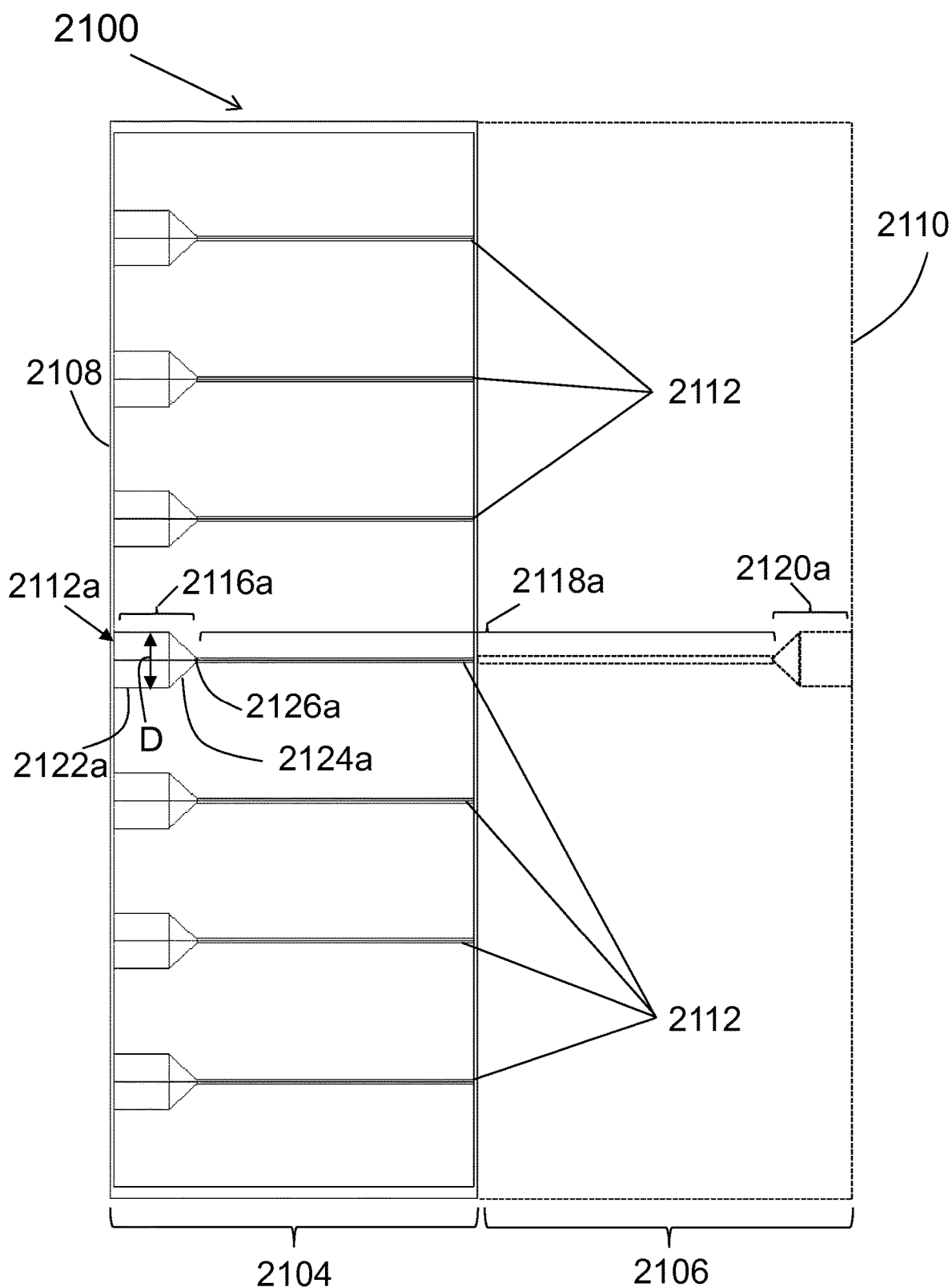
FIG. 21 shows a cross-sectional view of a conduit holding block according to an exemplary embodiment.

Another embodiment of a conduit holding block 2100 is shown in FIG. 21. FIG. 21 shows a cross-sectional view of a first half 2104 of the conduit holding block 2100. For clarity, a corresponding half 1280 and a corresponding section 1284 are marked on the conduit holding block of FIG. 12D to indicate which half and which cross-sectional view is being shown in FIG. 21. In addition, a second half 2106 of the conduit holding block 2100 is indicated with a dotted line in FIG. 21. The conduit holding block 2100 has a first face 2108, a second face 2110 opposite to the first face 2108 and a plurality of substantially parallel channels 2112 formed therein, each channel extending from the first face 2108 to the second face 2110. In this embodiment, each channel of the plurality of substantially parallel channels 2112 is configured to accelerate the flow of the fluid sample into a corresponding conduit of the plurality of substantially parallel conduits embedded within the channel. Such a configuration allows for fully developed flow of the fluid sample throughout the length of the conduit, e.g., as opposed to the flow only becoming fully developed part-way down the length of the conduit. Fully developed flow results in components of the fluid sample (e.g., cells) being exposed to higher peak fluid shear stress. Exposure to the target peak fluid shear stress throughout the length of the conduit results in more pronounced effects (e.g., fewer viable cells after exposure to the fluid shear stress) as compared to configurations which do not accelerate flow.

Channel 2112a of the plurality of substantially parallel channels 2112 is labeled (half of channel 2112a is indicated with a dotted line) in FIG. 21. Channel 2112a has an inner surface defined by the conduit holding block 2100. The inner surface is shaped to define a first funnel region 2116a, an elongated intermediate region 2118a, and a second funnel region 2120a. The first funnel region 2116a extends from the first face 2108 of the conduit holding block 2100 towards the elongated intermediate region 2118a. The second funnel region 2120a extends from the second face 2110 towards the elongated intermediate region 2118a. The particular shapes and dimensions of the first and second funnel regions 2116a, 2120a may vary, depending, at least in part, upon the degree of flow acceleration desired. In the embodiment of FIG. 21, the first funnel region 2116a has a cylindrical section 2122a having a diameter D and a conical section 2124a which terminates at an opening 2126a having a diameter d at the elongated intermediate region 2118a. The dimensions of the cylindrical section 2122a and the conical section 2124a may vary, again, depending at least in part, upon the degree of flow acceleration desired. However, d will be less than D. The dimensions of the intermediate region 2118a may also vary, depending upon the dimensions of the conduit of the plurality of substantially parallel conduits to be embedded therein. In some embodiments, the lengths of the first funnel region 2116a and the second funnel region 2120a are each about 1.5 mm and the length of the intermediate region is about 19.05 mm (giving a total length for channel 2112a of about 22.05 mm). As shown in FIG. 21, the second funnel region 2120a may be configured similarly to the first funnel region 2116a. In addition, each of the channels of the plurality of substantially parallel channels 2112 may be configured similarly to channel 2112a. By contrast, each of the channels of the plurality of substantially parallel channels 1224 of the conduit holding block 1252 of FIG. 12D has an inner surface shaped to define a continuous bore having a substantially uniform diameter along its length (see FIG. 12A).

Various alternative embodiments may be used. For example, in some embodiments, the first funnel region 2116a does not have the cylindrical section 2122a at all, i.e., only has the conical section 2124a. In some embodiments, channels of the plurality of substantially parallel channels 2112 may each have a single funnel region (rather than two), extending from the first face 2108 of the conduit holding block 2100 towards an elongated intermediate region which extends towards the second face 2110 of the conduit holding block. The single funnel region may have various shapes (e.g., a conical shape) and various dimensions (e.g., a length of about 3 mm). The elongated intermediate region may have various dimensions (e.g., a length of about 19.05 mm).

The syringe assembly 1104 may include a first piston (not shown) mounted in the first bore 1228a of the first syringe body 1220a and a second piston (not shown) mounted in the second bore 1228b of the second syringe body 1220b. A variety of pistons may be used for the first and second pistons. For example, as shown in FIG. 13, a syringe plunger 1300 of a disposable syringe (e.g., a 20 mL disposable syringe by McMaster Can) may be used for each of the first and second pistons. The syringe plunger 1300 may have a working end 1304 having a working face 1308 and a handle end 1312 connected by a plunger rod 1316. The working end 1304 of the first syringe plunger 1300 may be inserted into the first bore 1228a at the second opening 1240a of the first syringe body 1220a. Similarly, a working end of a second plunger may be inserted into the second bore 1228b at the third opening 1232b of the second syringe body 1220b.

Figure 13A:
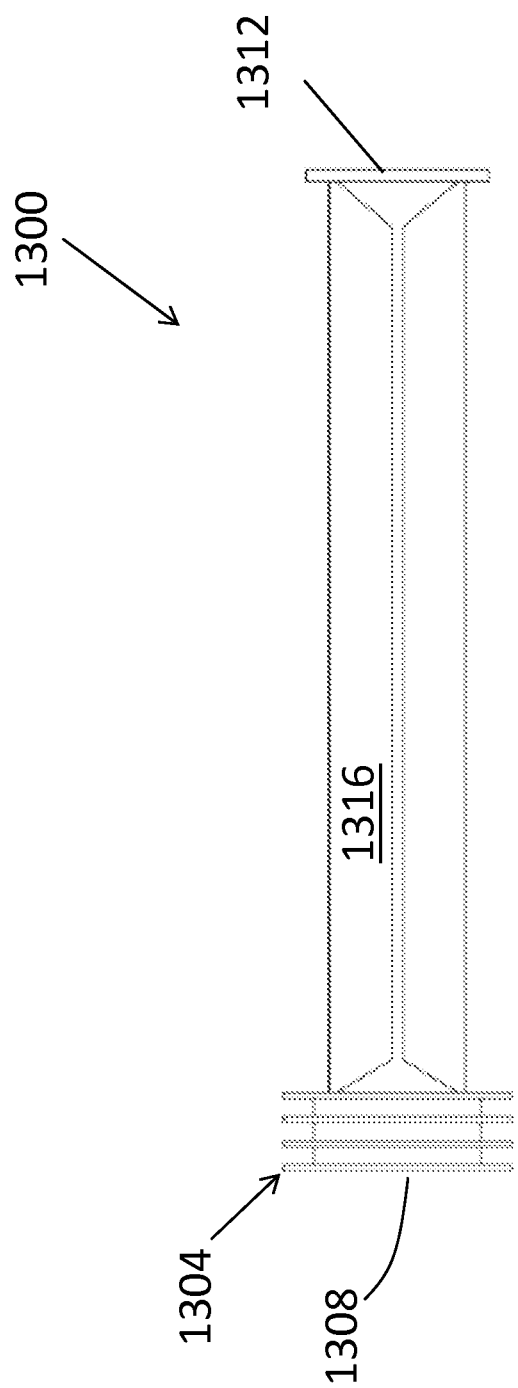
FIG. 13A shows a syringe plunger which may be used for the fixed pistons of the fluid handling system of FIG. 11.
Figure 13C:
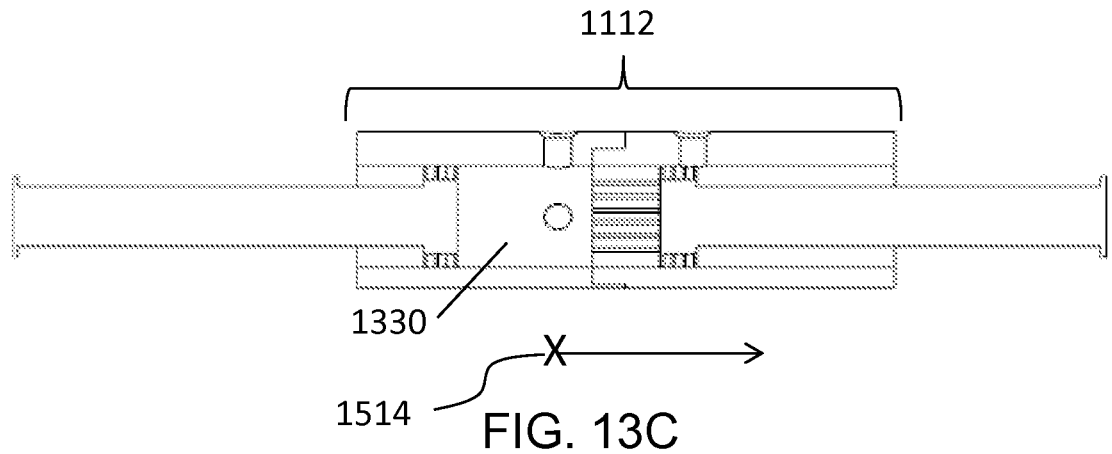
FIG. 13C shows the sample receptacle assembly of FIG. 13B, translated to the right.
Figure 13B:
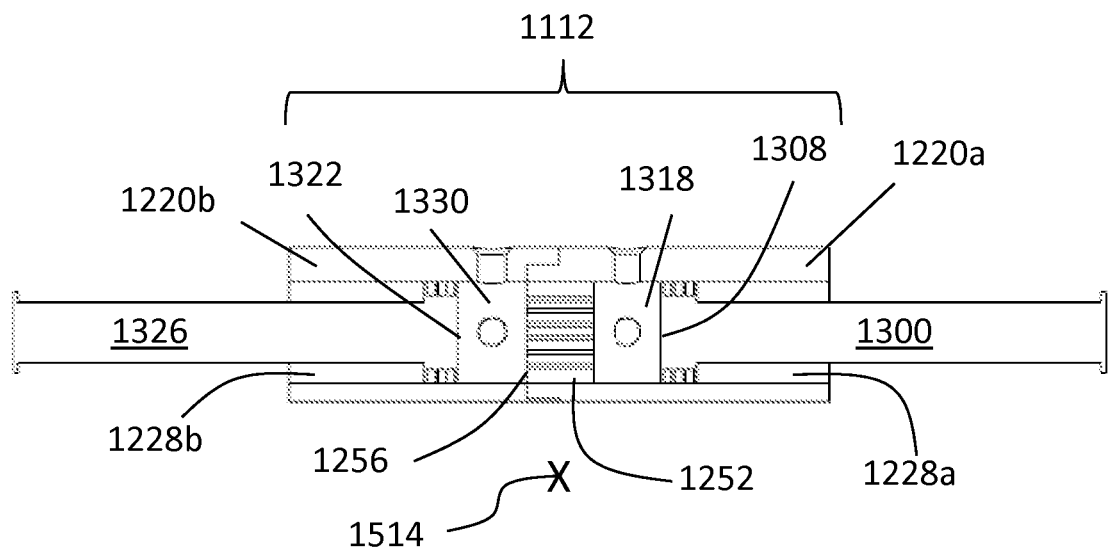
FIG. 13B shows a front, cross-sectional view of the sample receptacle assembly of FIG. 12A with the syringe plunger of FIG. 13A as the first piston and a similar syringe plunger as the second piston.
Figure 13D:
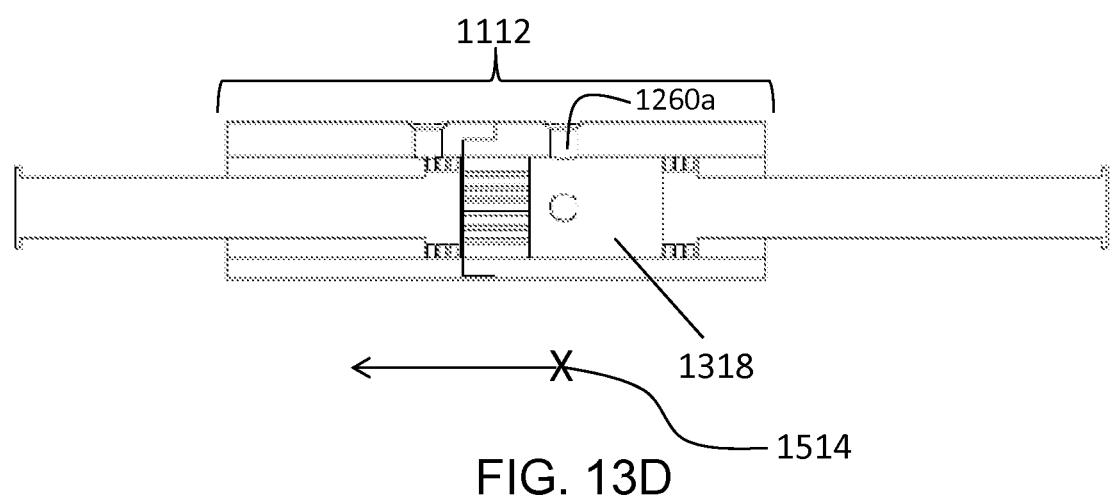
FIG. 13D shows the sample receptacle assembly of FIG. 13B, translated to the left.
Figure 14:
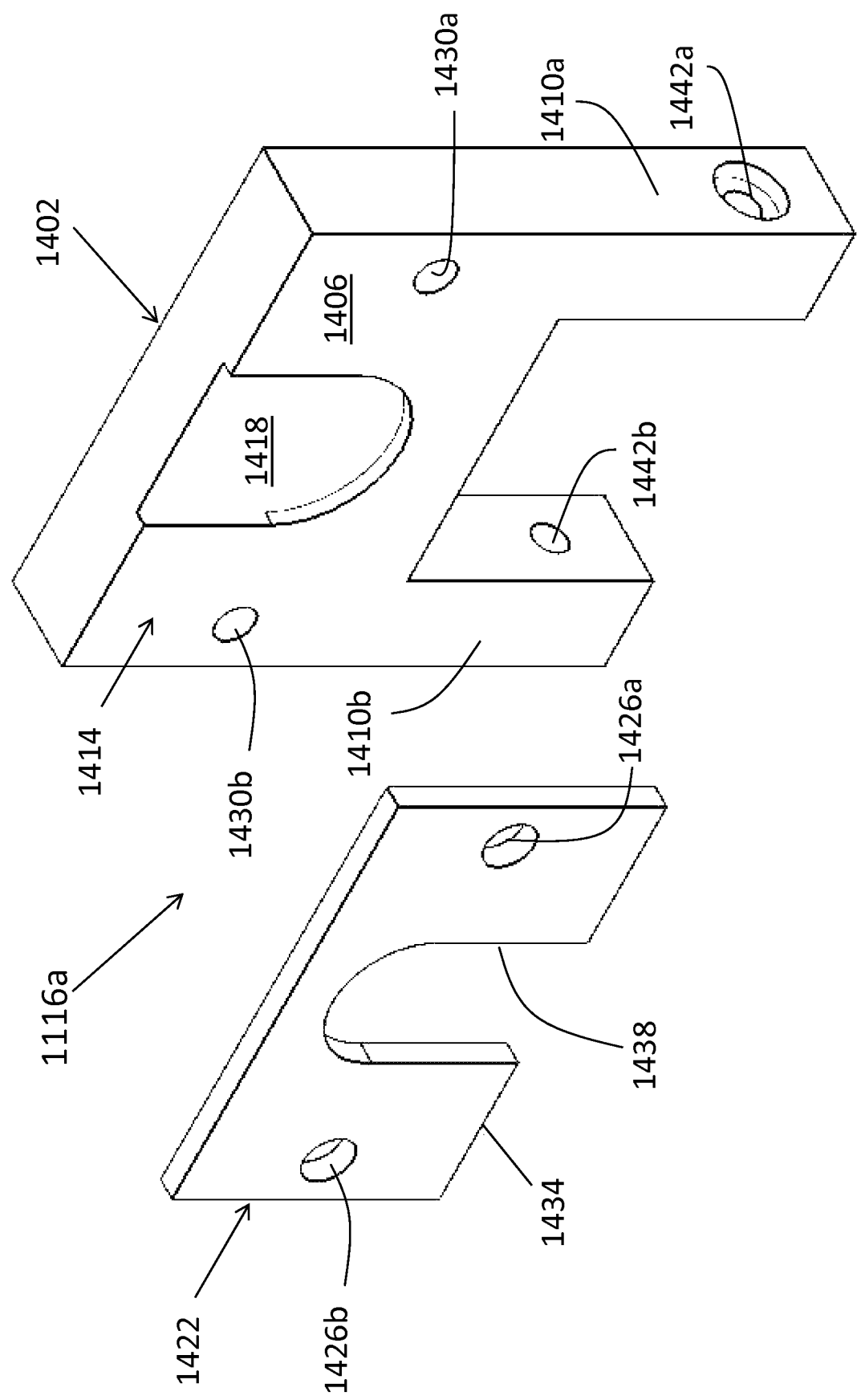
FIG. 14 shows an exemplary embodiment of a first piston anchor assembly of the fluid handling system of FIG. 11, which may be used with the syringe plunger of FIG. 13A.

With reference to FIGS. 11A-B and FIG. 14, the syringe assembly 1104 may include the first piston anchor assembly 1116a configured to support the first piston in a fixed position relative to a location in the fluid handling system 1100, e.g., a center 1514 of a top plate 1518 of a housing 1502 of the linear drive assembly 1108 (with reference to FIG. 15). Similarly, the syringe assembly 1104 may include a second piston anchor assembly 1116b configured to support the second piston in a fixed position relative to the location. Various configurations of the first piston anchor assembly 1116a and the second piston anchor assembly 1116b may be used. FIG. 14 shows an exemplary embodiment of the first piston anchor assembly 1116a, which may be used with the syringe plunger 1300 (with reference to FIG. 13) as the first piston. The first piston anchor assembly 1116b may include a back stop 1402 having a body 1406 and legs 1410a,b extending downwardly from the body 1406. A front face 1414 of the back stop 1402 may define a depression 1418 having an outline shaped to accommodate the handle end 1312 of the syringe plunger 1300. The first piston anchor assembly 1116a may further include a locking plate 1422 mountable to the back stop 1402 (e.g., via fasteners (not shown) inserted through holes 1426 a,b defined in the locking plate 1422 and holes 1430 a,b defined in the body 1406 of the back stop 1402). The locking plate 1422 may have a bottom edge 1434 defining a slot 1438 having an outline shaped to accommodate the plunger rod 1316 of the syringe plunger 1300. The syringe plunger 1300 may be mounted to the first piston anchor assembly 1116a by inserting the handle end 1312 of the syringe plunger 1300 into the depression 1418 on the back stop 1402 and by placing the slot 1438 in the locking plate 1422 over the plunger rod 1316 of the syringe plunger 1300 such that the handle end 1312 is sandwiched between the back stop 1402 and the locking plate 1422. FIG. 11B shows the assembled view of the back stop 1402 and the locking plate 1422. As shown in FIG. 11A-B, the second piston anchor assembly 1116b may be similarly configured to the first piston anchor assembly 1116a.

As shown in FIG. 11B, the first piston anchor assembly 1116a and the second piston anchor assembly 1116b may be mounted to a component of the fluid handling system 1100, e.g., the housing 1502 of the linear drive assembly. For example, with reference to FIGS. 11B, 14 and 15, a rod having threaded ends may be inserted into a hole 1442a in the leg 1410a of the back stop 1402 of the first piston anchor assembly 1116a, a first elongated slot 1506a of a side wall 1510a of the housing 1502 of the linear drive assembly 1108, a second elongated slot 1506b of a side wall 1510b of the housing 1502 of the linear drive assembly 1108 and a hole 1442b in the opposite leg 1410b of the back stop 1402 of the first piston anchor assembly 1116a. The rod may be secured via caps or nuts on the threaded ends. The second piston anchor assembly 1116b may be similarly mounted to the housing 1502 of the linear drive assembly 1108. The first piston anchor assembly 1116a and the second piston anchor assembly 1116b may be mounted at a selected distance from the center 1514 of the top plate 1518 of the housing 1502 of the linear drive assembly 1108. The selected distance for the first piston anchor assembly 1116a may be the same or different as the selected distance for the second piston anchor assembly 1116b. The selected distance thus positions each working end of each syringe plunger mounted to each piston anchor assembly at a fixed position relative to the center 1514. The selected distance (and thus the selected fixed position) may be adjusted by mounting the first piston anchor assembly 1116a and/or the second piston anchor assembly 1116b at different position(s) along the elongated slots 1506a, b of the housing 1502 of the linear drive assembly 1108.

FIG. 13B shows a front, cross-sectional view of the sample receptacle assembly 1112 of FIG. 12A with the syringe plunger 1300 of FIG. 13A as the first piston and a second syringe plunger 1326 as the second piston. Together, the second face of the conduit holding block 1252, the walls of the first syringe body 1220a, and the working face 1308 of the syringe plunger 1300 inserted into the first bore 1228a of the first syringe body 1220a define a first sample chamber 1318 in the sample receptacle assembly 1112. Similarly, the first face 1256 of the conduit holding block 1252, the walls of the second syringe body 1220b and a working face 1322 of the second syringe plunger 1326 inserted into the second bore 1228b of the second syringe body 1220b define a second sample chamber 1330 in the sample receptacle assembly 1112.

As described further below, the sample receptacle assembly 1112 may translate back and forth along the longitudinal axis 1128 (with reference to FIG. 11B) of the sample receptacle assembly 1112 as a unit with respect to the first piston and the second piston which may be fixed in position along the longitudinal axis 1128. As a result, the volume of each of the first sample chamber 1318 and the second sample chamber 1330 may vary, e.g., from about 0 mL to a maximum volume. In FIG. 13B, the midpoint of the sample receptacle assembly 1112 is positioned over the center 1514. In FIG. 13C, the sample receptacle assembly 1112 has been translated to the right as indicated by the arrow with respect to the center 1514, resulting in the volume of the second sample chamber 1330 increasing to the maximum volume and the volume of the first sample chamber 1318 decreasing to about 0 mL. In FIG. 13D, the sample receptacle assembly 1112 has been translated to the left as indicated by the arrow with respect to the center 1514, resulting in the volume of the second sample chamber 1330 decreasing to about 0 mL and the volume of the first sample chamber 1318 increasing to the maximum value. The maximum volume may be that which can accommodate the selected volume of fluid sample. The dimensions of the first syringe body 1220a, the conduit holding block 1252, the second syringe body 1220b, as well as the selected fixed positions of the first piston and the second piston may be selected to provide the maximum volume.

Since it is the relative motion between the sample receptacle assembly 1112 and the first and second pistons that is relevant, it is to be understood that the operational states shown in FIGS. 13B-D may also be achieved by translating moveable first and second pistons relative to a fixed sample receptacle assembly 1112. The first and second pistons may be moved independently or together as a unit. The positions of the first and second pistons may be fixed relative to each other. Thus, in this disclosure, "relative translation of the sample receptacle assembly 1112 to the first and second pistons" and "translating the sample receptacle assembly 1112 relative to the first and second pistons" encompasses embodiments in which the sample receptacle assembly 1112 is physically moved relative to first and second pistons and in which first and second pistons are physically moved relative to the sample receptacle assembly 1112. Both embodiments achieve mechanical translation of a surface against the fluid sample contained in the first or second sample chambers 1318, 1330 in order to push the fluid sample through the plurality of substantially parallel conduits.

With reference to FIG. 12A-C, a first sample port 1260a may be defined in the walls of the first syringe body 1220a through which the fluid sample may be loaded or removed from the first sample chamber. Similarly, a second sample port 1260b may be defined in the walls of the second syringe body 1220b through which the fluid sample may also be loaded or removed from the second sample chamber. A first sensor port 1264a may also be defined in the walls of the first syringe body 1220a through which a first sensor (e.g., a first pressure sensor) may be inserted into the first sample chamber. Similarly, a second sensor port 1264b may also be defined in the walls of the second syringe body 1220b through which a second sensor (e.g., a second pressure sensor) may be inserted into the second sample chamber. Pressure sensors enable the pressure in the sample chambers to be monitored during the operation of the fluid handling system 1100. Such monitoring may be used to provide an indication of plugging in one or more of the conduits. Sample ports 1260a, b may be sealed via threaded caps or threaded plugs. Pressure sensors may be inserted into the pressure ports 1264a, b using luer fittings. Commercially available pressure sensors may be used, e.g., Meritrans® Pressure Transducers, BP Series by Merit Medical.

With reference to FIG. 12E, bottom surfaces 1270a, b of the first and second syringe bodies 1220a, b may be flattened for mounting the sample receptacle assembly 1112 to a carriage plate 1120 (with reference to FIG. 11A-B). In addition, the bottom surfaces 1270a, b may define a plurality of cavities 1274a, b, respectively, in which the ends of a plurality of locking pins 1124 a, b (with reference to FIG. 11A) may be inserted, respectively. Opposing ends of the plurality of locking pins 1124 a, b may be inserted into another plurality of cavities (not labeled in FIG. 11A) defined in a top surface of the carriage plate 1120.

Figure 15A:
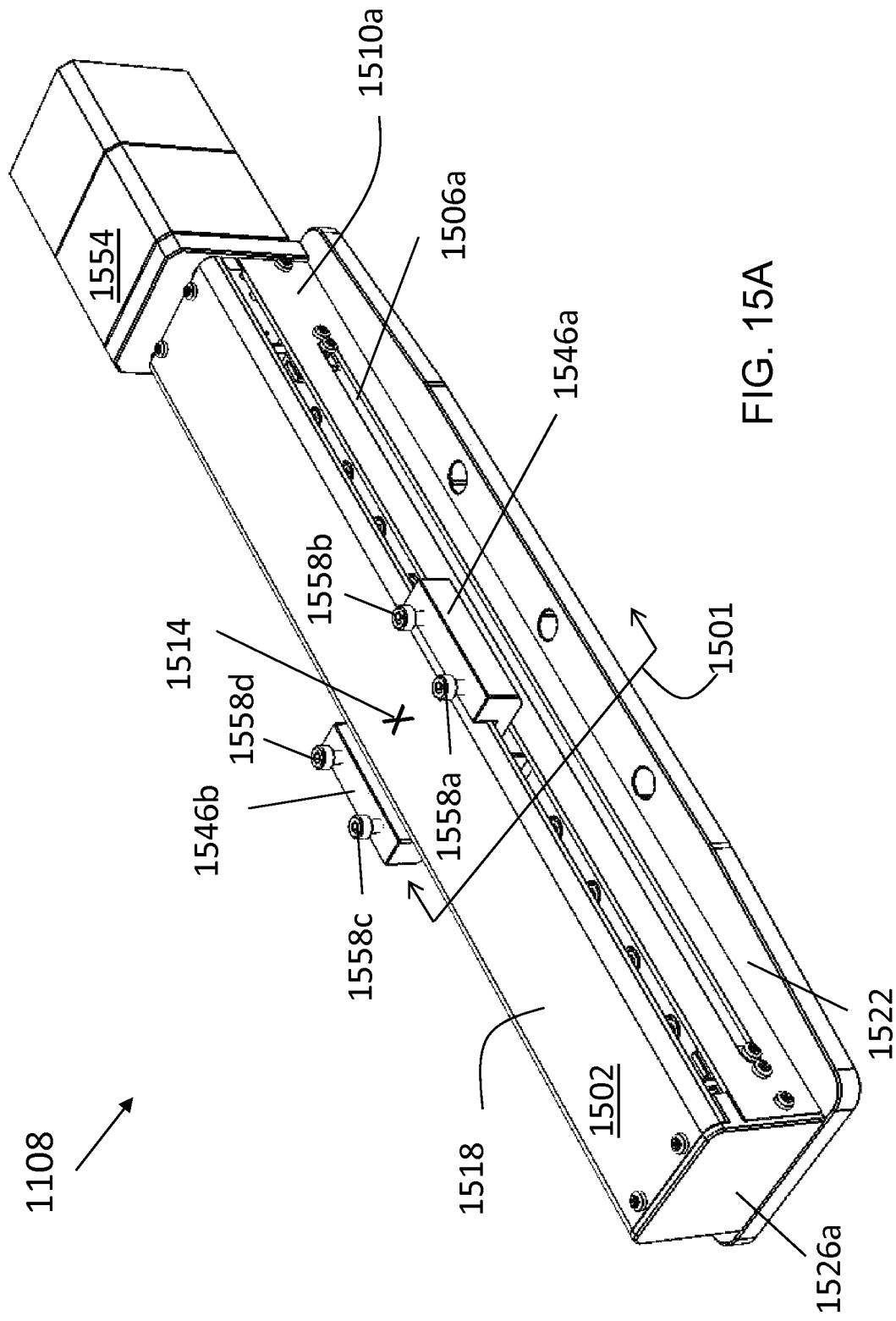
FIG. 15A shows a perspective view of a linear drive assembly of the fluid handling system of FIG. 11.
Figure 15B:
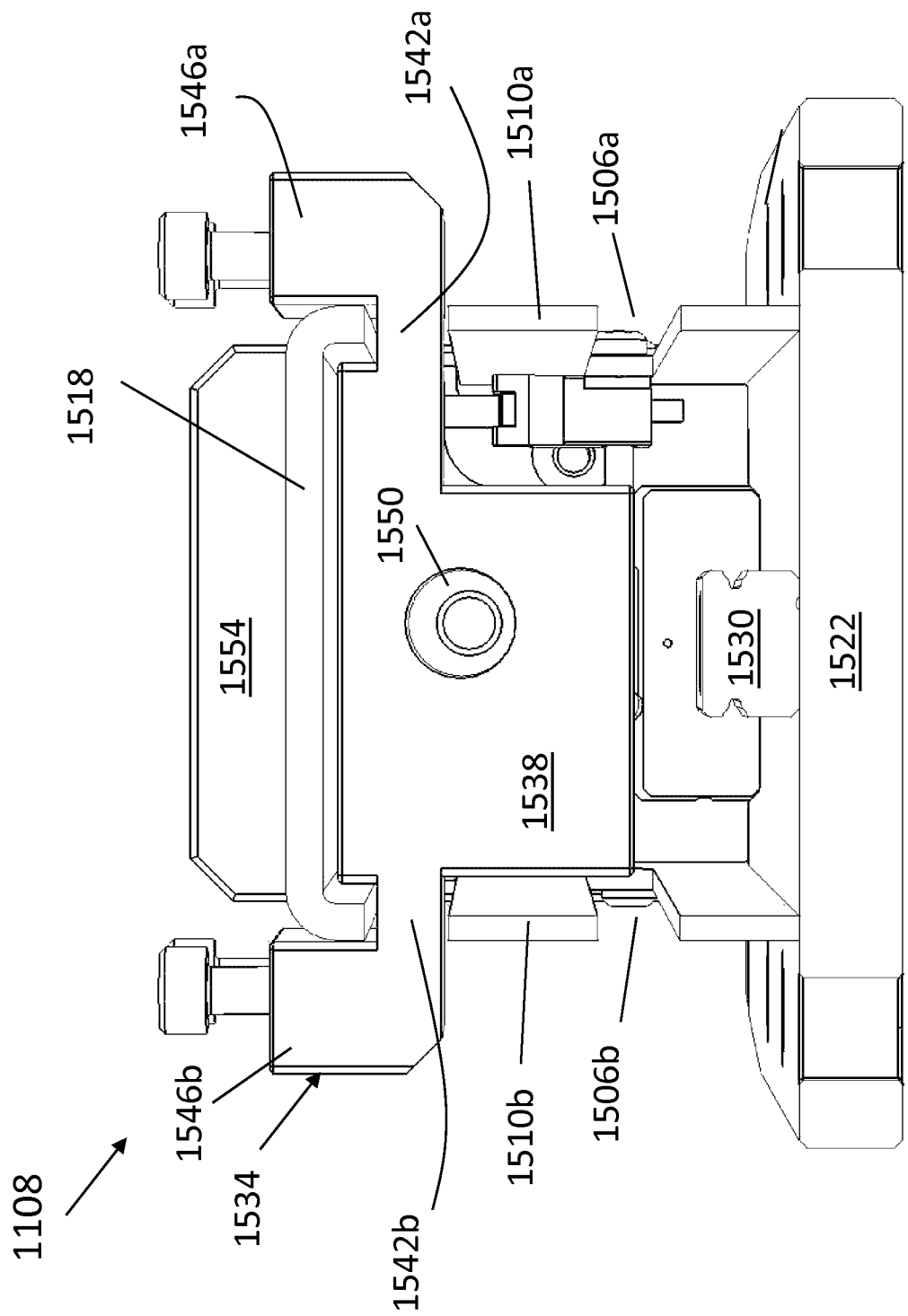
FIG. 15B shows a cross-sectional view of the linear drive assembly.

With reference to FIG. 11B, as described above, the fluid handling system 1100 may include the linear drive assembly 1108 mounted to the syringe assembly 1104. The linear drive assembly 1108 may be configured to translate a device back and forth along the longitudinal axis 1128 of the syringe assembly 1104 (e.g., the sample receptacle assembly 1112 or the first and second pistons). A variety of linear drive assemblies may be used, including commercially available linear drive assemblies, e.g., MSL-200 by Newmark Systems, Inc. Such an exemplary linear drive assembly 1108 is shown in FIGS. 15A-B. FIG. 15 shows a perspective view of the linear drive assembly 1108. FIG. 15B shows a cross-sectional view of the linear drive assembly 1108 taken along section 1501. The linear drive assembly 1108 may include the housing 1502 having a base plate 1522, side walls 1510 a, b and end walls (one of which is labeled 1526a) mounted to and extending from the base plate 1522, and the top plate 1518 mounted to the side walls 1510a, b and end walls. As described above, the first elongated slot 1506a defined in the side wall 1510a and the second elongated slot 1506b defined in the side wall 1510b may be used to mount the first piston anchor assembly 1116a and the second piston anchor assembly 1116b in different positions along the elongated slots 1506a, b.

The linear drive assembly 1108 may include a bearing rail 1530 mounted to the base plate 1522. The linear drive assembly 1108 may include a device support assembly 1534 which may include a carriage base 1538 mounted to the bearing rail 1530. The carriage base 1538 may include side projections 1542a, b which extend from the sides of the carriage base 1538 through gaps defined between the top plate 1528 and the side walls 1510a, b, respectively, of the housing 1502. The side projections 1542a, b include horizontal support bars 1546a, b which extend upwardly from top surfaces of each side projection 1542a, b and run substantially parallel to the top plate 1518. A bore 1550 defined in the carriage base 1538 forms a lead screw interface with a lead screw (not shown) mounted between the end walls and extending substantially parallel to an axis parallel to the longitudinal axis 1128 of the syringe assembly 1104 (with reference to FIG. 11B). The carriage base 1538 translates along the lead screw and the bearing rail 1530. The linear drive assembly 1108 may include an actuator 1554 mounted to drive translation of the carriage base 1538 back and forth along the lead screw and thus, translation of any device mounted to the carriage base 1538. In the exemplary embodiment, the actuator 1554 is a stepper motor, but other actuators may be used, e.g., an electric motor, a piezo motor, etc.

The linear drive assembly 1108 may be configured to move a device, e.g., the sample receptacle assembly 1112 in other directions, in addition to linear translation along the longitudinal axis 1128 (with reference to FIG. 11B).

As shown in FIGS. 11A-B, the carriage plate 1120 may be mounted to the carriage base 1538 (with reference to FIG. 15B) of the linear drive assembly 1108. The carriage plate 1120 may be mounted to the carriage base 1538 using a plurality of fasteners 1558*a-d* (with reference to FIG. 15A) inserted through holes (see FIG. 11A, not labeled) defined in the carriage plate. The sample receptacle assembly 1112 may be mounted to the carriage plate 1120 as described above.

Unless otherwise described, the components of the fluid handling system 1100 may be formed from a variety of materials having sufficient strength and rigidity for the described application.

Figure 16:
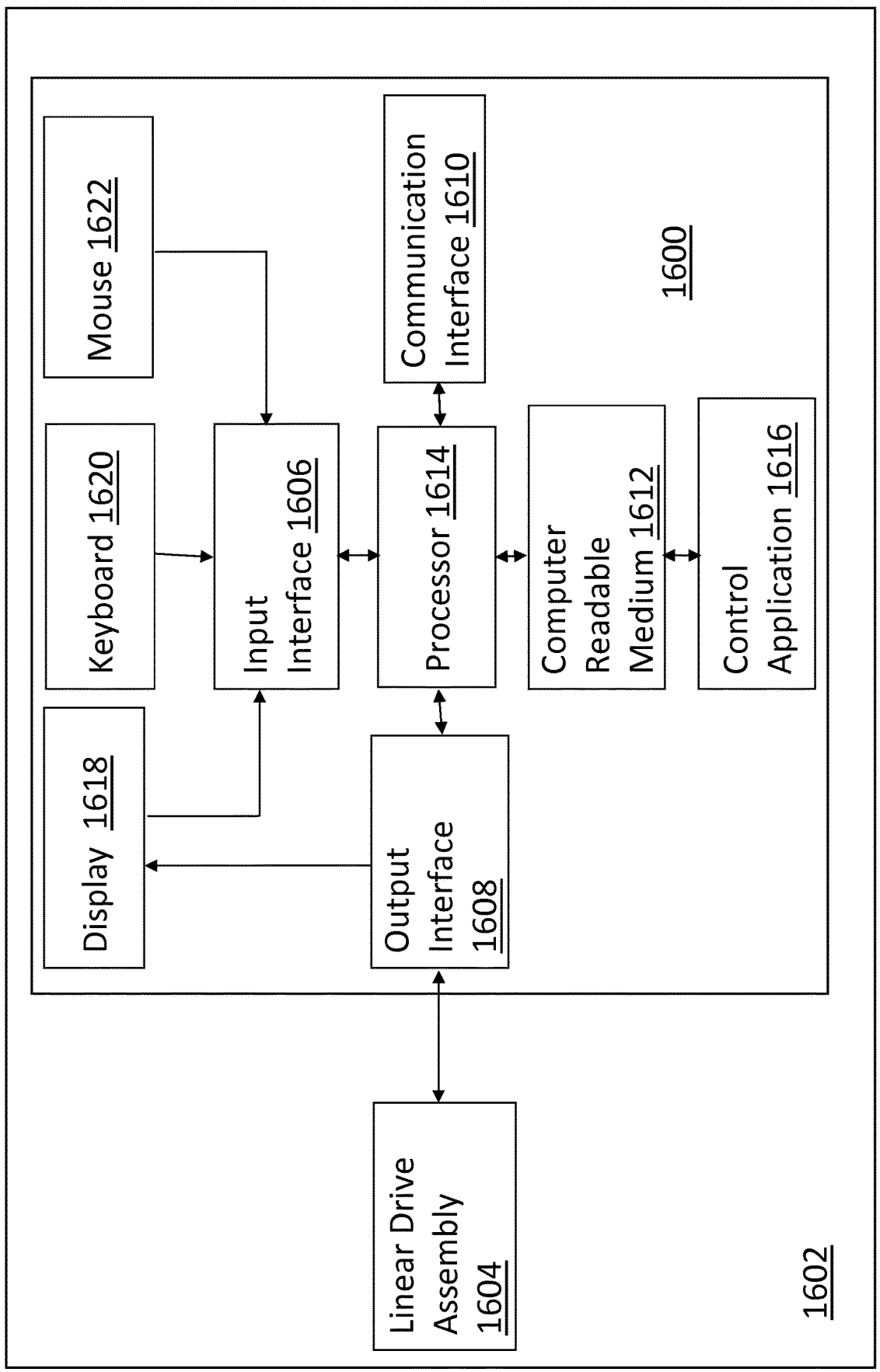
FIG. 16 depicts a control system of a fluid handling system based on mechanical pressure according to an exemplary embodiment.

With reference to FIG. 16, an exemplary embodiment of a control system 1600 of a fluid handling system 1602 is shown. The control system 1600 controls the operation of various components of the fluid handling system 1602 and may be used to automate the application of the plurality of pulses of fluid shear stress to the fluid sample. For example, the control system 1600 may be operably coupled to a linear drive assembly 1604 of the fluid handling system 1602. With reference to the fluid handling system 1100 shown in FIG. 11, the control system 1600 may be used to control the translation of the carriage base 1120 back and forth along the longitudinal axis 1128 of the syringe assembly 1104 and thus, the translation of the sample receptacle assembly 1112 mounted thereon. For example, the control system 1600 may be used to repeatedly translate the mounted sample receptacle assembly 1112 over a selected distance between an initial position and a selected position at a selected speed. One or more of the components of the control system 1600 may be mounted on a printed circuit board mounted on another component of the fluid handling system 1602.

The control system 1600 may include an input interface 1606, an output interface 1608, a communication interface 1610, a computer-readable medium 1612, a processor 1614, and a control application 1616. The control system 1600 may include fewer or additional components as compared to those shown in FIG. 16.

Input interface 1606 provides an interface for receiving information from the user for processing by control system 1600. Although not shown, input interface 1606 may further provide an interface for receiving information from the linear drive assembly 1604 for processing by control system 1600. Input interface 1606 may interface with various input technologies including, but not limited to, a display 1618, a keyboard 1620, a mouse 1622, a touch screen, a track ball, a keypad, etc. to allow the user to enter information into control system 1600 or to make selections presented in a user interface displayed on display 1618. Display 1618 may be a thin film transistor display, a light emitting diode display, a liquid crystal display, or any of a variety of different displays known to those skilled in the art. Control system 1600 may have one or more input interfaces that use the same or a different input interface technology.

Output interface 1608 provides an interface for outputting information for review by a user of fluid handling system 1602. Such information may include an output signal from a pressure sensor mounted to the fluid handling system 1602 or a voltage signal from an actuator of the linear drive assembly 1604. Monitoring such signals during the operation of the fluid handling system 1602 provides a diagnostic on the fluid sample transfer conditions which may inform the user of abnormal conditions, e.g., an undesired flow rate or conduit plugging. Output interface 1608 may further provide an interface for outputting information to the linear drive assembly 1604. Control system 1600 may have one or more output interfaces that use the same or a different interface technology.

Communication interface 1610 provides an interface for receiving and transmitting data between devices using various protocols, transmission technologies, and media as known to those skilled in the art. Communication interface 1610 may support communication using various transmission media that may be wired or wireless. Exemplary wireless communication devices include antennas that receive and transmit electromagnetic radiation at various frequencies. Control system 1600 may have one or more communication interfaces that use the same or a different communication interface technology. Data and messages may be transferred between any input or output device and controller 1600 using communication interface 1610. Thus, communication interface 1610 provides an alternative (or additional) interface to either or both of input interface 1606 and output interface 1608.

Control system 1600 may be linked to one or more interfaced devices. For example, control system 1600 may interface with another fluid handling system, an external computing device, an external system for analyzing certain characteristics of collected processed fluid samples. If connected, control system 1600 and the one or more interfaced devices may be connected directly or through a network. The network may be any type of wired and/or wireless public or private network including a cellular network, a local area network, a wide area network such as the Internet, etc. Control system 1600 may send and receive information to/from one or more of the interfaced devices. For example, control system 1600 may send results obtained for the fluid sample for storage on one or more of the interfaced devices. As another example, control system 1600 may receive software updates from one or more of the interfaced devices and/or receive commands from one or more of the interfaced devices. The commands may control operation of one or more components of fluid handling system 1602 including control system 1600. The one or more interfaced devices may include a computing device of any form factor such as a personal digital assistant, a desktop computer, a laptop computer, an integrated messaging device, a cellular telephone, a smart phone, a pager, etc. without limitation.

Computer-readable medium 1612 is an electronic holding place or storage for information so that the information can be accessed by processor 1614 as known to those skilled in the art. Computer-readable medium 1612 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Control system 1600 may have one or more computer-readable media that use the same or a different memory media technology. Control system 1600 also may have one or more drives that support the loading of a memory media such as a CD or DVD.

Processor 1614 executes instructions as known to those skilled in the art. The instructions may be carried out by a special purpose computer, logic circuits, or hardware circuits. Thus, processor 1614 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 1614 executes an instruction, meaning that it performs/controls the operations called for by that instruction. Processor 1614 operably couples with input interface 1606, with computer-readable medium 1612, with communication interface 1610, and with output interface 1608 to receive, to send, and to process information. Processor 1614 may retrieve a set of instructions from a permanent memory device and copy the instructions in an executable form to a temporary memory device that is generally some form of RAM. Control system 1600 may include a plurality of processors that use the same or a different processing technology.

Control application 1616 performs operations associated with controlling the operation of fluid handling system 1602 and/or performs operations associated with processing output signals or input signals received by various components of fluid handling system 1602. Some or all of the operations described herein may be controlled by instructions embodied in control application 1616. The operations may be implemented using hardware, firmware, software, or any combination of these methods. With reference to the example embodiment of FIG. 16, control application 1616 may be implemented in software (comprised of computer-readable and/or computer-executable instructions) stored in computer-readable medium 1612 and accessible by processor 1614 for execution of the instructions that embody the operations of control application 1616. Control application 1616 may be written using one or more programming languages, assembly languages, scripting languages, etc.

In an exemplary embodiment, the fluid handling system 1602 may be configured as shown in FIG. 11-15 (including a MSL-200 by Newmark Systems, Inc. as the linear drive assembly 1604) and the control system 1600 may include a computer, a NSC-Al Stepper Motor Controller by Newmark Systems, Inc. and a NSC-Al Program by Newmark Systems, Inc. as the control application 1616.

The following exemplary operations may be carried out when using any of the disclosed fluid handling systems based on mechanical pressure to apply a plurality of pulses of fluid shear stress to a fluid sample. At least some of these operations may be performed by the control system 1600 (including the control application 1616). The operations will be described with respect to the fluid handling system 1100 described in FIGS. 11-15 (including a MSL-200 by Newmark Systems, Inc. as the linear drive assembly 1604).

In a first operation, translate the sample receptacle assembly 1112 to an initial position. An exemplary initial position is shown in FIG. 13D in which the volume of the first sample chamber 1318 is at the maximum value and the volume of the second sample chamber 1330 is about 0 mL. Next, the fluid sample may be loaded into the first sample chamber 1318 via the first sample port 1260a. The first sample port 1260a may be sealed via a threaded plug. The fluid sample will be retained in the first sample chamber 1318.

In a second operation, translate the sample receptacle assembly 1112 from the initial position to the selected position in a first direction (e.g., −z) along the longitudinal axis 1128 (with reference to FIG. 11B) at the selected speed. The translation of the sample receptacle assembly 1112 and the fluid sample therein towards the fixed first piston results in a force being applied to the fluid sample in the first sample chamber 1318 which pushes the fluid sample from the first sample chamber 1318 through the plurality of substantially parallel conduits into the second sample chamber 1330, thereby exposing the fluid sample to a first pulse of fluid shear stress. The selected speed may be that which provides a selected flow rate of the fluid sample through the conduits (for conduits of a particular inner diameter). The selected flow rate provides a selected duration time for the first pulse of fluid shear stress (for conduits of a particular length). Similarly, the selected flow rate provides a selected magnitude of fluid shear stress for the first pulse of fluid shear stress (flow rate and fluid shear stress are related via Poiseuille's equation as described above). As also described above, fluid sample being passed through a conduit experiences a range of magnitudes of fluid shear stress from zero to a maximum value, with the magnitude depending upon its position relative to the longitudinal axis of the conduit. The "selected magnitude of fluid shear stress" may refer to the shear stress calculated at the wall of the conduit through which the fluid sample is passed. An exemplary selected speed may in the range of from about 0.75 mm/sec to about 7.5 mm/sec to provide a selected flow rate of about 25 µL/sec to about 250 µL/sec, respectively (for 30 conduits, each having a length of 1.27 cm and an inner diameter of 0.15 mm).

The second operation is illustrated in FIGS. 13B and C. FIG. 13B shows the sample receptacle assembly 1112 in an intermediate position in which some of the fluid sample from the first sample chamber 1318 has passed through the conduits into the second sample chamber 1330. FIG. 13D shows the sample receptacle assembly 1112 in the selected position in which substantially all the fluid sample has passed through the conduits into the second sample chamber 1330.

In a third operation, hold the sample receptacle assembly 1112 at the selected position for a selected hold time, e.g., 10 seconds, 30 seconds, etc. The hold time may be eliminated such that the hold time is effectively zero.

In a fourth operation, translate the sample receptacle assembly 1112 from the selected position back to the initial position in an opposing direction (e.g., +z) along the longitudinal axis 1128 at the selected speed (or a different selected speed) (with reference to FIG. 11B). The translation of the sample receptacle assembly 1112 and the fluid sample therein towards the fixed second piston results in a force being applied to the fluid sample in the second sample chamber 1330 which pushes the fluid sample from the second sample chamber 1330 through the plurality of substantially parallel conduits back into the first sample chamber 1318, thereby exposing the fluid sample to a second pulse of fluid shear stress. After the fourth operation, the sample receptacle assembly 1112 will be back in the initial position as shown in FIG. 13D.

In a fifth operation, hold the sample receptacle assembly 1112 at the initial position for the selected hold time (or a different selected hold time).

In subsequent operations, repeat the translating and holding operations until the fluid sample has passed through the plurality of substantially parallel conduits a selected total number of times (e.g., 5, 10, 15, etc.).

The exemplary operations above refer to translating the sample receptacle assembly 1112 relative to the first and second pistons. However, as described above, such operations may alternatively involve translating the first and second pistons relative to the sample receptacle assembly 1112.

After the application of one or more plurality of pulses of fluid shear stress, the fluid sample may be referred to as "a processed fluid sample" which may be collected and analyzed via a variety of techniques, e.g., techniques for determining the concentration of viable cells in the processed fluid sample, including those described in U.S. Pat. Pub. No. 20140038231. As shown in FIG. 12, the processed fluid sample may be collected via either the first sample port 1260*a* or the second sample port 1260*b*. Processed fluid sample may be collected during operation of the fluid handling system 1100, e.g., during one or more of the hold times. Thus, not only may processed fluid sample may be collected after the selected total number of passages (e.g., 10), but also, after any number of passages less than the total (e.g., 1, 2, 4, etc.).

It is to be understood that the use of the phrases "syringe body" and "bore" and the like in this disclosure is not limited to structures having circularly-shaped cross-sections, although such structures may be used.

EXAMPLES

A fluid handling system similar to those described in the section "Fluid Handling System Based on Gas Pressure" was used to apply pluralities of pulses of fluid shear stress to fluid samples which included cancerous cells, e.g., PC-3 cells. The fluid samples were prepared according to methods as described in U.S. Pat. Pub. No. 20140038231. The fluid samples were loaded onto the fluid handling system and processed using the operations described in "Fluid Handling System Based on Gas Pressure" to provide processed fluid samples. FIG. 17 shows the state of each gas valve (V1, V2, etc.) in each gas valve assembly during an exemplary set of operations and the corresponding flow rate of gas being delivered by the gas delivery system as determined via a flowmeter in the gas delivery system during the set of operations. In this example, relatively long hold times separated pairs of pulses of fluid shear stress while relatively short hold times separated the pulses of fluid shear stress in a pair. However, in other examples, hold times between all pulses of fluid shear stress were substantially equal.

FIG. 18 shows display output that was calculated from output signals provided by the control system for the exemplary set of operations, in which "passage" refers to a particular stackable syringe assembly, "t_start" indicates the time point at which the fluid sample begins to flow through the conduit of the stackable syringe assembly; "t_end" indicates the final time point at which passage of the fluid sample through the conduit is complete; "delta_t" indicates the duration time of the application of fluid shear stress; "flow rate" indicates the rate of flow of the fluid sample through the conduit; and "app. volume" indicates the approximate volume of the fluid sample in the sample chamber of the stackable syringe assembly. Unprocessed fluid samples (not exposed to any pulses of fluid shear stress) and processed fluid samples (exposed to different numbers of pulses, i.e., 2, 4, 6, 8 and 10, of fluid shear stress) were collected as described in "Fluid Handling System Based on Gas Pressure" and subsequently analyzed to determine the percent viability of the cancerous cells in the processed fluid samples according to methods as described in U.S. Pat. Pub. No. 20140038231.

Figure 19:
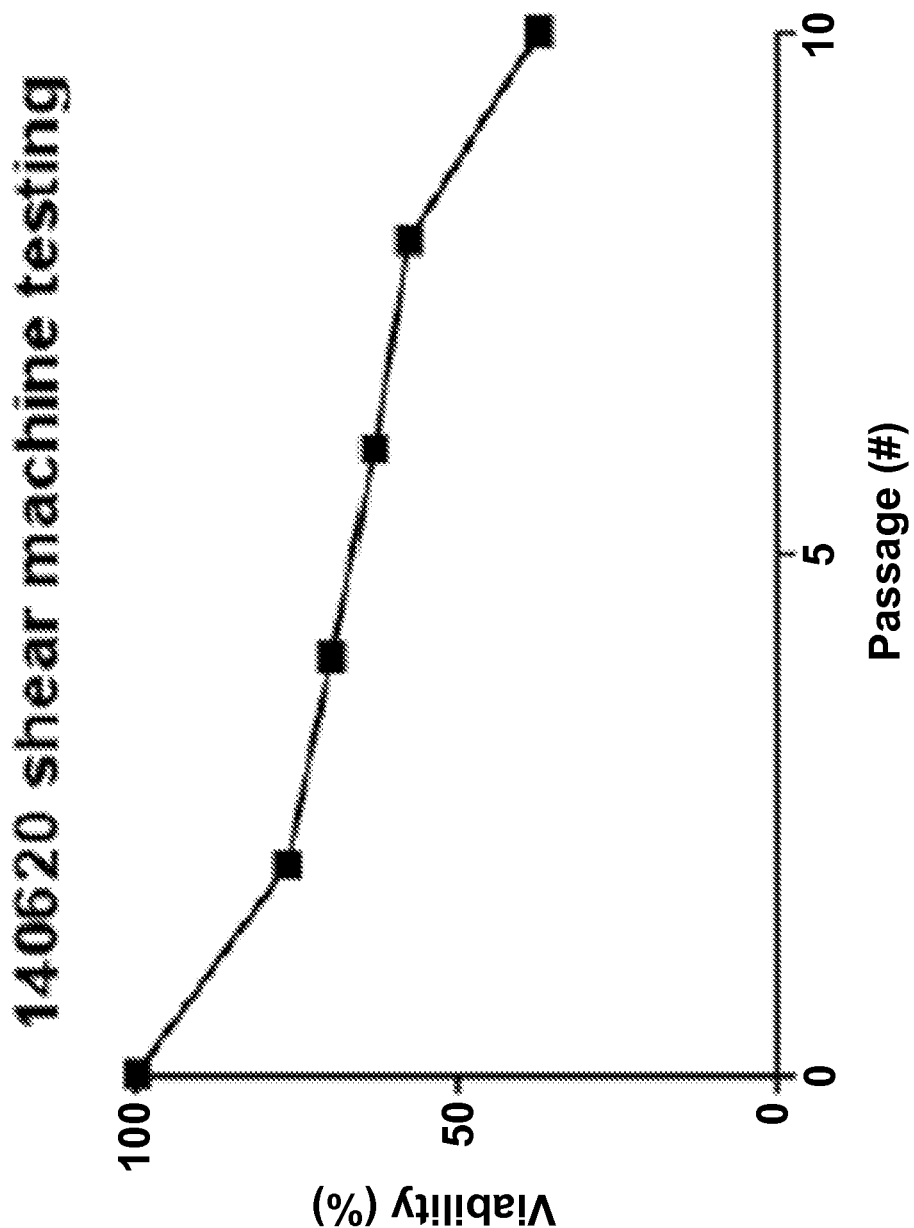
FIG. 19 shows the results from the exemplary set of operations of FIG. 17, i.e., the percent viability of cancerous cells in the fluid sample as a function of the number of pulses of fluid shear stress.

FIG. 19 shows the results from the exemplary set of operations, i.e., the percent viability of cancerous cells in the fluid sample as a function of the number of pulses of fluid shear stress.

The word "exemplary" is used herein to mean serving as an example, instance, or illustration. Any aspect or design described herein as "exemplary" is not necessarily to be construed as preferred or advantageous over other aspects or designs. Further, for the purposes of this disclosure and unless otherwise specified, "a" or "an" means "one or more".

The foregoing description of exemplary embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A fluid handling system for applying a plurality of pulses of fluid shear stress to a fluid sample, the system comprising:
   a first sample chamber;
   a second sample chamber;
   a plurality of conduits mounted between and in fluid connection with the first sample chamber and the second sample chamber, the plurality of conduits having inner diameters of less than about 1000 µm;
   a force delivery system mounted to the first sample chamber and configured to apply a selected force sufficient to push the fluid sample from the first sample chamber through each of the plurality of conduits at a constant flow rate to the second sample chamber, wherein the plurality of conduits are arranged in series and further wherein a third sample chamber is located between each pair of conduits in the plurality of conduits, and wherein the force delivery system is a gas delivery system configured to deliver gas to pressurize the first sample chamber and the second sample chamber to a selected pressure, the gas delivery system comprising a plurality of gas valves, each gas valve in fluid connection with the first sample chamber or the second sample chamber;
   a syringe stack comprising a plurality of stackable syringe assemblies, each stackable syringe assembly in fluid connection with an adjacent stackable syringe assembly, each stackable syringe assembly comprising:
   a syringe body defining a syringe sample chamber;
   a gas inlet port in fluid connection with the syringe sample chamber; and
   a syringe conduit through which the fluid sample may pass from the syringe sample chamber into an adjacent sample chamber of the adjacent stackable syringe assembly,
   wherein the syringe stack comprises the first sample chamber, the second sample chamber, the plurality of conduits and an additional sample chamber such that the syringe sample chamber is one of the first sample chamber, the second sample chamber and the third sample chamber and one of the plurality of conduits, and wherein each gas valve is in fluid connection with one of the plurality of stackable syringe assemblies via a gas inlet port.

2. The fluid handling system of claim 1, the syringe body comprising a bottom end portion configured such that the bottom end portion is insertable into a top opening of an adjacent syringe body of the adjacent stackable syringe assembly to form a pressure-tight seal.

3. The fluid handling system of claim 1, the stackable syringe assembly further comprising an arm defining a bore through which fluid may pass, the arm mounted to the syringe body and extending from the gas inlet port.

4. The fluid handling system of claim 1, the syringe body comprising a partition assembly mounted in the syringe sample chamber and configured to reduce foaming of the fluid sample as it passes into the syringe sample chamber en route to the syringe conduit.

5. The fluid handling system of claim 4, wherein the partition assembly comprises a central portion mounted to a side wall of the syringe body at a bottom end of the central portion, the central portion extending upwardly such that a top end of the central portion is positioned in a central location within the syringe sample chamber, and first and second lateral portions mounted to opposite sides of the top end of the central portion, wherein the central portion and first and second lateral portions define gaps through which the fluid sample may pass.

6. The fluid handling system of claim 1, further comprising a support assembly mounted to the syringe stack and configured to position the syringe stack vertically.

7. A fluid handling system for applying a plurality of pulses of fluid shear stress to a fluid sample, the system comprising:
   a first sample chamber;
   a second sample chamber;
   a plurality of conduits mounted between and in fluid connection with the first sample chamber and the second sample chamber, the plurality of conduits having inner diameters of less than about 1000 µm;
   a force delivery system mounted to the first sample chamber and configured to apply a selected force sufficient to push the fluid sample from the first sample chamber through each of the plurality of conduits at a constant flow rate to the second sample chamber, wherein the plurality of conduits are arranged in series and further wherein a third sample chamber is located between each pair of conduits in the plurality of conduits, and wherein the force delivery system is a gas delivery system configured to deliver gas to pressurize the first sample chamber and the second sample chamber to a selected pressure, the gas delivery system comprising a plurality of gas valves, each gas valve in fluid connection with the first sample chamber or the second sample chamber; and
   a control system operably coupled to the gas delivery system and configured to sequentially deliver gas to each sample chamber at the selected pressure for a selected duration time to sequentially pass the fluid sample through each conduit,
   wherein the control system is configured to perform operations comprising:
   (a) pressurizing the first sample chamber with gas to the selected pressure;
   (b) maintaining the pressurization at the selected pressure until an indicator indicates the complete delivery of the fluid sample through a first conduit in the plurality of conduits into an adjacent sample chamber;
   (c) venting the first sample chamber for a selected hold time; and
   (d) repeating steps (a)-(c) such that the fluid sample passes through each conduit in the plurality of conduits.

8. A fluid handling system for applying a plurality of pulses of fluid shear stress to a fluid sample, the system comprising:
   a first sample chamber;
   a second sample chamber;
   a plurality of conduits mounted between and in fluid connection with the first sample chamber and the second sample chamber, the plurality of conduits having inner diameters of less than about 1000 µm;
   a force delivery system mounted to the first sample chamber and configured to apply a selected force sufficient to push the fluid sample from the first sample chamber through each of the plurality of conduits at a constant flow rate to the second sample chamber, wherein the plurality of conduits are arranged parallel to one another and the force delivery system is a linear drive assembly to apply the selected force to the fluid sample in the first sample chamber at a selected speed over a selected distance and to apply the selected force in an opposing, second direction towards the fluid sample at the selected speed over the selected distance in the second sample chamber;
   a syringe body having a longitudinal axis and defining a bore, the first sample chamber within the bore and the second sample chamber within the bore, wherein the plurality of parallel conduits are mounted within the bore;
   a first piston mounted within the bore at an end of the syringe body; and
   a second piston mounted within the bore at an opposing end of the syringe body;
   wherein the linear drive assembly is configured to achieve relative translation of the syringe body to the first and second pistons back and forth along the longitudinal axis of the syringe body.

9. The fluid handling system of claim 8, wherein the syringe body is moveable and the first and second pistons are fixed in position.

10. The fluid handling system of claim 8, further comprising a conduit holding block mounted within the bore, the conduit holding block comprising a plurality of parallel channels, wherein the plurality of parallel conduits are mounted in corresponding channels of the plurality of parallel channels.

11. The fluid handling system of claim 10, wherein the plurality of parallel channels are arranged in an array.

12. The fluid handling system of claim 10, wherein one or more channels of the plurality of parallel channels has an inner surface defining a first funnel region and an elongated intermediate region, wherein the first funnel region extends from a face of the conduit holding block towards the elongated intermediate region and the elongated intermediate region extends towards to an opposing face of the conduit holding block, wherein the first funnel region is configured to accelerate the flow of the fluid sample into the one or more channels.

13. The fluid handling system of claim 12, wherein the first funnel region comprises a conical section.

14. The fluid handling system of claim 13, wherein the first funnel region further comprises a cylindrical section.

15. The fluid handling system of claim 12, wherein the inner surface further defines a second funnel region which extends from the opposing face of the conduit holding block towards the elongated intermediate region, wherein the second funnel region is configured to accelerate the flow of the fluid sample into the one or more channels.

16. The fluid handling system of claim 9, wherein the first fixed piston and the second fixed piston are each adjustably mounted to the linear drive assembly via a first piston anchor assembly and a second piston anchor assembly, respectively.

17. The fluid handling system of claim 8, further comprising a control system operably coupled to the linear drive assembly and configured to achieve relative translation of the syringe body to the first and second pistons back and forth over the selected distance between an initial position and a selected position at the selected speed to repeatedly pass the fluid sample through the plurality of parallel conduits.

18. The fluid handling system of claim 17, wherein the control system is configured to perform operations comprising:

(a) translating the syringe body relative to the first and second pistons from the initial position to the selected position in the first direction along the longitudinal axis at the selected speed to transfer the fluid sample from the first sample chamber to the second sample chamber through the plurality of parallel conduits;

(b) holding the syringe body relative to the first and second pistons at the selected position for a selected hold time;

(c) translating the syringe body relative to the first and second pistons from the selected position to the initial position in the opposing direction along the longitudinal axis at the selected speed to transfer the fluid sample from the second sample chamber to the first sample chamber through the plurality of parallel conduits;

(d) holding the syringe body relative to the first and second pistons at the initial position for the selected hold time; and (e) repeating steps (a)-(d) such that the fluid sample passes through the plurality of parallel conduits a selected number of times.

* * * * *